(12) United States Patent  (10) Patent No.: US 8,696,613 B2
Mastalli et al.  (45) Date of Patent: Apr. 15, 2014

(54) PERITONEAL DIALYSIS SYSTEM

(75) Inventors: Diego Mastalli, Biassono (CH); Alfio Quarteroni, St-Sulpice (CH); Paolo Zunino, Milan (IT)

(73) Assignee: Debiotech S.A., Lausanne (CH)

( * ) Notice: Subject to any disclaimer, the term of this patent is extended or adjusted under 35 U.S.C. 154(b) by 91 days.

(21) Appl. No.: 13/287,939

(22) Filed: Nov. 2, 2011

(65) Prior Publication Data

US 2012/0143124 A1  Jun. 7, 2012

Related U.S. Application Data

(62) Division of application No. 12/278,662, filed as application No. PCT/IB2007/050406 on Feb. 7, 2007, now abandoned.

(30) Foreign Application Priority Data

Feb. 8, 2006  (WO) .................. PCT/IB2006/050412

(51) Int. Cl.
*A61M 1/00*  (2006.01)

(52) U.S. Cl.
USPC .............................. 604/29; 600/301; 604/500

(58) Field of Classification Search
USPC ..................... 604/29, 500; 600/301
See application file for complete search history.

(56) References Cited

FOREIGN PATENT DOCUMENTS

EP  2381376 A1 * 10/2010 .............. G06F 19/00

* cited by examiner

*Primary Examiner* — Emily Schmidt
(74) *Attorney, Agent, or Firm* — Nixon & Vanderhye P.C.

(57) ABSTRACT

The invention relates to a method for prescribing a dialysis treatment comprising the following steps:
  collecting patient specific data,
  determining at least one target,
  defining a series of values of the type [V;t] which allow to achieve said target wherein V represents the volume of dialysate used and t the duration of treatment, based on said patient specific data,
  displaying said series of values on a map.
The invention also relates to a system using this method.

21 Claims, 24 Drawing Sheets

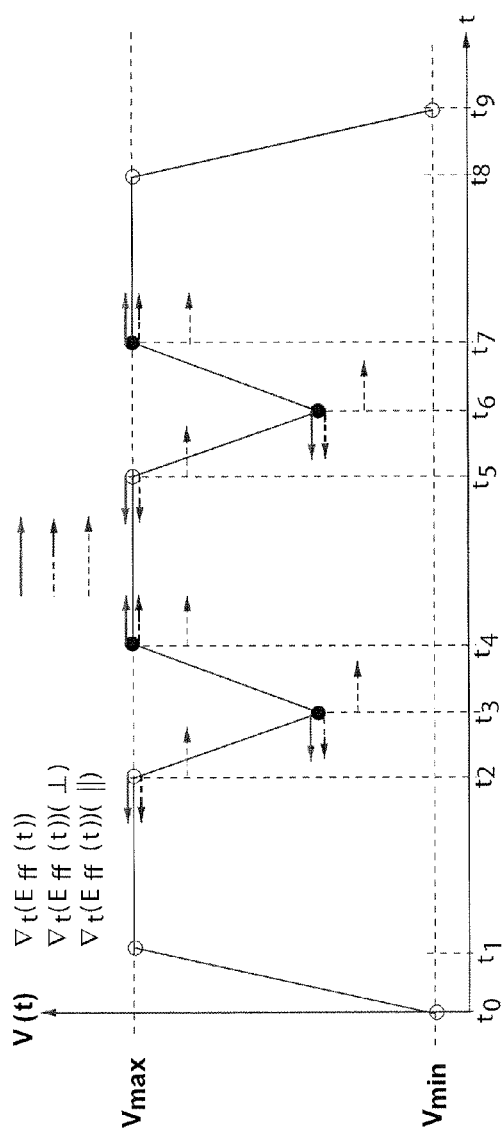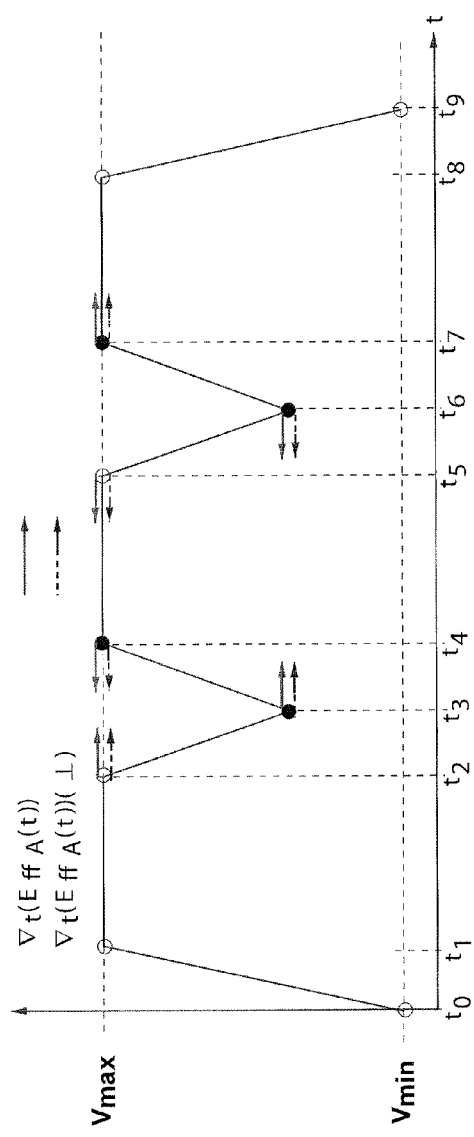

PERITONEAL DIALYSIS SYSTEM

This application a divisional of U.S. patent application Ser. No. 12/278,662, filed on 7 Aug. 2008, which is the U.S. national phase of International Application No. PCT/IB2007/050406, filed on 7 Feb. 2007, which designated the U.S. and claims priority to IB Application No. PCT/IB2006/050412, filed on 8 Feb. 2006, the entire contents of each of which are hereby incorporated by reference.

FIELD OF INVENTION

The present invention relates to a peritoneal dialysis system which can conduct a specific peritoneal dialysis treatment.

The invention also relates to a method for determining a peritoneal dialysis treatment which is specific for each patient.

STATE OF THE ART

During a peritoneal dialysis session a liquid, the so called dialysate, is introduced many times into the peritoneal cavity in order to exchange toxins and liquid with the blood. The exchange takes place through the net of capillaries within the peritoneal membrane.

Examples of standard treatments are:
APD (Automatic Peritoneal Dialysis),
CAPD (Continuous Ambulatory Peritoneal dialysis),
CCPD (Continuous Cycling Peritoneal Dialysis),
TPD (Tidal Peritoneal Dialysis).

All state of the art treatments are characterized by exchanges with fixed volumes and dwells. However, those treatments are not taking into account the permanent change of patient characteristics after each exchange cycle.

It would therefore be more efficient to have another treatment which better follow the changes of patient characteristics during a treatment.

DESCRIPTION OF THE INVENTION

The above cited problems are solved with the peritoneal dialysis system according to the invention which comprises pumping means, therapy data receiving means and processing means, said processing means being designed to process said therapy data and to impart a switching sequence to said pumping means. The system according to the invention is characterized by the fact that said processing means are furthermore designed to impart a specific exchange profile for each exchange cycle.

In other words, the system according to the invention is designed to vary the exchange cycles during the treatment in order to better match the patient characteristics in a dynamic way.

In the following text, the treatment according to the invention is called DPD for Dynamic Peritoneal Dialysis.

The variation of the exchange cycles can be done in varying the injected volume of liquid and/or the dwell times and/or the extracted volume of liquid.

DETAILED DESCRIPTION OF THE INVENTION

A more detailed description of the invention is presented below together with the following figures.

Figure 13:
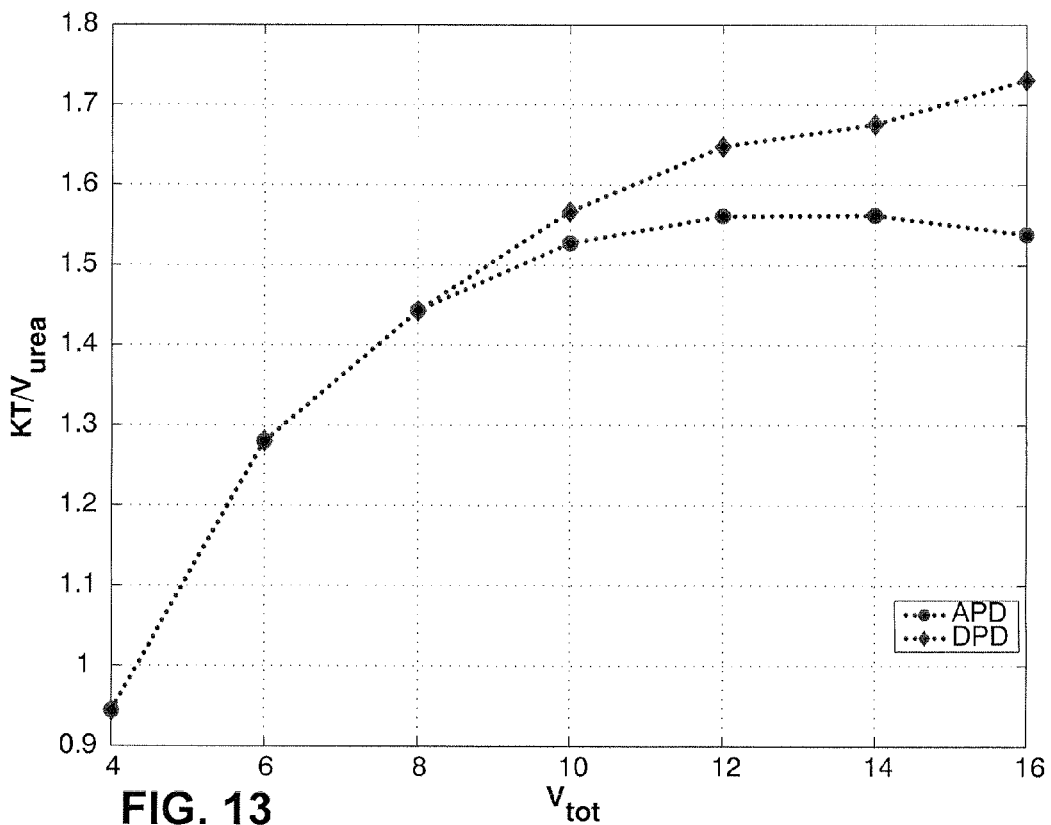
Figure 14:
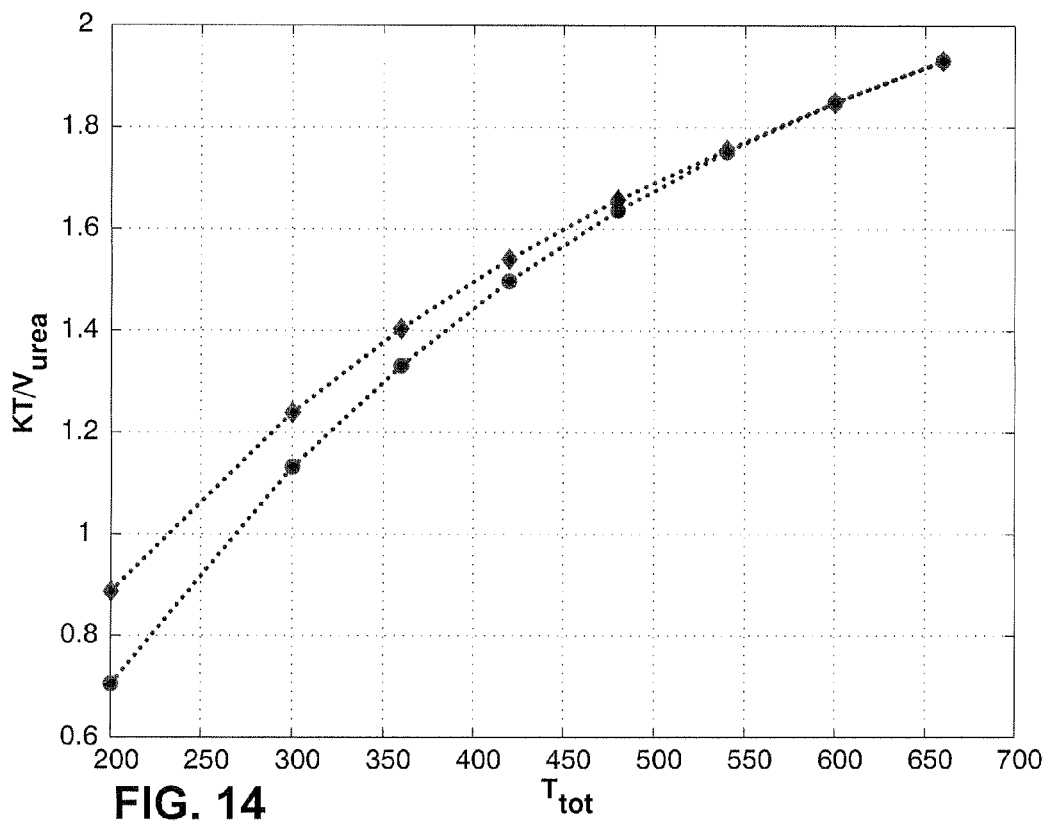
Figure 15:
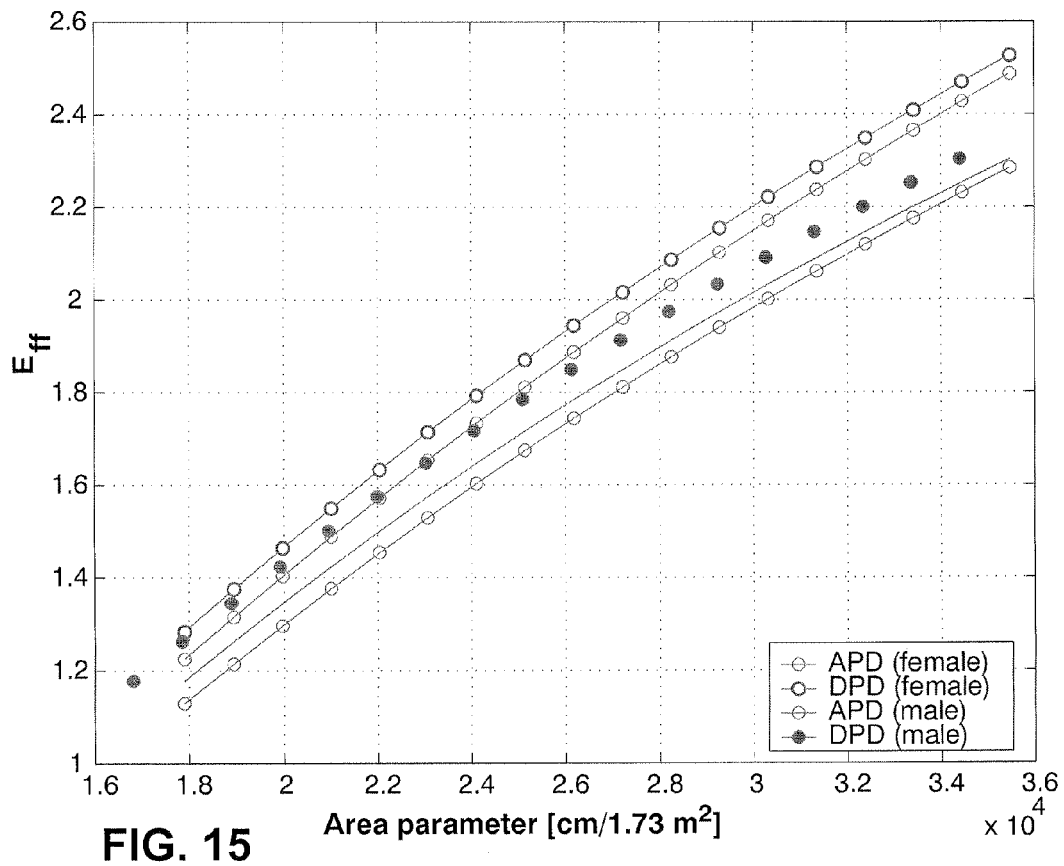
Figure 16:
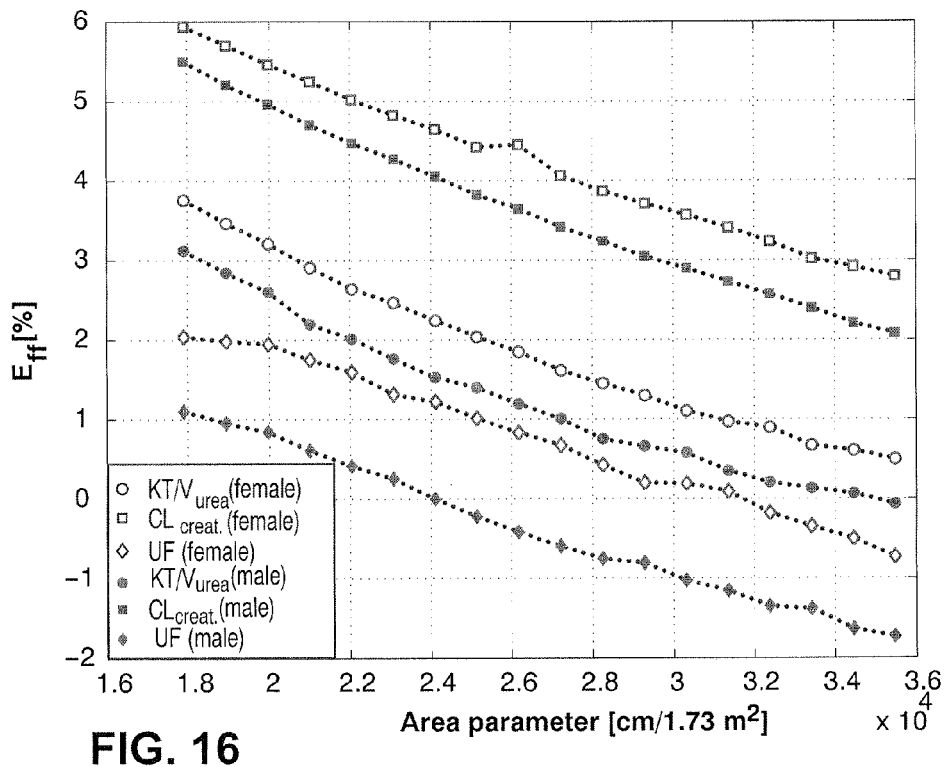
Figure 17A:
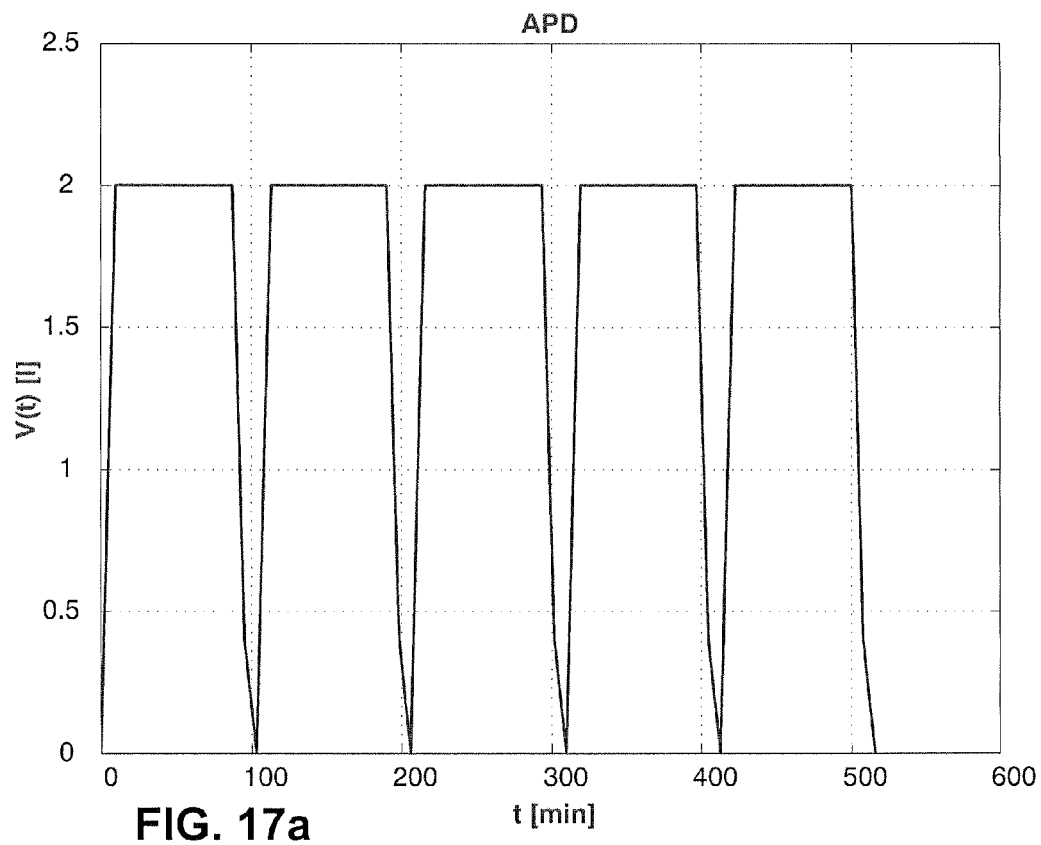
Figure 17B:
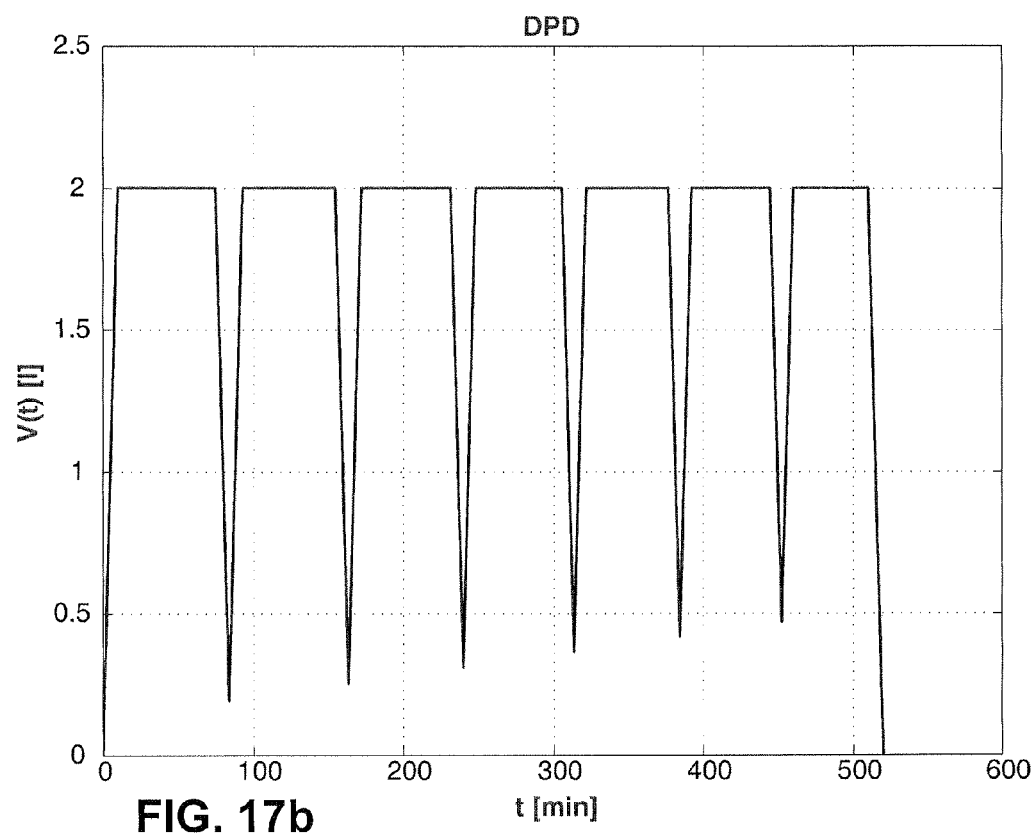
Figure 18:
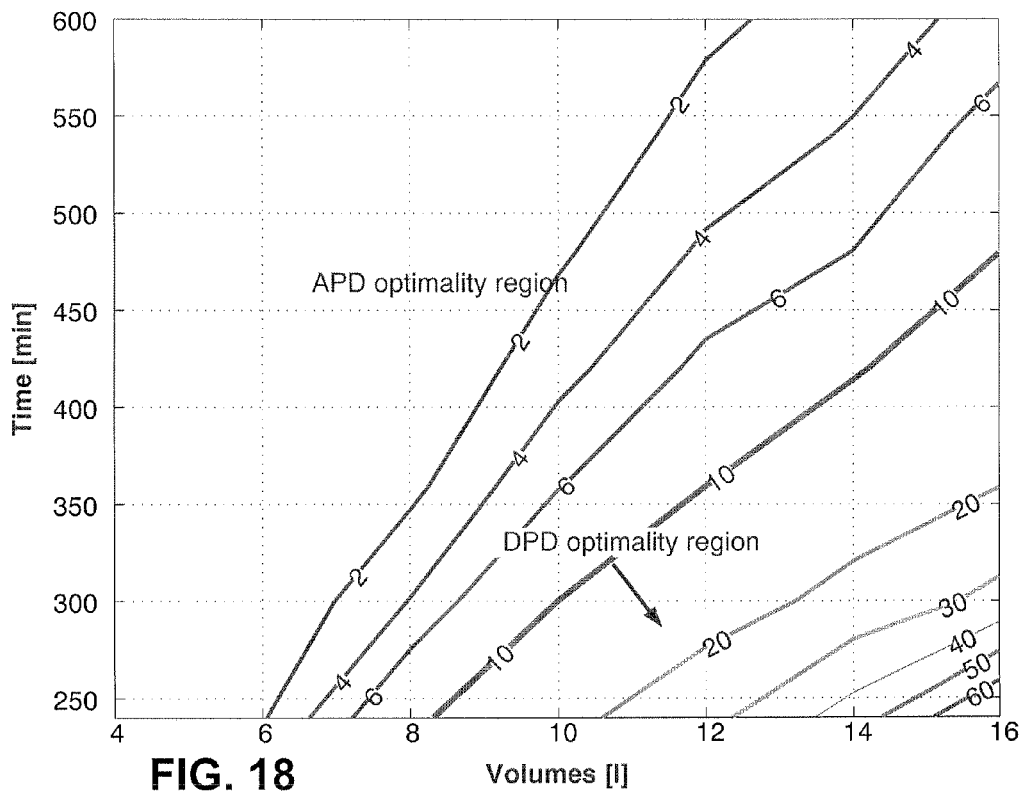
Figure 19:
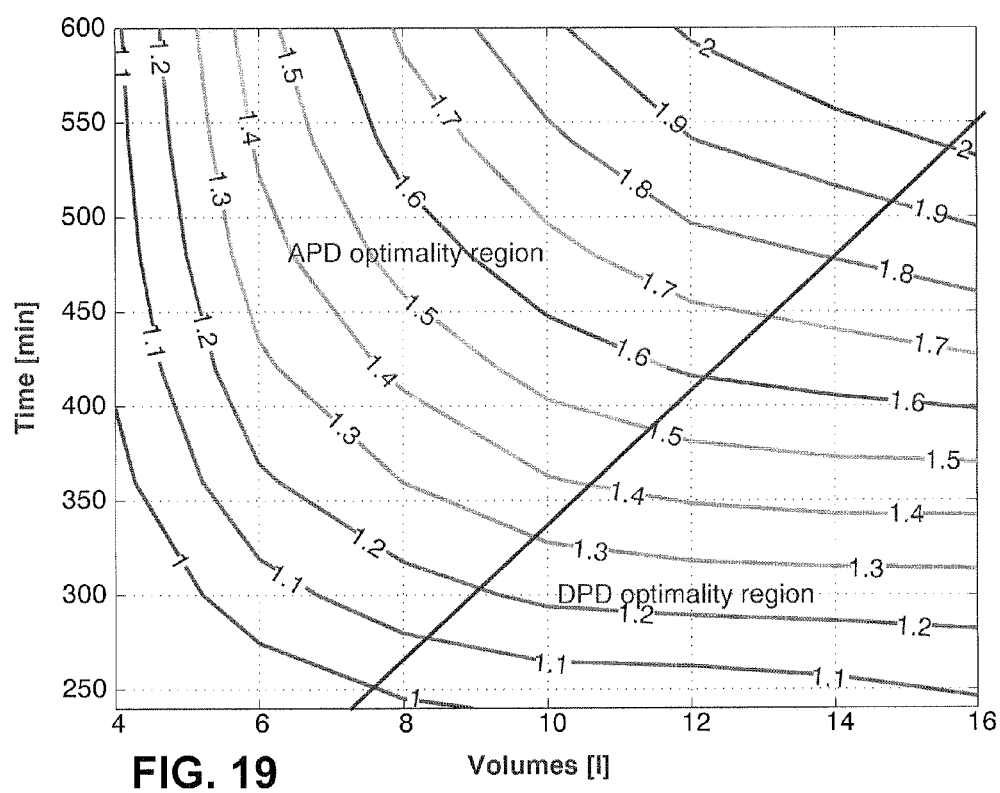
Figure 20:
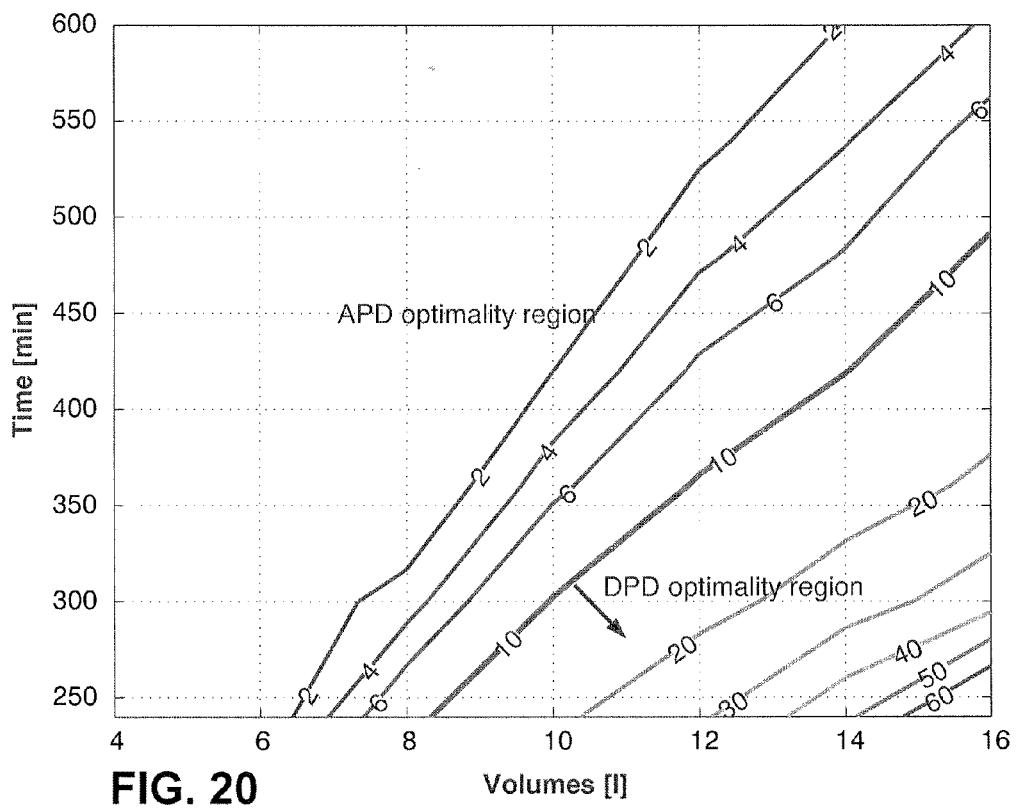
Figure 21:
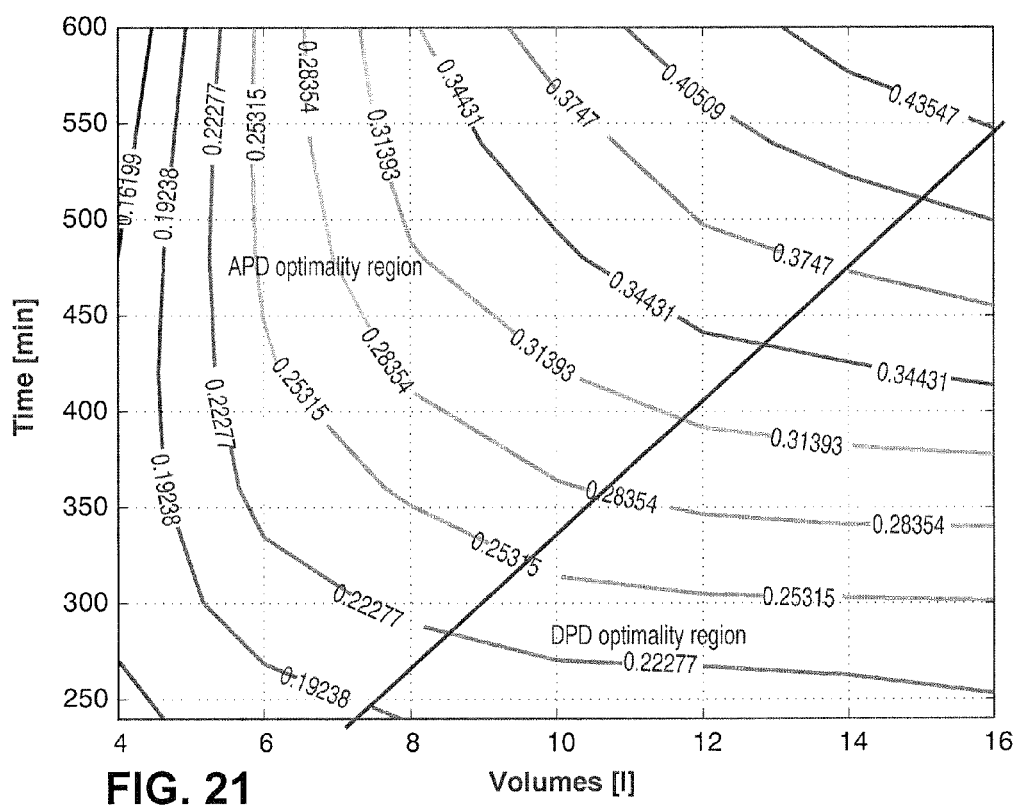
Figure 22:
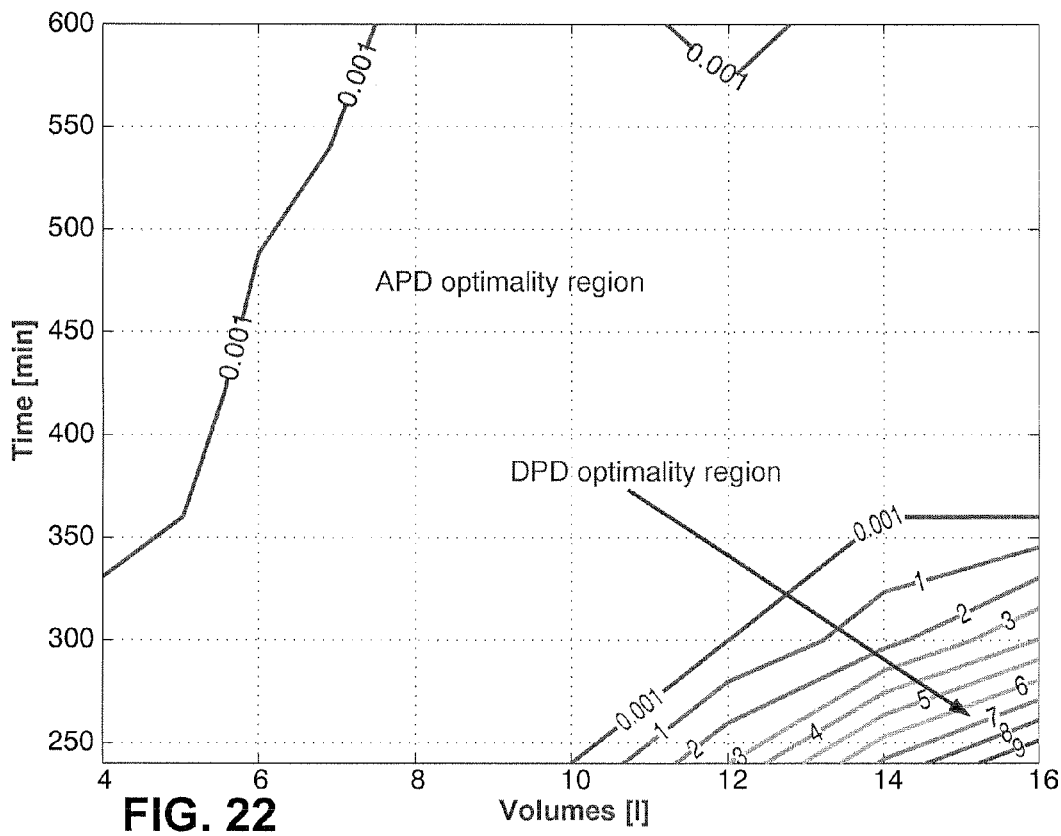
Figure 23:
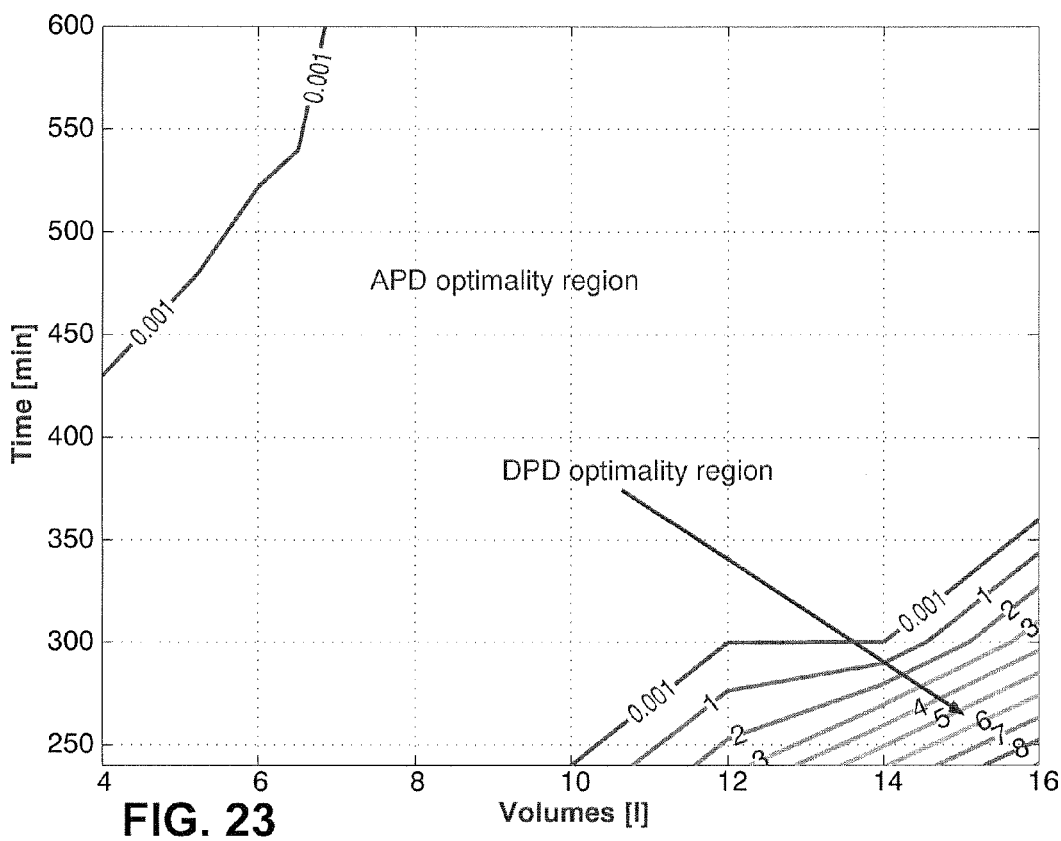
Figure 24:
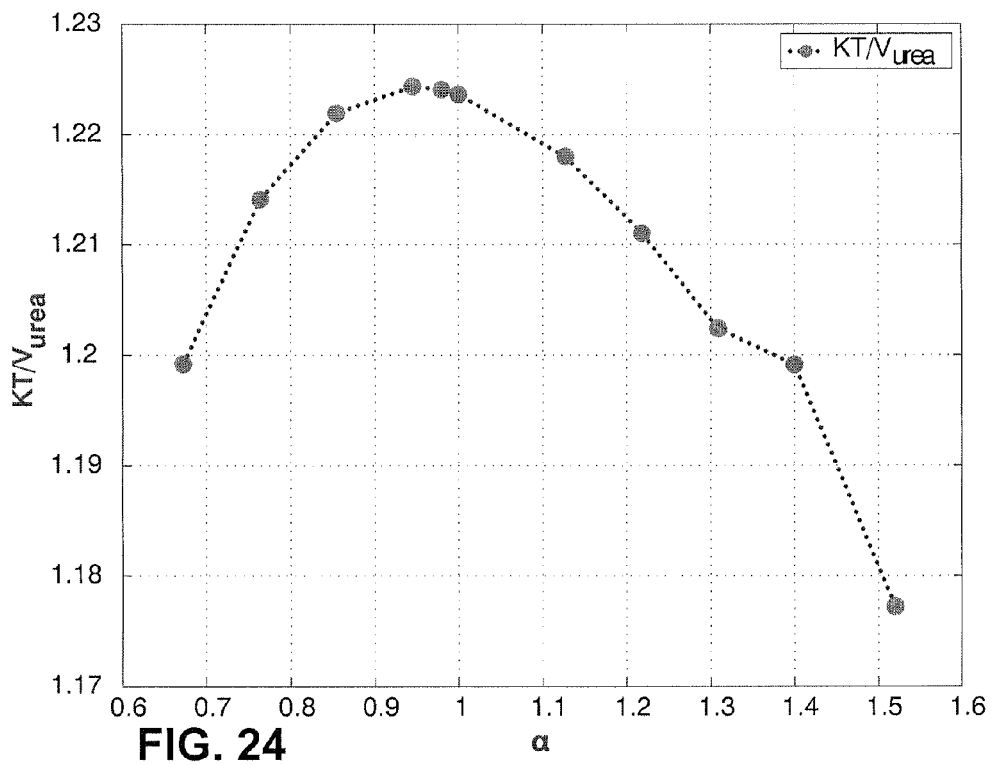
Figure 25:
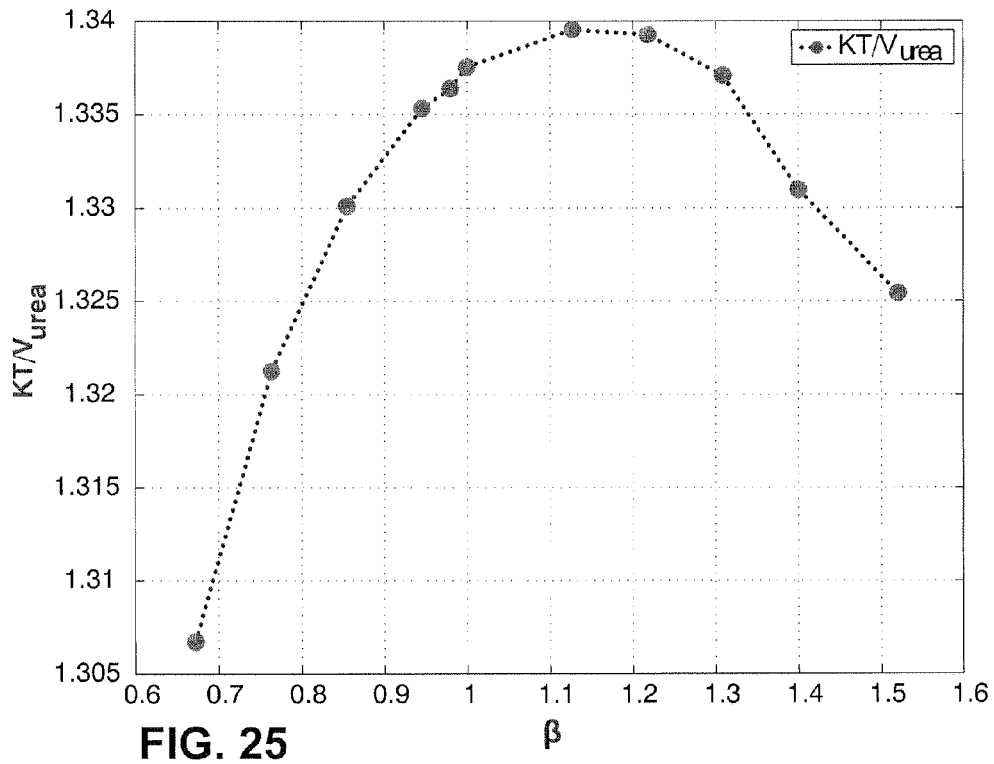
Figure 26:
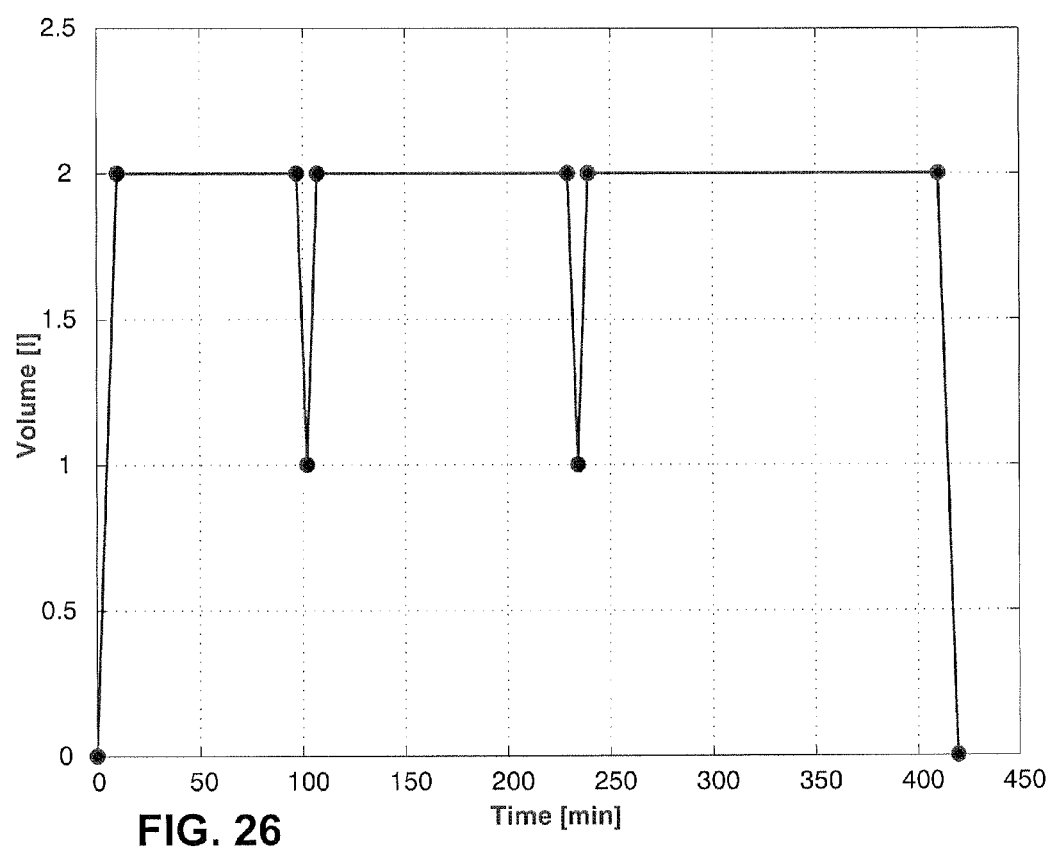
Figure 28A:
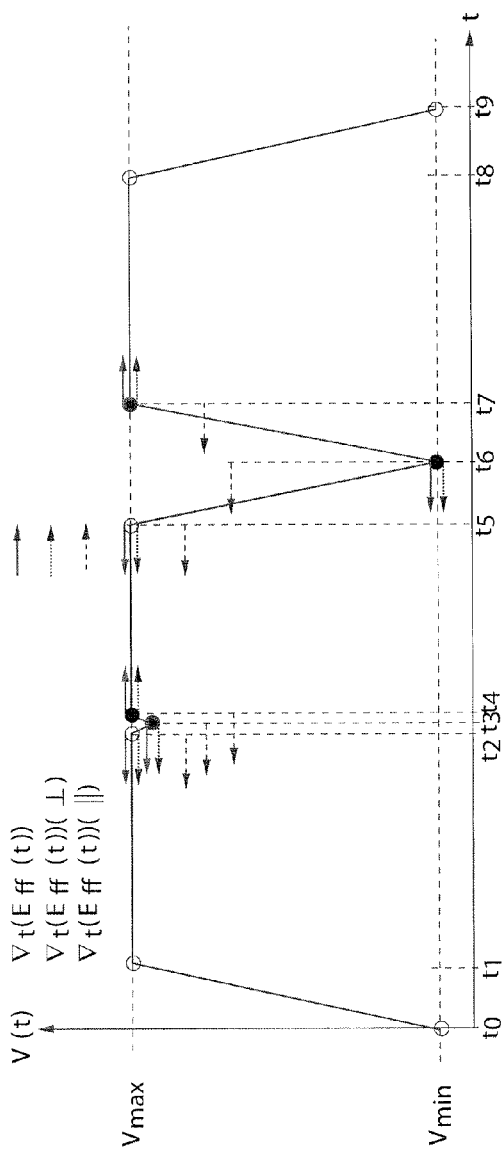
Figure 28B:
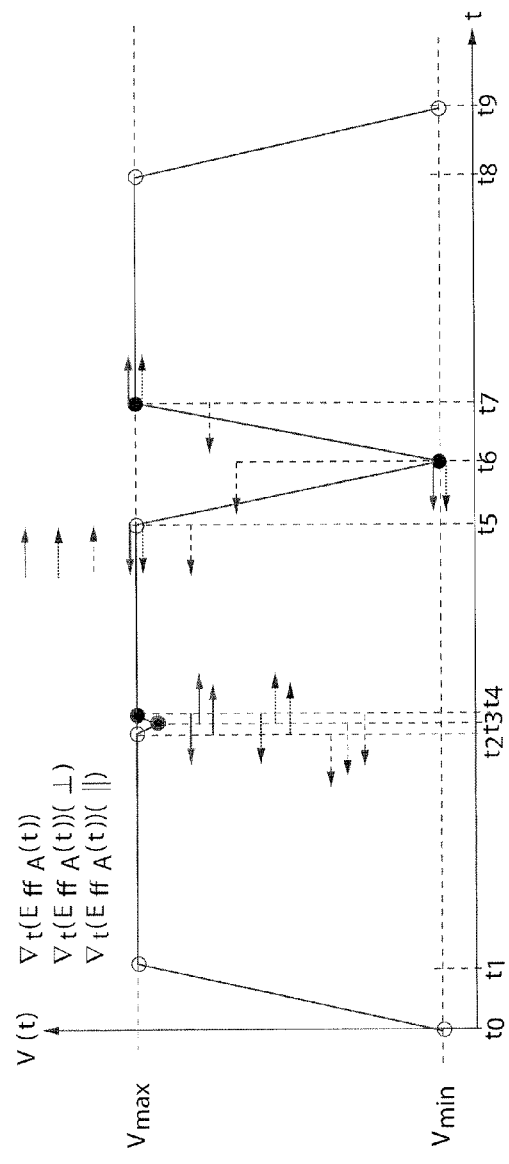
Figure 29:
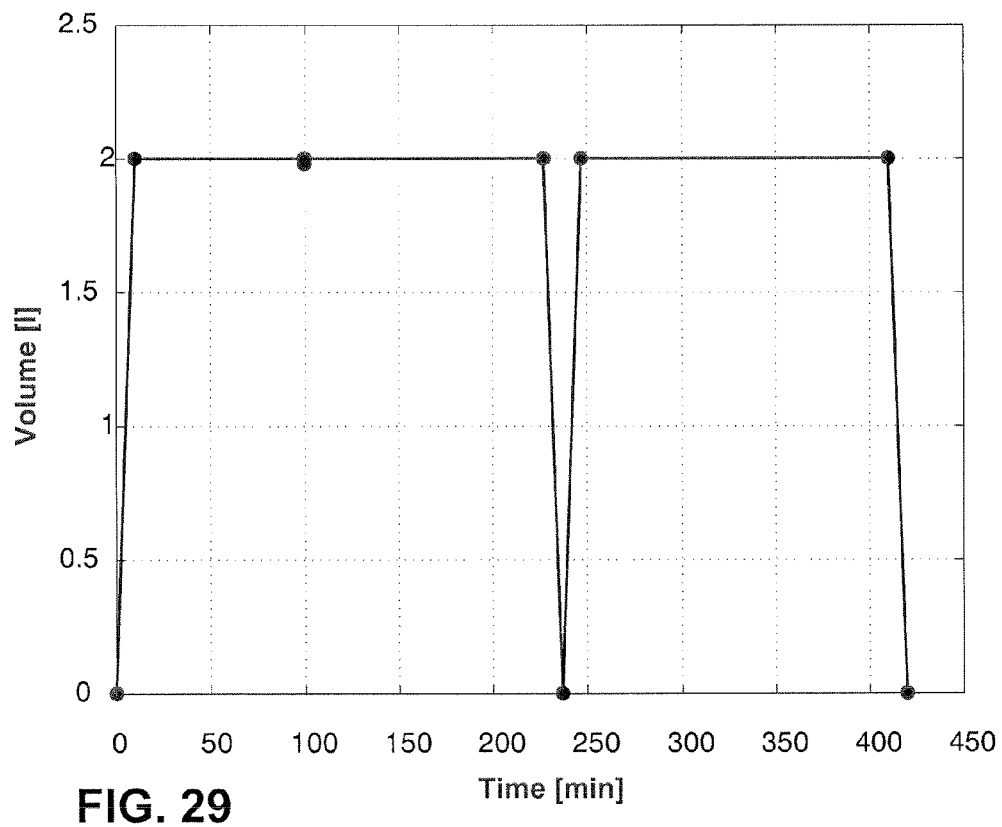
Figure 30:
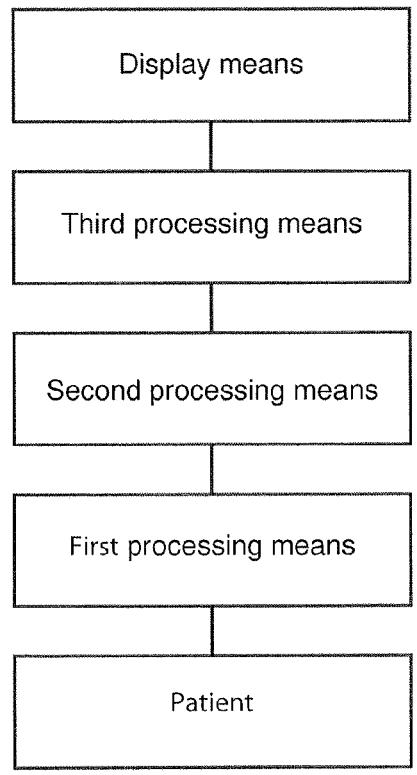

FIG. 13 shows influence of $V_{tot}$ on APD and DPD patterns.
FIG. 14 shows influence of $T_{tot}$ on APD and DPD patterns.
FIG. 15 shows the APD performance and the DPD optimized performances.
FIG. 16 shows the APD performance and the DPD optimized performances.
FIGS. 17a and 17b shows APD and DPD patterns.
FIG. 18 shows a map of a system according to the invention with optimal KT/Vurea increase (%) with respect to APD. In such graph, the KT/Vurea is indicated with isolines, each of them representing a fixed result obtained for different peritoneal dialisys volumes and treatment times.
FIG. 19 shows a map of a system according to the invention with KT/Vurea as target.
FIG. 20 shows a map of a system according to the invention with optimal UF increase (%) with respect to APD.
FIG. 21 shows a map of a system according to the invention with optimal UF as target.
FIG. 22 shows a map with optimal KT/Vurea increase (%) with respect to APD applying the ideal pump model.
FIG. 23 shows a map with optimal KT/Vurea increase (%) with respect to APD applying the ideal pump model.
FIG. 24 shows KT/Vurea represented as function of $\alpha$.
FIG. 25 shows KT/Vurea represented as function of $\beta$.
FIG. 26 shows the PD profile chosen as starting point of the optimization process.
FIGS. 27a and 27b shows sensitivity of $E_{f\!f}(a)$ and $E_{f\!f_A}(b)$ with respect to the switching sequence and their components (perpendicular ($\perp$) and parallel ($\|$) to the inequality constraints). The figure represents the information obtained at the first iteration.
FIGS. 28a and 28b shows sensitivity of $E_{f\!f}(a)$ and $E_{f\!f_A}(b)$ with respect to the switching sequence and their components (perpendicular ($\perp$) and parallel ($\|$) to the inequality constraints). The figure represents the information obtained at the last iteration.
FIG. 29 shows the PD profile obtained after 10 iterations of the optimization algorithm.
FIG. 30 is a block diagram of a peritoneal dialysis prescription system according to the present invention comprising a first processing means for entering patient specific data, a second processing means for selecting a target, a third processing means for defining a series of values of the type [V;t] and a display means adapted for displaying said series of values on a map.

Figure 1:
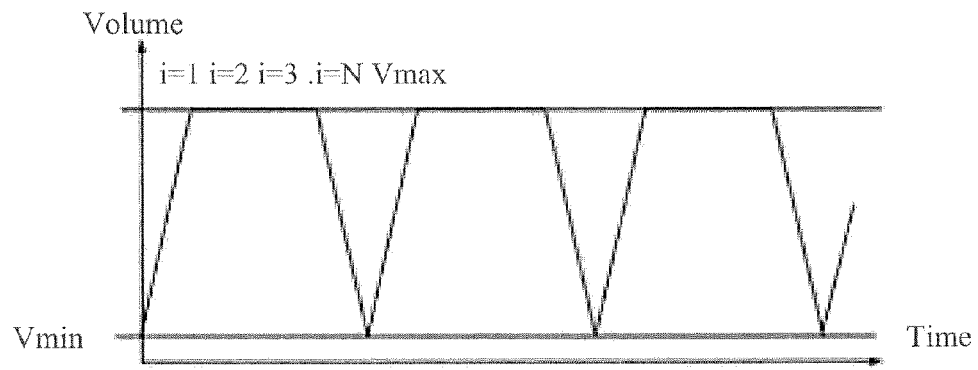
FIG. 1 illustrates the volume exchange with the peritoneal cavity.

Let us introduce the notation that will be used in relation with the DPD pattern. We remind that the injection-dwell-extraction pattern in peritoneal dialysis (PD) is made by several cycles i=1, ..., N (see FIG. 1). The Vmax and Vmin in FIG. 1 represent respectively the maximum volume that can be introduced in the peritoneal cavity and the minimum volume reachable. In each cycle some fresh dialysate is injected (DVi), and extracted from the patient after a given dwell time (TDi). We refer to FIG. 2 for an explanation of the notation. The standard therapies nowadays in use APD, CAPD, CCPD, TPD etc. . . . , have a common property: the dwell times DTi and the injected volumes DVi are fixed with respect the number of cycle i=1; . . . ; N. It means that:

$$DT(1)=DT(2)=\ldots=DT(N)$$

$$DV(1)=DV(2)=\ldots=DV(N)$$

Figure 2:
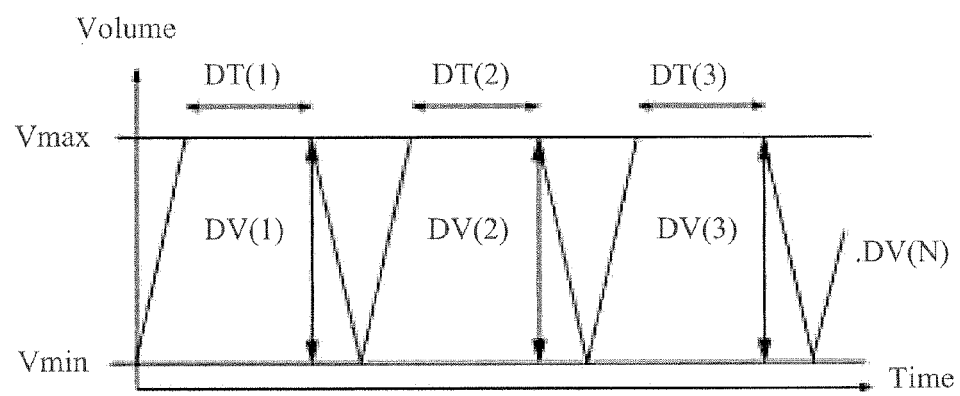
FIG. 2 illustrates a state-of-the-art therapy
Figure 3:
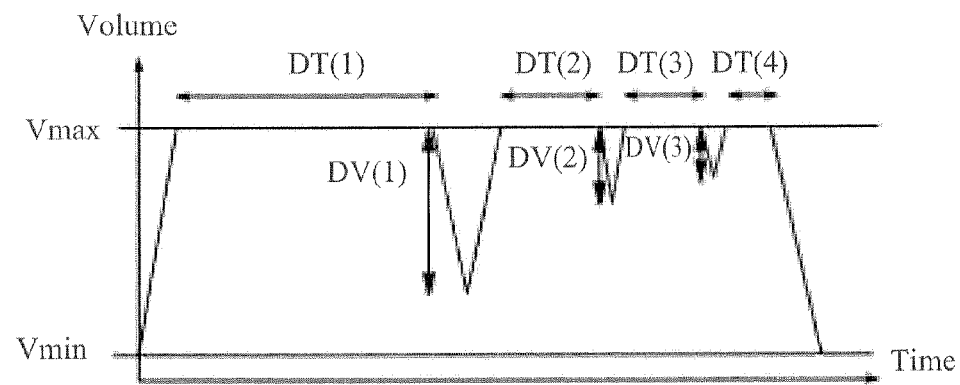
FIG. 3 illustrates a DPD treatment according to the invention.

This is just the case represented in FIG. 2. It is obvious that by this way the standard PD treatments are somewhat rigid because there is no possibility to get $DT(1) \neq DT(2) \neq \ldots \neq DT(N)$ and or $DV(1) \neq DV(2) \neq \ldots \neq DV(N)$. Conversely, the DPD treatments provide this possibility and guarantee more flexibility. We refer to FIG. 3 as example of DPD. The reader should recognize easily the variability in dwell times and volumes that distinguish DPD with respect standard therapies by a comparison of FIGS. 2 and 3.

In order to build a DPD pattern we consider a set of input data concerning the therapy.

Preferably we consider as input the total therapy time ($T_{tot}$), the total dialysate volume available for the peritoneal dialysis session ($V_{tot}$), the flow rate of the pumping means (q), the maximum dialysate volume that can be contained in the peritoneal cavity ($V_{max}$), the minimum dialysate volume reachable in the peritoneal cavity ($V_{min}$) and the number of cycles of the therapy (N).

The DPD method provides the injection-dwell-extraction pattern taking into account a set of constraints:
the therapy begin filling the peritoneal cavity up to Vmax,
the therapy must not be longer than the fixed total time Ttot, $$\sum_{i=1}^{N} TD(i) = T_{tot} - 2\frac{V_{tot}}{q}$$

the total dialysate volume injected must be equal to the total amount Vtot available, $$\sum_{i=1}^{N-1} VD(i) = V_{tot} - (V_{max} - V_{min})$$

the dwell times must be positive, $$TD(i)>0, i=1,\ldots,N$$

the volume of dialysate into the peritoneal cavity must respect the lower and the upper bounds Vmin and Vmax $$0<DV(i) \leq V_{max} - V_{min}, i=1,\ldots,N-1$$

the therapy end emptying the peritoneal cavity from Vmax to Vmin,
Nmin is the minimum number of cycles needed to use the dialysate available: Nmin=ceil(Vtot=(Vmax/Vmin)).

Based on the previous input data and constraints the DPD strategy provides the injection-dwell-extraction through the following iterative relations. The first set is used to choose the dwell times T D(i) of the DPD pattern as follows:
where, $$\begin{cases} TD(i+1) = (\alpha + \gamma i)TD(i), i=1,\ldots,N-1 \\ TD(1) = \dfrac{T_{tot} - 2\dfrac{V_{tot}}{q}}{1 + \sum_{j=1}^{N-2} \prod_{i=1}^{j} \alpha + \gamma i} \end{cases}$$

$\alpha$ is the parameter which fix a base for the ratio T D(i+1)/T D(i), $\beta$ is the parameter which allows to change the ratio T D(i+1)/T D(i) with respect the number of the cycle,
TD(1) is computed to respect the total therapy time Ttot
The second set is used to choose the volumes injected DV(i) of the DPD pattern as follows:
where, $$\begin{cases} DV(i+1) = (\beta + \delta i)DV(i), i=1,\ldots,N-2 \\ DV(1) = \dfrac{V_{tot}}{1 + \sum_{j=1}^{N-2} \prod_{i=1}^{j} \beta + \delta i} \end{cases}$$

$\beta$ is the parameter which fix a base for the ratio DV(i+1)=DV(i),
$\delta$ is the parameter which allows to change the ratio DV(i+1)=DV(i) with respect the number of the cycle
V D(1) is computed to respect the total dialysate volume Vtot available. If $\gamma=0$, $\alpha=1$ we obtain TD(i+1)=TD(i) and If $\delta=1$, $\beta=1$ we obtain DV(i+1)=DV(i). This parameters set up allows to obtain standard treatments by the DPD methodology.

In order to guarantee the execution of the DPD pattern to pumping means the outputs produced are:
the dwell sequence T D(i); i=1; . . . ; N,
the volume sequence DV(i); i=1; . . . ; N−1,
the switching sequence for the pumping means execution, t0=0;

tk+1 =tk+DT(k);k=0; . . . ;3N+1 where DT (k) represent the time needed in each cycle for the injection phase, the dwell and the extraction phase.

Numerical Results and Applications

We would like to offer an overview of the applications of the PD kinetic models, and the methods introduced so far for the study of the solute dynamics through the peritoneal membrane. We are considering several numerical simulations obtained applying these models, with physiological parameters, for specific patients. Then, we discuss the relevance of the results from the physical point of view. Indeed, our goal is to show that the application of mathematical models can help the biomedical research because it enhances the understanding of complex physical phenomena. More specifically, we try to explain how the dynamics of solutes is influenced by the therapy profile and the pump injecting and extracting the dialysate. Nevertheless, since we consider a space lumped model which is a representation of an excerpt of the reality, it is possible to have a discrepancy between measurements and computed data.

The first part of this description deals with the PD optimal control problem approach based on the parametrization of the control function u(t). The second part is devoted to investigate different aspects involved in the PD process to better understand the behavior of the system. The third part is devoted to switched systems. Finally we set up a method to minimize the glucose exposure and to optimize the PD process by variable glucose concentration in the dialysate. All the numerical simulations presented here have been carried out by a computer program, in C language named ChronoDial Manager developed in collaboration with DebioTech and Dr. Paolo Zunino.

A Consistency Numerical Test on Glucose

To check the consistency of our numerical results with respect to the reality we propose a first test which uses as input the glucose concentration in the dialysate. Glucose concentration can be exploited to drive the exchange of chemical and fluid through the peritoneal membrane. Precisely, we expect that a growing glucose level would produce a better blood purification in terms of chemical extraction and fluid removal. This is why we check the behavior of the system according to the dialysate glucose level focusing our attention on urea, creatinine extraction and fluid removal. Moreover, we compute the amount of glucose absorbed by the patient during the PD process. Let us consider two patients a; b belonging to the classes HA and LA, respectively. We assume that all the patient dependent parameters are obtained by the identification process based on a PDC test. All the numerical results are obtained using the three pore model.

The three pore model still considers one compartment accounting for the body (b), and one for the peritoneal cavity of the patient denoted by the index (d) that are separated by a semipermeable membrane that represents the peritoneal membrane. The procedure to derive the three pore model is similar to that used for the Pyle-Popovich model. In fact, based on the same assumptions of the Pyle-Popovich model, the interaction between the two compartments is governed by the Kedem-Katchalsky equations prescribing the flux of solvent $J_v$ and of solute $J_{s,i}$ across the membrane. Moreover we assume that the membrane is crossed by straight cylindrical channels representing the pores. The pores can be subdivided in three classes that we denote by the index j=1; : : : , 3, depending on their size. Let us introduce $L_p$; $P_i$, the hydraulic conductivity and permeability of the membrane. Let us denote with $L_{p,j}$; $P_{i,j}$ the corresponding quantities associated to the $j^{th}$ class of pores. Furthermore let $\sigma_{i,j}$ be the reflection coefficients of the membrane relative to $j^{th}$ class of pores with respect to the $i^{th}$ solute. The Kedem-Katchalsky equations read as follows, $$J_{v,j} = L_{p,j}\left(\Delta p - \sum_{i=1,N}\sigma_{i,j}\Delta\pi_i\right), J_v = \sum_{j=1,M} J_{v,j},$$

$$J_{s,i,j} = P_{i,j}\Delta c_i + J_{v,j}(1-\sigma_{i,j})f_i(c_{b,i}, c_{d,i}), J_{s,i} = \sum_{j=1,M} J_{s,i,j},$$

where $f_i(c_b;i; c_d;i)$ is the average concentration inside the membrane. The total flux of solvent $J_v$ is the sum of the contributions of each class of pores. The pressure is, on the other hand, split in two parts, the static pressure $\Delta p$ and the osmotic pressure $\Delta\pi$ due to the solutes. By applying the definitions of $J_v$ and $J_{s,i}$ and the mass conservation law, we end up with a system of 2N+2 equations that describe the rate of change of the unknowns $V_b$, $V_d$, $V_b c_{b,i}$, $V_d c_{d,i}$, i=1; : : : ; N by means of expressions derived from the equations below. If we denote the rate of change of the variables at hand with the symbols $$\frac{d}{dt}V_b, \frac{d}{dt}V_d, \frac{d}{dt}V_b c_{b,i}, \frac{d}{dt}V_d c_{d,i}),$$

we have, $$\begin{cases} \frac{d}{dt}V_b(t) = -\sum_{j=1}^{3}\left\{L_{p,j}\cdot S\cdot\left[(p_b-p_d)-RT\sum_{i=1}^{N}\sigma_{i,j}(c_{b,i}(t)-c_{d,i}(t))\right]\right\}+g_w-s_w+J_{v_l} \\ \frac{d}{dt}V_d(t) = \sum_{j=1}^{3}\left\{L_{p,j}\cdot S\cdot\left[(p_b-p_d)-RT\sum_{i=1}^{N}\sigma_{i,j}c_{b,i}(t)-c_{d,i}(t))\right]\right\}+u(t)-J_{v_l} \\ \frac{d}{dt}(V_b(t)c_{b,i}(t)) = -\sum_{j=1}^{3}\{P_{i,j}(c_{b,i}(t)-c_{d,i}(t))+J_{v,j}(c_{b,i}(t)-c_{d,i}(t))(1-\sigma_{i,j})f(c_{b,i}(t)-c_{d,i}(t))_i\}\cdot S+g_i+Kr_i\cdot c_{b,i} \\ i=1,\ldots,N \\ \frac{d}{dt}(V_d(t)c_{d,i}(t)) = \sum_{j=1}^{3}\{P_{i,j}(c_{b,i}(t)-c_{d,i}(t))+J_{v,j}(c_{b,i}(t)-c_{d,i}(t))(1-\sigma_{i,j})f_i(c_{b,i}(t)-c_{d,i}(t))\}\cdot S \\ i=1,\ldots,N \end{cases}$$

where S represents the effective surface of the peritoneal membrane, gi represents the generation rate of the $i_{th}$ molecule inside the body, $Kr_i$ represents the residual renal function and u(t) is a source term that takes into account the volume of fluid that is periodically injected and extracted from the peritoneal cavity. The quantities $J_{v_l}$ and $s_w$ are the other indicators of the physiological behavior of the human body, the lymphatic flow rate absorption and the residual renal function for $H_2O$, respectively.

Figure 4:
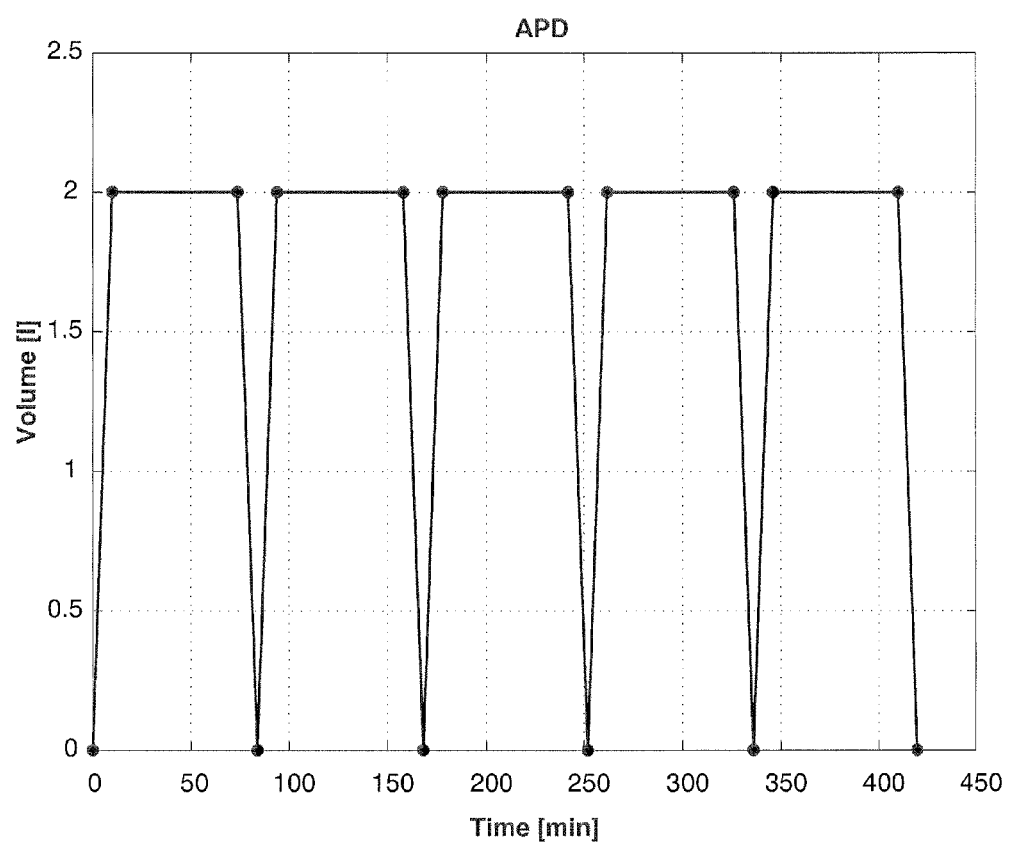
FIG. 4 shows a APD therapy corresponding to the data given in (1).

Moreover, we consider a standard APD that is characterized by the following parameters:

$T_{tot}$=420[min], $V_{tot}$=10[l], $V_{max}$=2.001[l], $V_{min}$=1[ml], $N$=5, (1)

where N denotes the number of cycles included in the PD therapy. FIG. 4 shows the APD profile determined by (1).

To start with we consider the patient a for which we carry out a series of numerical simulations.

In the first column of table 1 we report different glucose concentration in the dialysate and in the other columns we show the corresponding results related to the extraction of urea, creatinine and the ultrafiltration level followed by the glucose absorption.

TABLE 1

Numerical results related to patient a.
patient a, type HA

| glucose [%] | urea [g] | creatinine [g] | UF [l] | glucose absorption [g] |
|---|---|---|---|---|
| 1.36 | 5.351 | 0.160 | 0.207 | 46.153 |
| 1.56 | 5.423 | 0.163 | 0.318 | 53.292 |
| 1.76 | 5.497 | 0.166 | 0.430 | 60.248 |
| 1.96 | 5.572 | 0.169 | 0.542 | 67.140 |
| 2.16 | 5.647 | 0.172 | 0.657 | 73.850 |
| 2.27 | 5.689 | 0.174 | 0.719 | 77.587 |
| 2.47 | 5.765 | 0.177 | 0.833 | 84.323 |
| 2.67 | 5.841 | 0.181 | 0.946 | 91.002 |
| 2.87 | 5.918 | 0.184 | 1.061 | 97.625 |
| 3.07 | 5.995 | 0.188 | 1.176 | 104.186 |
| 3.27 | 6.073 | 0.191 | 1.291 | 110.701 |
| 3.47 | 6.152 | 0.195 | 1.406 | 117.166 |
| 3.67 | 6.231 | 0.198 | 1.522 | 123.582 |
| 3.86 | 6.307 | 0.201 | 1.633 | 129.565 |

By inspecting table 1 we conclude that given a therapy (1), the blood purification improves as far as the glucose concentration increases. This is consistent with the behavior expected and observed in reality. We would like to show what kind of dependence relates the PD efficiency and the input. Let us repeat the same results for each of the columns of table 1 in FIGS. 5a-5b and 6a-6b.

Figure 5A:
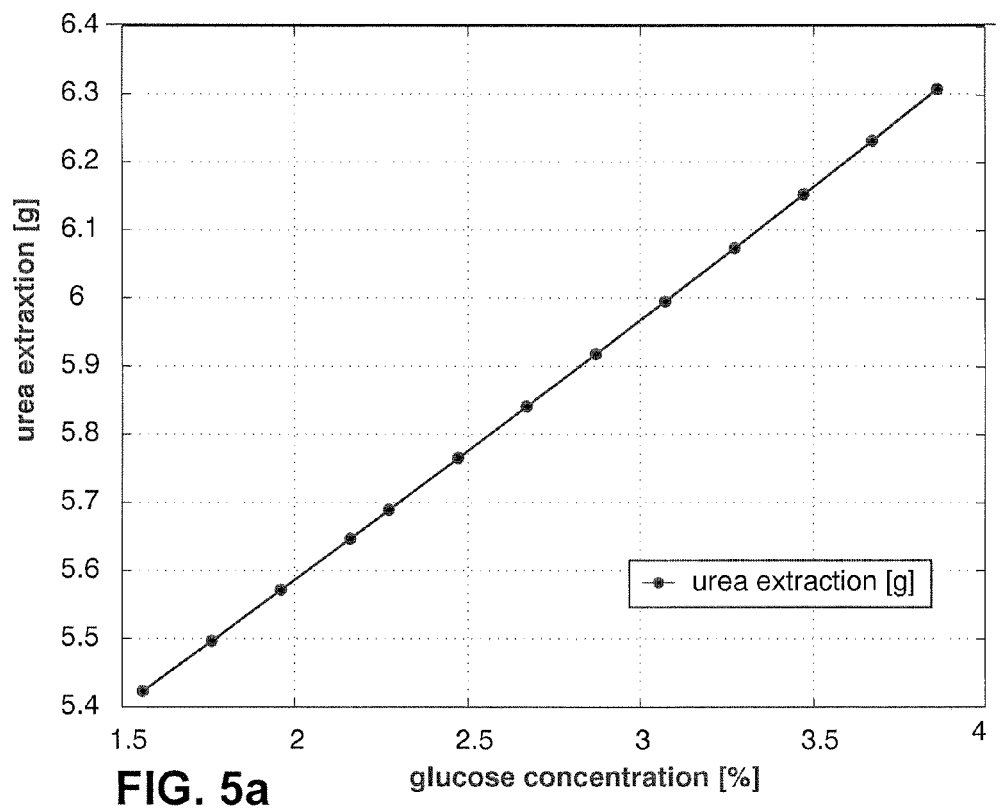
FIGS. 5a and 5b shows urea extracted (a) and creatinine extracted (b) during the APD as function of the dialysate glucose concentration.
Figure 5B:
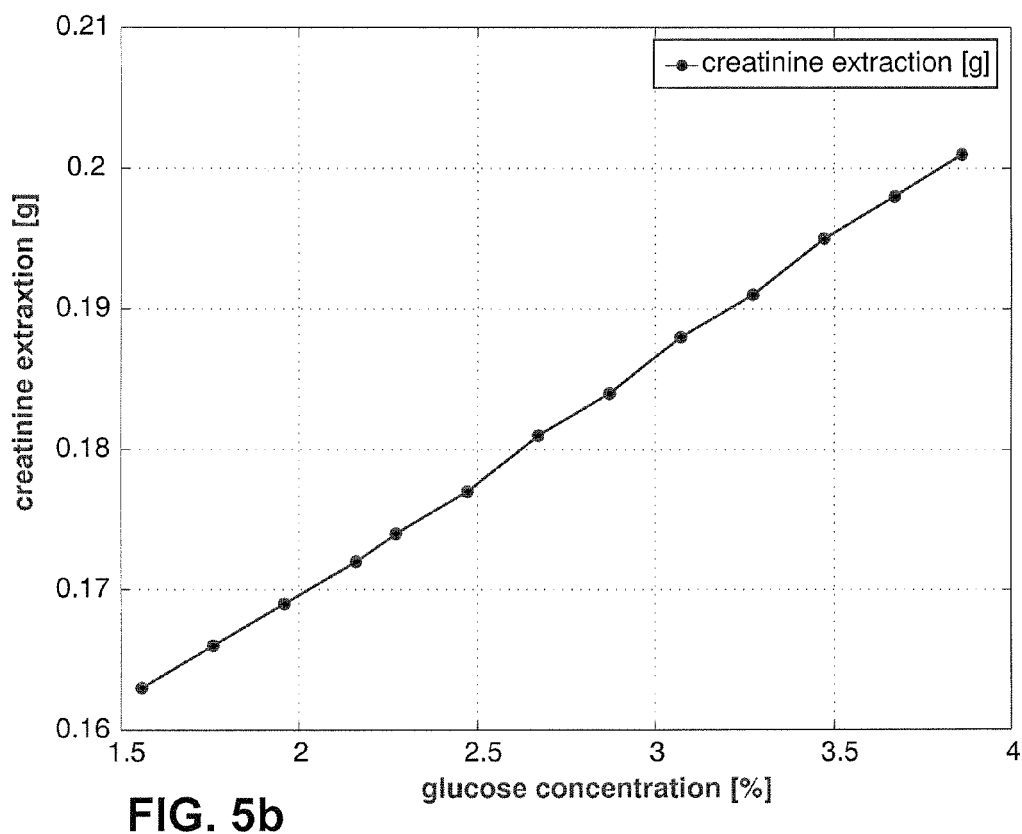
Figure 6A:
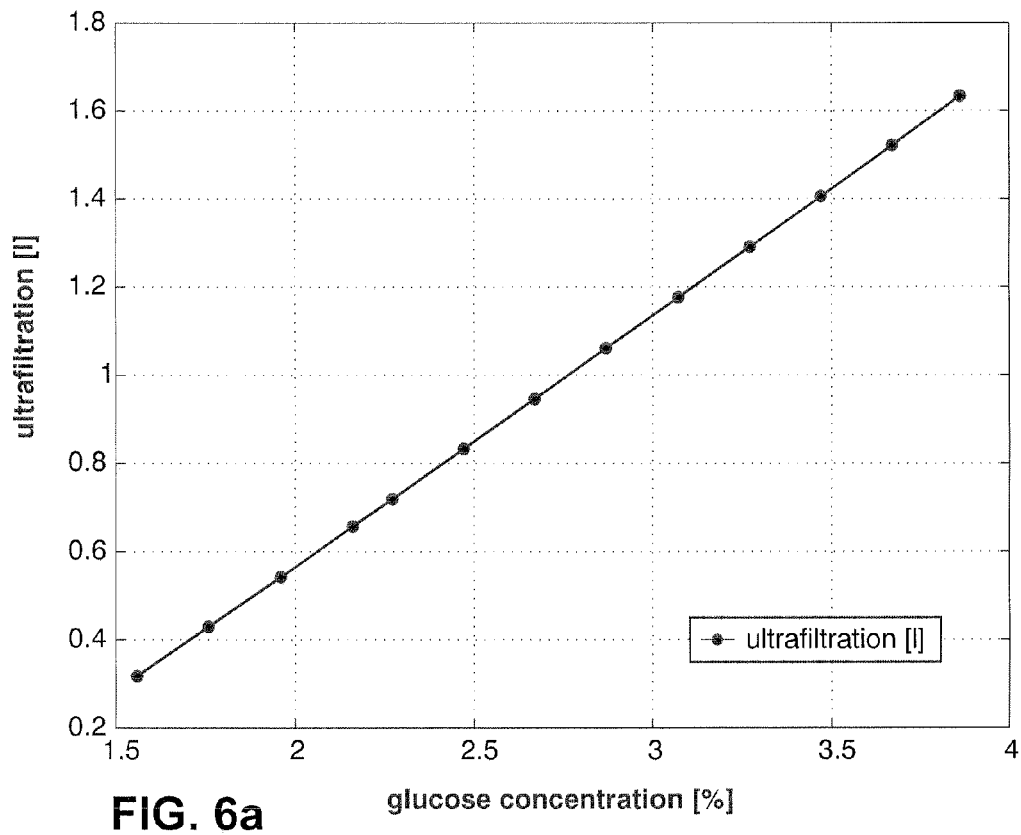
FIGS. 6a and 6b shows ultrafiltration (a) and glucose absorption (b) during the APD as function of the dialysate glucose concentration.
Figure 6B:
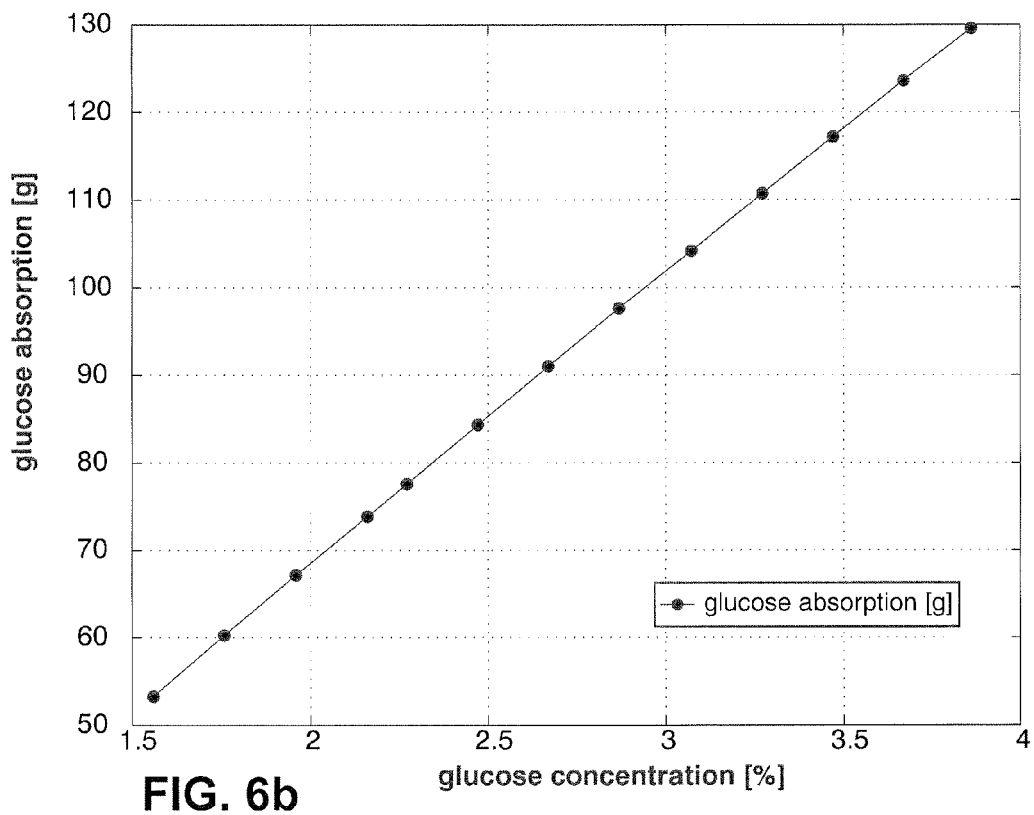
Figure 7A:
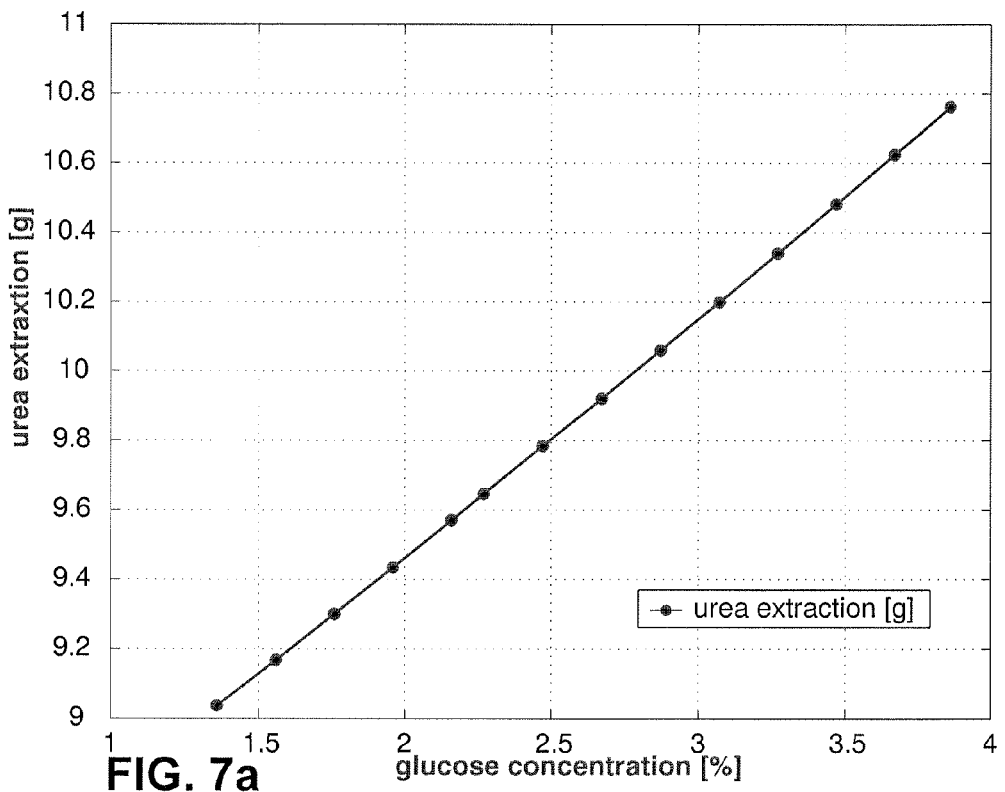
FIGS. 7a and 7b shows the urea extracted (a) and the creatinine extracted (b) during the APD as function of the dialysate glucose concentration.
Figure 7B:
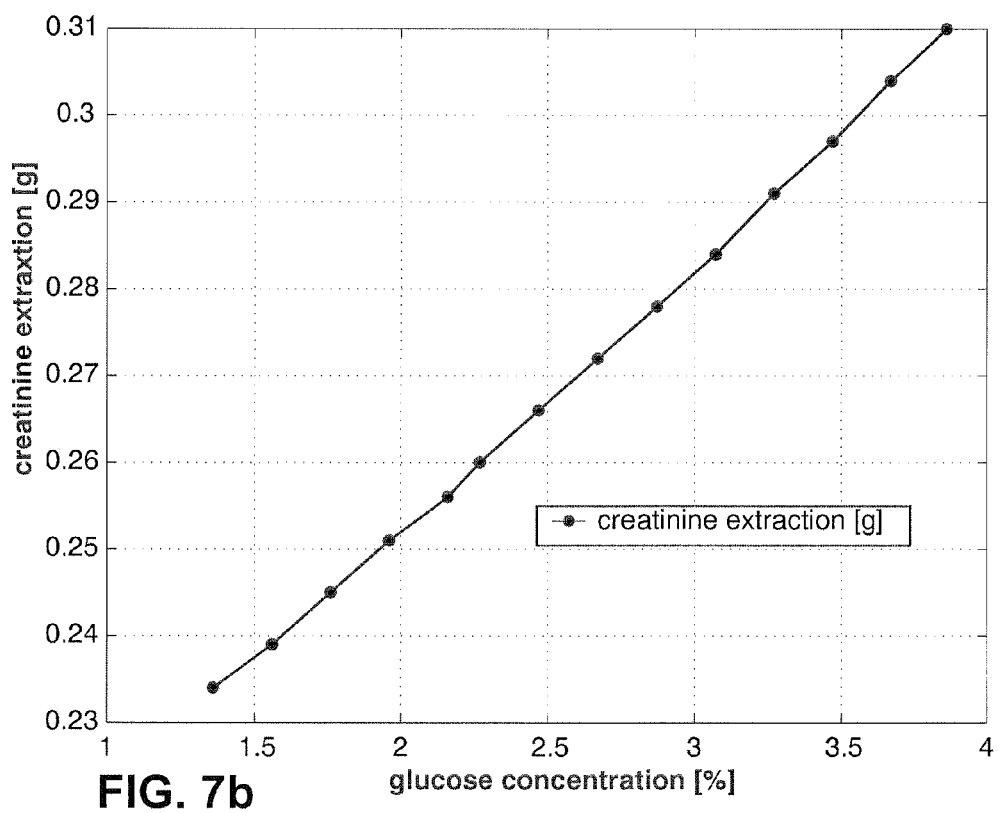
Figure 8A:
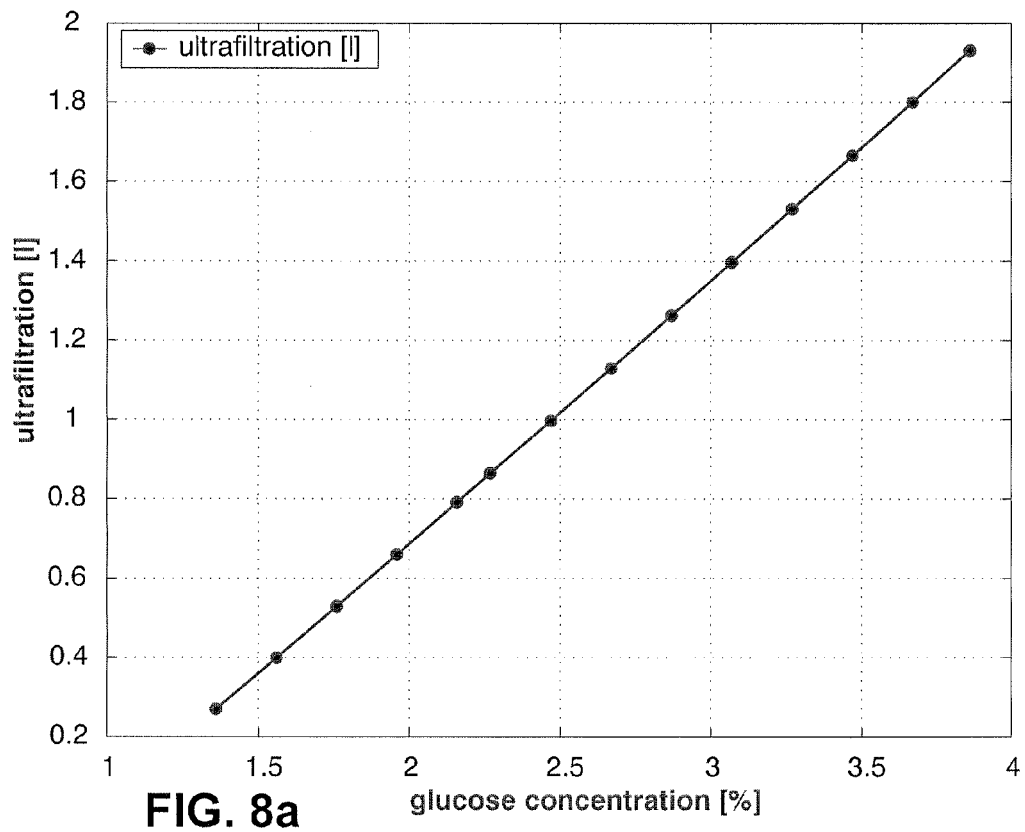
FIGS. 8a and 8b shows ultrafiltration (a) and glucose absorption (b) during the APD as function of the dialysate glucose concentration.
Figure 8B:
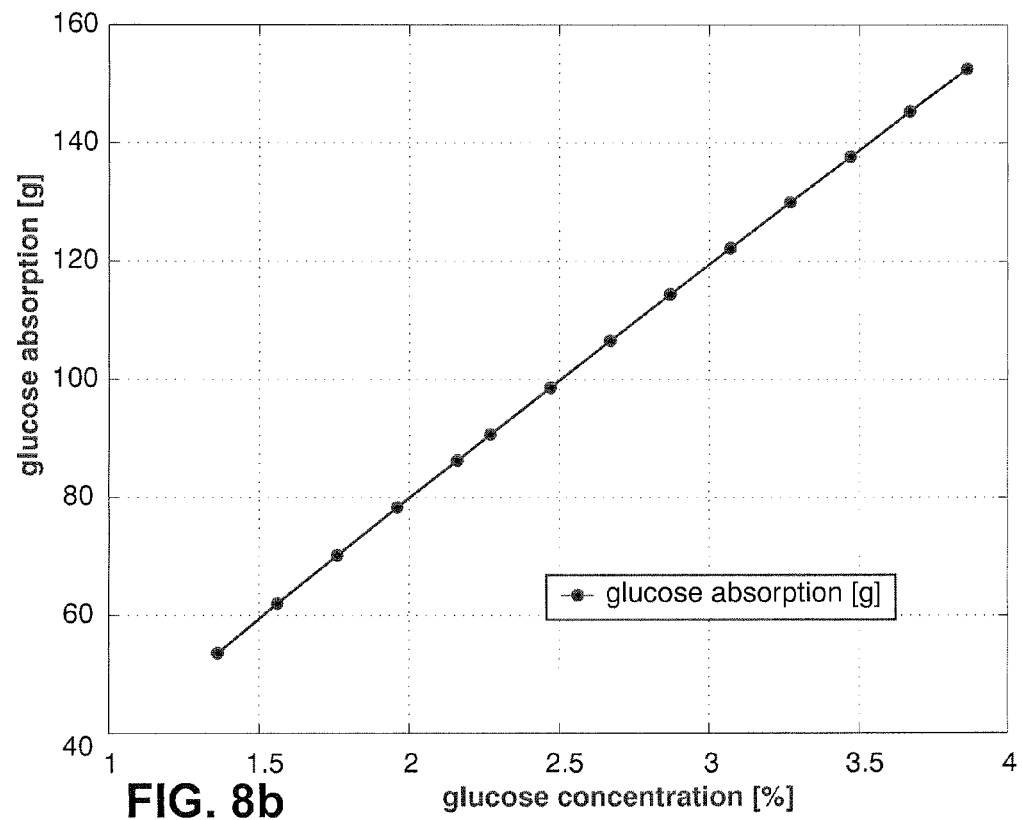

On one hand FIGS. 5a and 5b show that the extraction of urea and creatinine grows linearly according to the glucose input and FIGS. 6a and 6b show that the ultrafiltration is linearly dependent on glucose concentration. On the other hand, all the trends showed have a drawback. In fact, the therapy performance is better but the glucose absorbed from the patient is growing as well, thus compromising the PD biocompatibility.

Now we turn to the second patient b, classified as LA type, making the same tests. The numerical results are reported in table 2 as follows and FIGS. 7a-7b, 8a-8b:

TABLE 2

Numerical results related to patient B.
patient b, type LA

| glucose [%] | urea [g] | creatinine [g] | UF [l] | glucose absorption [g] |
|---|---|---|---|---|
| 1.36 | 9.037 | 0.234 | 0.270 | 53.624 |
| 1.56 | 9.168 | 0.239 | 0.399 | 61.985 |
| 1.76 | 9.301 | 0.245 | 0.529 | 70.174 |
| 1.96 | 9.435 | 0.251 | 0.660 | 78.299 |
| 2.16 | 9.571 | 0.256 | 0.791 | 86.255 |
| 2.27 | 9.647 | 0.260 | 0.865 | 90.670 |
| 2.47 | 9.784 | 0.266 | 0.997 | 98.642 |
| 2.67 | 9.921 | 0.272 | 1.130 | 106.559 |
| 2.87 | 10.060 | 0.278 | 1.263 | 114.413 |
| 3.07 | 10.199 | 0.284 | 1.397 | 122.223 |
| 3.27 | 10.340 | 0.291 | 1.531 | 129.983 |
| 3.47 | 10.482 | 0.297 | 1.666 | 137.695 |
| 3.67 | 10.624 | 0.304 | 1.801 | 145.362 |
| 3.86 | 10.761 | 0.310 | 1.931 | 152.543 |

The conclusion are quite similar to those drawn for patient a, regardless of patient classification.

Then we will set up a method to find the treatment representing the best compromise between a given level of efficiency and glucose absorption.

PD Simulations

Figure 9A:
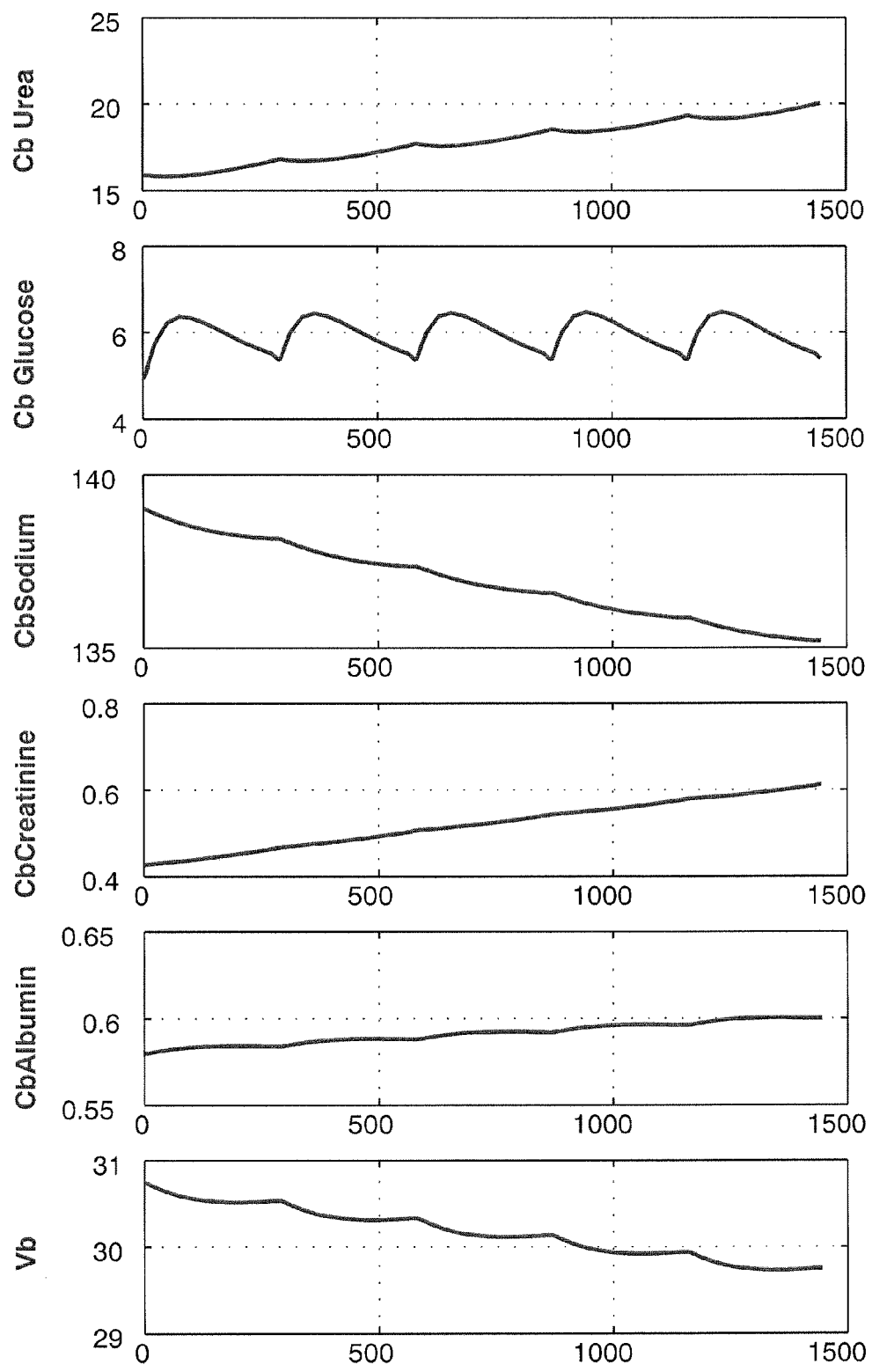
FIGS. 9a and 9b shows solutes dynamics in the body (b) compartment (a) and in the dialysate (d) compartment (b) during the CAPD process.
Figure 9B:
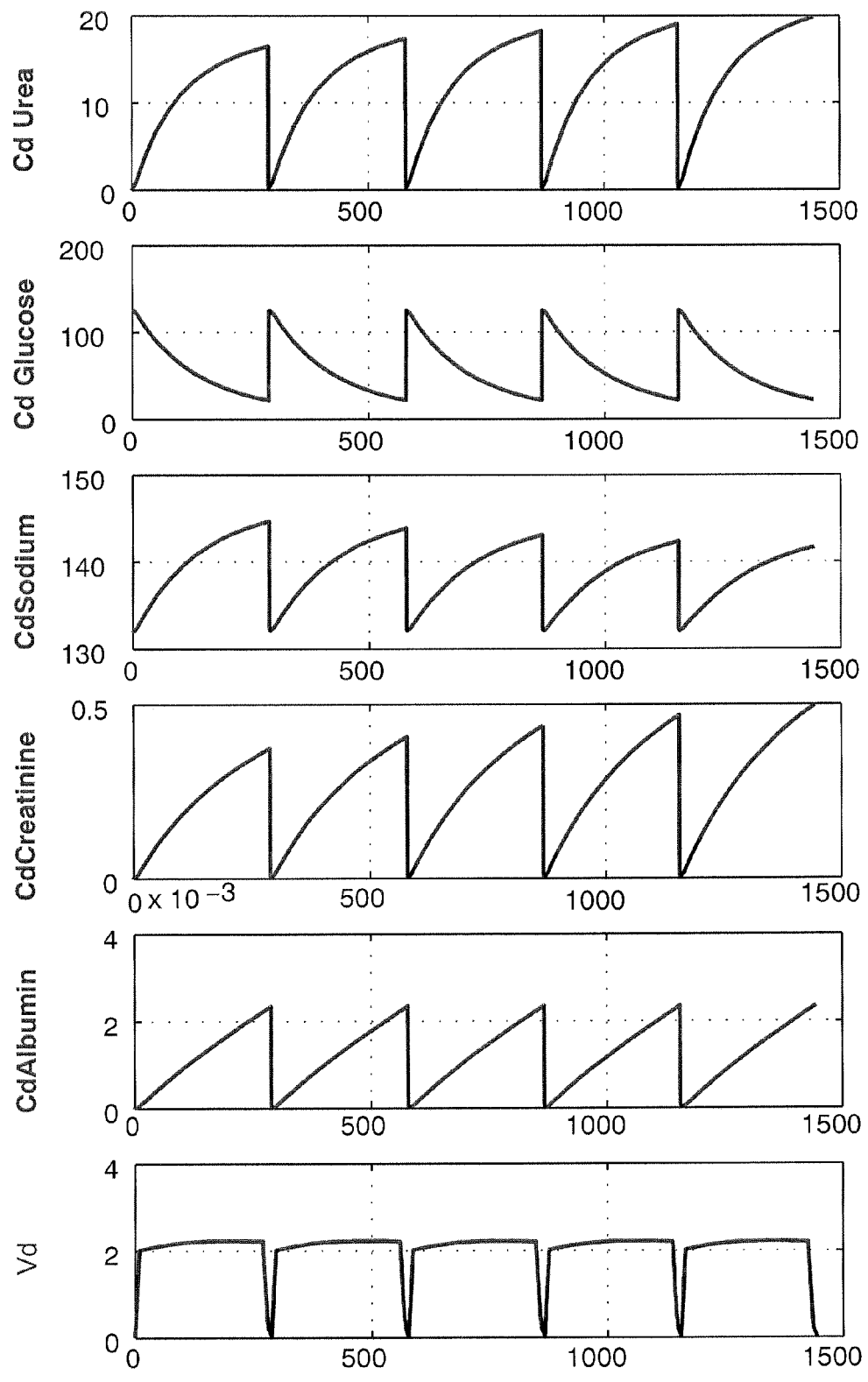

The three pore model is used now to investigate the PD process for a given patient. The model allows the recovery of many information about the patient and his behavior when submitted to a given treatment. We report the numerical results when a given patient is submitted to CAPD, CCPD and DPD. In order to compare the efficiency of the three PD therapies considered here, we fix the total therapy time to 1440 [min] and the total amount of dialysate to 10 liters. In the first test we consider a CAPD. The simulation provides the solute dynamics of urea, glucose, creatinine, sodium and albumin within the two compartment body (b) and dialysate (d) as shown in FIGS. 9a-9b. The solute concentration is given in [mmol=l].

The graphics given in the last line of FIGS. 9a-9b provide the dynamics of the fluid $V_b(t)$ and $V_d(t)$, respectively in the body and in the dialysate measured in [l]. Observe that the graph related to $V_b$ indicates that there is an amount of fluid drained from the patient, say ultrafiltration. The figure related to $V_d$ represents the PD profile corresponding to CAPD. The glucose concentration in the dialysate is 2:27%. The volume contained in the peritoneal cavity could violate the constraint related to the nominal capacity due to the ultrafiltration process. This explains why during the drain phase the pump drains completely the peritoneal cavity up to $V_{min}$ in order to avoid possible accumulation of fluid that could compromise the comfort of the patient in the following cycles.

Figure 10:
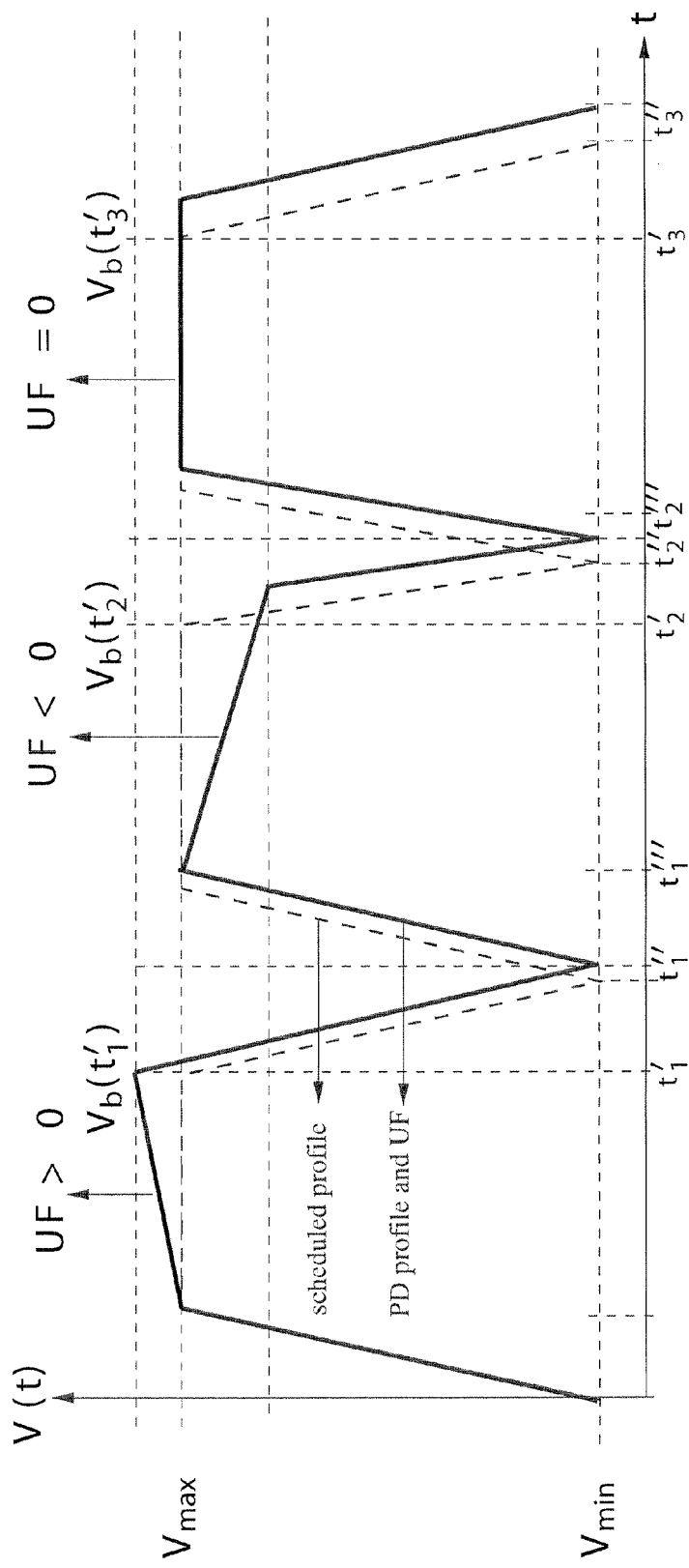
FIG. 10 shows management of the ultrafiltration.

FIG. 10 shows two different situations where we need to apply out the algorithm.

For instance, we observe that in the first cycle k=1 in equation (2) the ultrafiltration is positive UF>0 because $(V_b(t'_1)-V_{max})>0$. Thus the switching sequence is modified in order to drain the quantity $(V_b(t'_1)-V_{min})$ and all the components after the dwell time of the current cycle up to $t''_N$ are translated according to the following formula (2):

$$\begin{cases} t''_i = t'_i + \delta_i, i = k, \ldots, N, k = 1, \ldots, N, \\ t'''_i = t''_i + \delta_i, k \neq N, \\ t'_{i+1} = t'_{i+1} + \delta_i, k \neq N, \end{cases} \quad (2)$$

Where N is the number of cycles included in the therapy and the quantity $\delta_i=(V_b(t'_i)-V_{max})/|U|$ measures the time interval needed to drain the exceeding dialysate $(V_b(t'_i)-V_{max}>0)$ contained in the peritoneal cavity. |U| is the nominal flow rate of the pump. The same procedure is applied to each cycle. If the ultrafiltration is positive the therapy duration $(T_{tot})$ including the extra time needed to drain the ultrafiltration. The translation (2) is used also when the ultrafiltration is negative but in this case the direction is backward. The numerical solution provides also a quantitative evaluation of the treatment. The most important quantities computed are showed in tables 3 and 4:

TABLE 3 start and final concentration of the chemical in the body.
Numerical results body concentrations

| $c_b$ | start | end | unit |
|---|---|---|---|
| urea | 0.960 | 1.214 | [g/l] |
| creatinine | 4.810 | 6.916 | [mg/dl] |
| glucose | 0.890 | 0.969 | [g/l] |
| sodium | 139.00 | 135.19 | [mmol/l] |
| albumin | 4.00 | 4.14 | [g/dl] |

Table 3 contains the blood chemical concentration at the beginning and the end of the therapy.

Table 4 contains the main results related to the CAPD efficiency for the specific patient. The level of blood purification can be judged according to the extraction of urea, creatinine and the ultrafiltration.

TABLE 4

Numerical results related to a CAPD simulations.
Numerical results

| | | |
|---|---|---|
| body surface area | 1.657 | [m²] |
| $T_{tot}$ | 1445 | [min] |
| urea extracted | 11.985 | [g] |
| glucose extracted | 45.588 | [g] |
| sodium extracted | 86.409 | [g] |
| creatinine extracted | 0.529 | [g] |
| albumin extracted | 1.715 | [g] |
| $V_{tot}$ | 10.000 | [l] |
| dialysate extracted | 10.991 | [l] |
| ultrafiltration | 0.991 | [l] |
| $V_{min}$ | 0.001 | [l] |
| KT/V urea (weekly) | 2.843 | [l] |
| KT/V creatinine (weekly) | 2.506 | [l] |
| clearance urea | 9.050 | [ml/min/1.73 m²] |
| clearance creatinine | 7.979 | [ml/min/1.73 m²] |
| body surface | 2.722 | [m²] |
| body mass index | 21.671 | [kg/m²] |

Figure 11A:
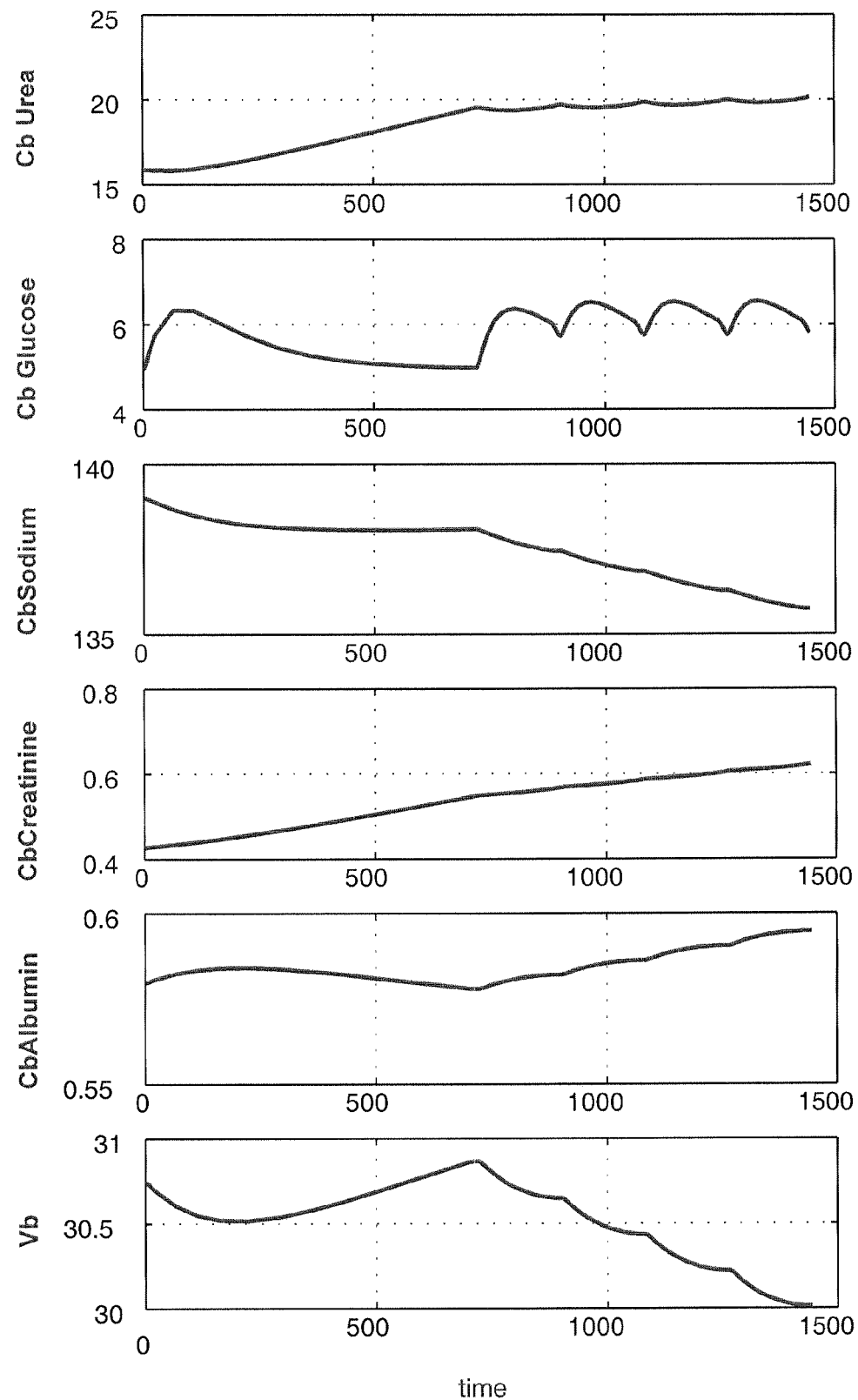
FIGS. 11a and 11b shows solute dynamic in the body (b) compartment (a) and in the dialysate (d) compartment (b) during the CCPD process.
Figure 11B:
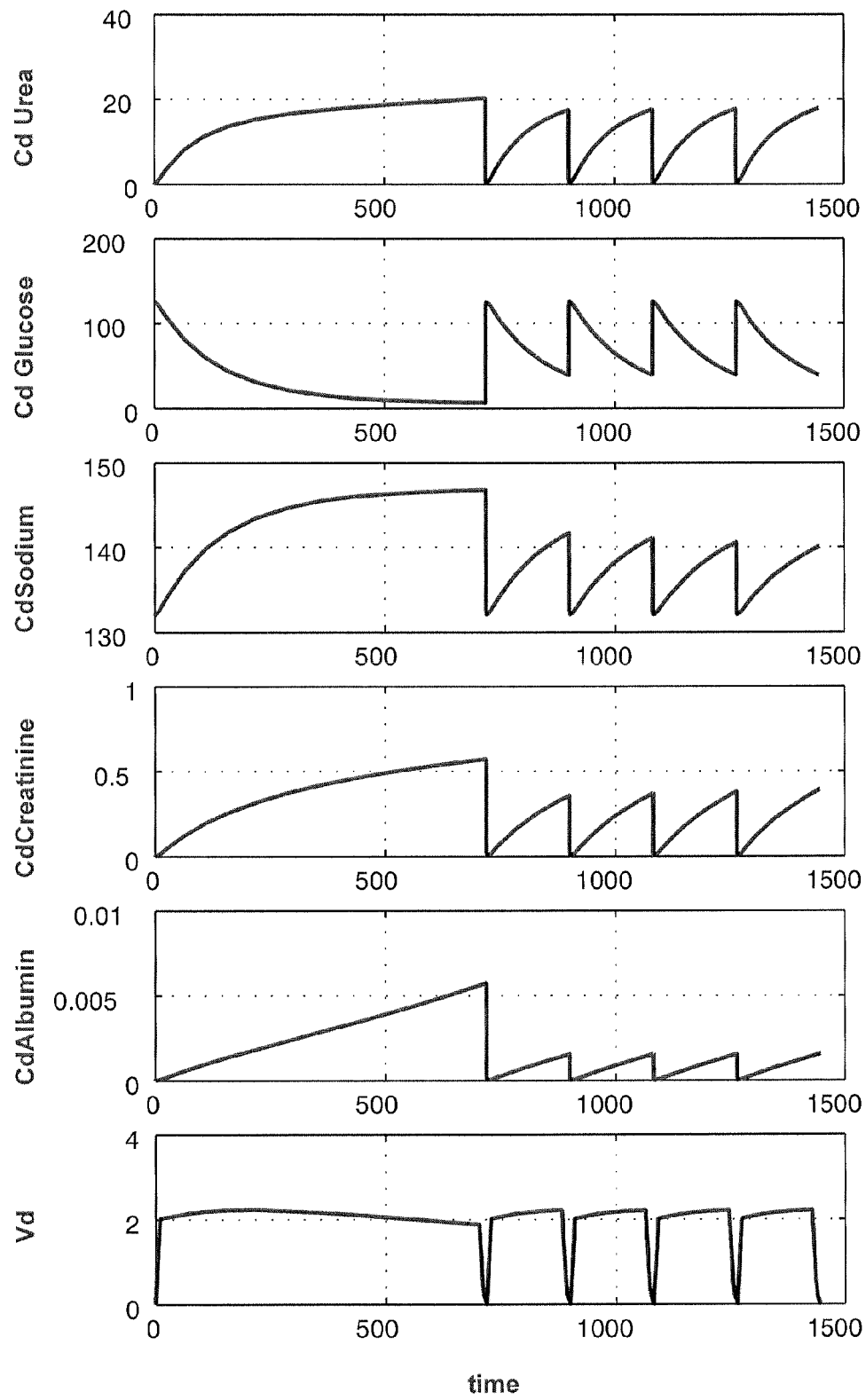

In the second example the patient is submitted to a CCPD therapy. The numerical results allow to describe the evolution of the system as showed in FIGS. 11a-11b.

The quantitative information related to the CCPD process and produced by the numerical simulation are showed in tables 5 and 6. Table 5 contains the blood chemical concentration at the beginning and the end of the therapy.

TABLE 5

The start and final concentration
of the chemical in the body.
Numerical results body concentrations

| $c_b$ | start | end | unit |
|---|---|---|---|
| urea | 0.960 | 1.219 | [g/l] |
| creatinine | 4.810 | 7.026 | [mg/dl] |
| glucose | 0.890 | 1.043 | [g/l] |
| sodium | 139.00 | 135.73 | [mmol/l] |
| albumin | 4.00 | 4.10 | [g/dl] |

Table 6 contains the results related to the CCPD efficiency for the specific patient. The level of blood purification can be judged according to the extraction of urea, creatinine and the ultrafiltration.

TABLE 6

Numerical results related to a CCPD simulations.
Numerical results

| | | |
|---|---|---|
| body surface area | 1.657 | [m²] |
| $T_{tot}$ | 1444 | [min] |
| urea extracted | 11.501 | [g] |
| glucose extracted | 69.035 | [g] |
| sodium extracted | 83.548 | [g] |
| creatinine extracted | 0.477 | [g] |
| albumin extracted | 1.615 | [g] |
| $V_{tot}$ | 10.000 | [l] |
| dialysate extracted | 10.727 | [l] |
| ultrafiltration | 0.727 | [l] |

TABLE 6-continued

Numerical results related to a CCPD simulations.
Numerical results

| | | |
|---|---|---|
| $V_{min}$ | 0.001 | [l] |
| KT/V urea (weekly) | 2.728 | [l] |
| KT/V creatinine (weekly) | 2.259 | [l] |
| clearance urea | 8.685 | [ml/min/1.73 m²] |
| clearance creatinine | 7.192 | [ml/min/1.73 m²] |
| body surface | 2.722 | [m²] |
| body mass index | 21.671 | [kg/m²] |

Figure 12A:
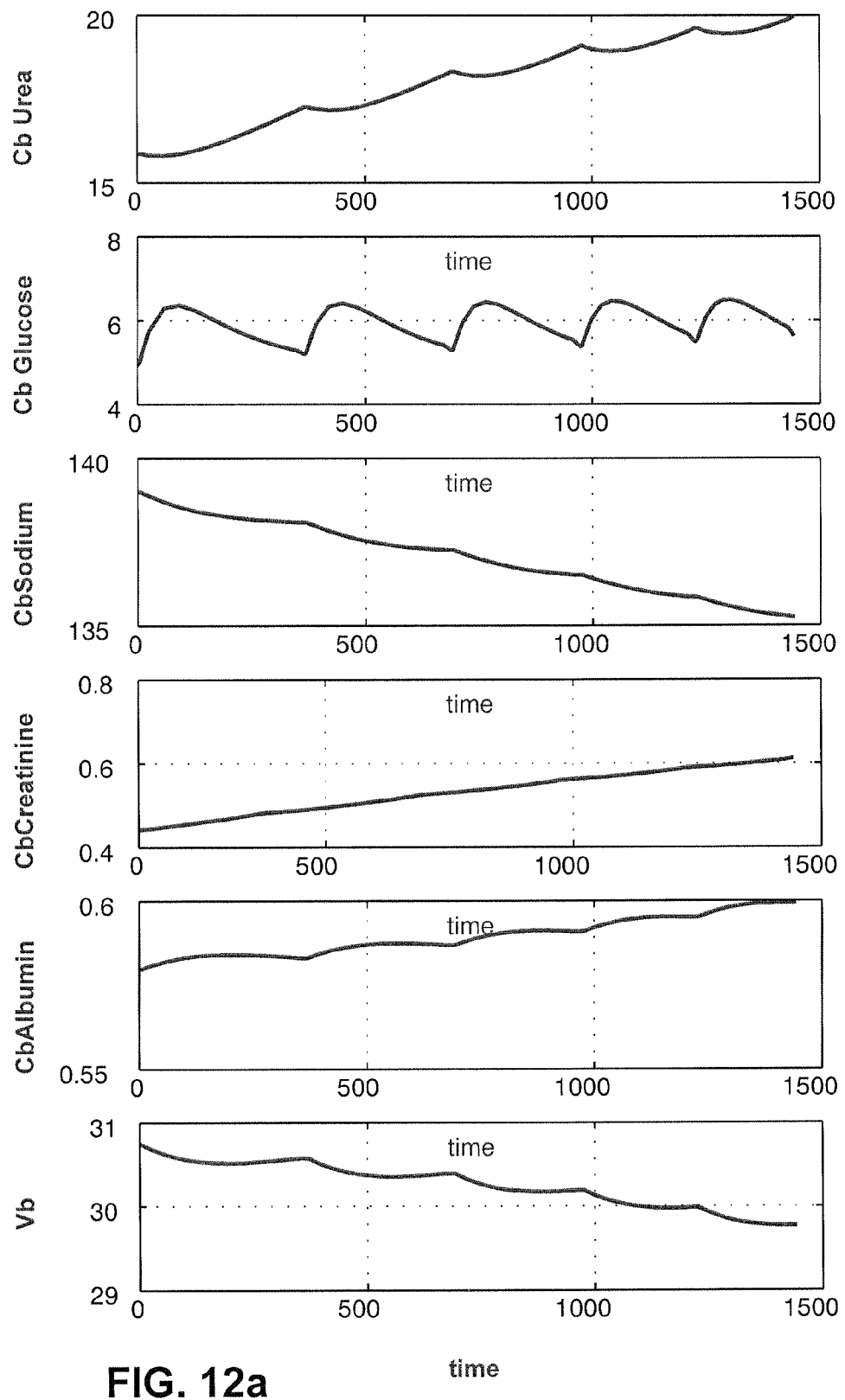
FIGS. 12a and 12b shows solute dynamic in the body (b) compartment (a) and in the dialysate (d) compartment (b) during the DPD process.
Figure 12B:
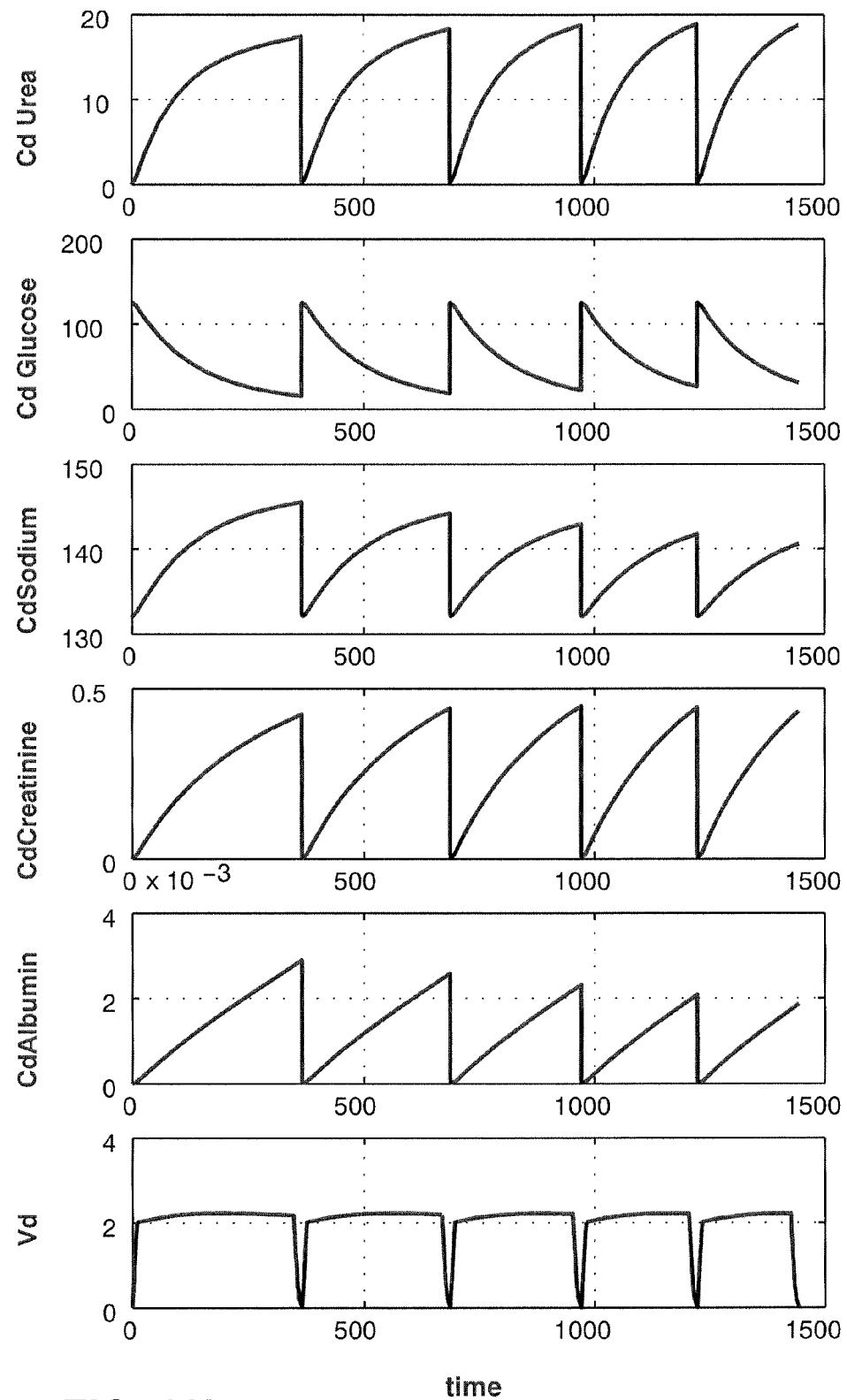

We consider a third example where the patient is submitted to a DPD profile characterized by a decreasing dwell time switching form one cycle to the another. FIGS. 12a-12b represent the numerical results.

The numerical simulation of this profile is obtained by the parametrization of the control function corresponding to a=[5, 0.87, 1.01, 0, 0]. The quantitative information related to the DPD process and produced by the numerical simulation are showed in tables 7 and 8.

TABLE 7

The start and final concentration of the chemical in the body.
Numerical results body concentrations

| $c_b$ | start | end | unit |
|---|---|---|---|
| urea | 0.960 | 1.210 | [g/l] |
| creatinine | 4.810 | 6.908 | [mg/dl] |
| glucose | 0.890 | 1.011 | [g/l] |
| sodium | 139.00 | 135.25 | [mmol/l] |
| albumin | 4.00 | 4.14 | [g/dl] |

Table 8 contains the main results related to the DPD efficiency for the specific patient. The level of blood purification can be judged according to the extraction of urea, creatinine and the ultrafiltration.

TABLE 8

Numerical results related to a DPD simulations.
Numerical results

| | | |
|---|---|---|
| body surface area | 1.657 | [m²] |
| $T_{tot}$ | 1445 | [min] |
| urea extracted | 12.101 | [g] |
| glucose extracted | 47.634 | [g] |
| sodium extracted | 86.147 | [g] |
| creatinine extracted | 0.530 | [g] |
| albumin extracted | 1.707 | [g] |
| $V_{tot}$ | 10.000 | [l] |
| dialysate extracted | 10.969 | [l] |
| ultrafiltration | 0.969 | [l] |
| $V_{min}$ | 0.001 | [l] |
| KT/V urea (weekly) | 2.870 | [l] |
| KT/V creatinine (weekly) | 2.510 | [l] |
| clearance urea | 0.138 | [ml/min/1.73 m²] |
| clearance creatinine | 7.990 | [ml/min/1.73 m²] |
| body surface | 2.722 | [m²] |
| body mass index | 21.671 | [kg/m²] |

A comparison between the three therapies is made in table 9:

TABLE 9

A comparison of CAPD, CCPD and DPD.

| quantity | CAPD | CCPD | DPD | unit | comparison |
|---|---|---|---|---|---|
| urea extracted | 11.985 | 11.501 | 12.101 | [g] | DPD > CAPD > CCPD |
| creatinine extracted | 0.529 | 0.477 | 0.530 | [g] | DPD > CAPD > CCPD |
| ultrafiltration | 0.991 | 0.727 | 0.969 | [l] | CAPD > DPD > CCPD |
| glucose extracted | 45.588 | 69.035 | 47.634 | [g] | CCPD > DPD > CAPD |
| glucose absorbed | 181.412 | 157.965 | 179.366 | [g] | CCPD > DPD > CAPD |

It is shown that it is possible to reach a better level of blood purification using a non standard PD profile. For instance, the given DPD profile provides the best extraction in terms of urea and creatinine. CAPD provides the best ultrafiltration level even if the difference with respect to DPD is small. CCPD is characterized as the worst case. Nevertheless, it should be taken into account that the CCPD profile allows to get the minimum level of glucose absorption because the extraction is the highest. It would be too heavy to test at hand a large set of PD profile to establish what would be the best. An optimization procedure allows to approximate the best PD profile automatically. In next section we discuss the numerical results obtained by the application of these techniques.

Analysis of Peritoneal Dialysis Performance

This section deals with the extensive analysis of changes on peritoneal dialysis performance with respect to changes on input parameters. More precisely, by means of the three pore model, we analyze the performance of several therapy options, differing on the total dialysate volume, the total therapy time and the peritoneal filling volume. In particular, our tests were designed to investigate in what conditions dynamic peritoneal dialysis (DPD) is a favorable choice with respect to more standard therapies, as for example (APD). Our numerical tests are subdivided in two parts:

1. we investigate the influence of the total dialysate volume ($V_{tot}$) and the total therapy time ($T_{tot}$) on the optimal therapy prescription, 2. we consider the influence of the peritoneal filling volume.

Influence of $V_{tot}$ and $T_{tot}$ on optimal therapy prescription:

The total dialysate volume and the total therapy time have a sensible influence on the optimal dialysis therapy for a specific patient. The effect of total dialysate volume is reported in table 10 and summarized in FIG. 13. The results in this section are obtained applying a realistic pump profile.

This test shows the increase of performance ($KT/V_{urea}$) of the optimal DPD therapy with respect to the standard APD at different values of the total volume. All the other parameters are constant.

Three patients have been considered, with different peritoneal characteristics, precisely a high transporter (H), an average transporter (LA) and a low transporter (L). This test puts into evidence that for all type of patient:

at low total dialysate volumes (less than 8 liters) the optimal therapy is the APD because no changes in the standard profile are detected, the changes in the standard profile are emphasized with the increase of the total volume. With a total dialysate volume of 16 liters the optimal therapy features one cycles more than the standard APD and its $KT/V_{urea}$ is increased by 12% with respect to the latter, in all the examined cases, where DPD appears to be the optimal therapy, variations in the shape of the cycles can be put into evidence according to the values of α and β.

The influence of the total time $T_{tot}$ is investigated in the second test. In this case we report the increase of $KT/V_{urea}$ corresponding to the optimal DPD with respect to the standard APD at several values of the duration of the therapy. All the remaining parameters are constant. The effect of total time is reported in table 11 and summarized in FIG. 14.

TABLE 10

Numerical results related to a patient of type H.
patient, type H

| | APD | | | DPD | | | | |
|---|---|---|---|---|---|---|---|---|---|
| $V_{tot}$ [l] | cycle | $KT/V_{urea}$ | UF [l] | cycle | α | β | $KT/V_{urea}$ | UF [l] | improv. [%] |
| 4 | 2 | 0.944 | 0.192 | 2 | 1.000 | 1.000 | 0.944 | 0.1925 | 0.000 |
| 6 | 3 | 1.280 | 0.274 | 3 | 1.000 | 1.000 | 1.280 | 0.273 | 0.000 |
| 8 | 4 | 1.443 | 0.316 | 4 | 1.000 | 1.000 | 1.442 | 0.315 | 0.000 |
| 10 | 5 | 1.527 | 0.336 | 6 | 0.995 | 1.001 | 1.566 | 0.343 | 2.578 |
| 12 | 6 | 1.561 | 0.343 | 7 | 0.981 | 0.993 | 1.647 | 0.364 | 5.518 |
| 14 | 7 | 1.562 | 0.342 | 8 | 1.003 | 0.972 | 1.675 | 0.373 | 7.297 |
| 16 | 8 | 1.538 | 0.335 | 9 | 0.966 | 0.985 | 1.730 | 0.384 | 12.538 |

TABLE 11

Numerical results related to patient of type H.

patient, type H

| $T_{tot}$ [min] | APD | | | DPD | | | | | |
|---|---|---|---|---|---|---|---|---|---|
| | cycle | $KT/V_{urea}$ | UF [l] | cycle | α | β | $KT/V_{urea}$ | UF [l] | improv. [%] |
| 200 | 5 | 0.705 | 0.140 | 6 | 0.951 | 0.999 | 0.887 | 0.179 | 25.832 |
| 300 | 5 | 1.132 | 0.236 | 6 | 0.995 | 1.001 | 1.239 | 0.261 | 9.432 |
| 360 | 5 | 1.331 | 0.286 | 6 | 0.983 | 0.999 | 1.404 | 0.302 | 5.429 |
| 420 | 5 | 1.497 | 0.328 | 6 | 1.013 | 1.002 | 1.541 | 0.334 | 2.930 |
| 480 | 5 | 1.636 | 0.365 | 6 | 1.001 | 0.999 | 1.658 | 0.367 | 1.328 |
| 540 | 5 | 1.752 | 0.397 | 6 | 1.000 | 0.998 | 1.756 | 0.392 | 0.220 |
| 600 | 5 | 1.849 | 0.423 | 5 | 1.000 | 1.000 | 1.849 | 0.423 | 0.000 |
| 660 | 5 | 1.931 | 0.445 | 5 | 1.000 | 1.000 | 1.931 | 0.445 | 0.000 |

The test on $T_{tot}$ shows that for all type of patient:
- at high therapy times (more than 9 hours) the APD is the optimal therapy,
- at low therapy times (less than 6 hours) the optimal therapy differs from the APD,
- all the optimal therapies obtained feature small variations in cycle shape.

To sum up, we observe that the phenomena described above have a common explanation. The increase of dialysate volumes and the decrease of the duration of the therapy have the effect of shortening the dwell time of each cycle. Furthermore, the performance of the cycles with short dwell times is highly penalized by the slow drain rates at the end of the extraction process. Consequently, in these specific conditions, the optimal therapy is the one that exchanges at each cycle the amount of dialysate available above the slow drain rate threshold.

PD Optimal Control by the Control Function Parametrization

We would like to investigate the PD optimization taking into account different therapy constraints $V_{max}$, $V_{min}$ and $T_{tot}$ and the patient characteristics. The peritoneal membrane characteristics p and h are chosen in the range of admissible physiological values. The results are meaningful even if using fictitious patients their characteristics are not obtained through a parameter identification procedure. This investigation allows to provide answers with respect to the behavior of a patient depending on the input therapy. As starting point of optimization procedure we consider a standard APD therapy as follows:

$T_{tot}$=520[min], $V_{tot}$=12[l], $V_{max}$=2001[l], $V_{min}$=1[ml],

N=6, glucose=2.27%  (3)

where N denotes the number of cycles included in the PD therapy. The parameters corresponding to the standard APD are a=[1, 1, 0, 0, 6]. We submit to the optimization procedure a set of 15 virtual patients separated in the class LA, HA, H. The efficiency parameter $E_{ff}(a)$ used in this investigation is as follows:

$$E_{ff}(a) = \frac{1}{3}KT/V_{urea} + \frac{1}{3}Cl_{creat.} + \frac{1}{3}UF \quad (4)$$

wherein the following indicators are used:
weekly normalized extracted urea, called KT=Vurea, $$KT/V_{urea} = \frac{7}{V_b(t=0)c_{b_{urea}}(t=0)} \int_0^{T_{tot}} c_{d_{urea}} |\min[u(t), 0]| dt$$

clearance creatinine called Clcreat, $$Cl_{creat} = \frac{1.73 \cdot V_{tot}}{60 \cdot T_{tot} \cdot BSA \cdot -c_{b_{creat}}(t=0)} \int_0^{T_{tot}} c_{d_{creat}} |\min[u(t), 0]| dt$$

ultrafiltration, $UF = Vd(t=Ttot) - Vd(t=0)$ the set W $$W = \left\{(w_1, w_2, w_3) \mid \forall w \in \mathbb{R}_+ \cup \{0\}, \text{ and } \sum_{i=1}^{3} w_i = 1\right\}.$$

The numerical results obtained are showed in the next tables. Precisely, for each patient class we consider a group of females (F) and males (M). The results provide all the components of the index of performance (4). The improvements columns allow to compare componentwise the efficiency of a standard APD and the optimized DPD. We point out that our index of performance is a weighted combination of different objectives. Thus the algorithm seeks to optimize this quantity instead of each single objective. First of all let us show the comparison between APD and DPD with respect to the index of performance (4). Next table provides the numerical results related to a group of 18 female patients.

| $A_0/\Delta x$ [cm/1.73 m$^2$] | gender | $E_{ff}$(APD) | $E_{ff}$(DPD) | improv. [%] |
|---|---|---|---|---|
| 17902 | F | 1.224 | 1.284 | 4.844 |
| 18937 | F | 1.315 | 1.375 | 4.588 |
| 19972 | F | 1.403 | 1.464 | 4.347 |
| 21007 | F | 1.488 | 1.549 | 4.097 |
| 22041 | F | 1.572 | 1.633 | 3.858 |

-continued

| $A_0/\Delta x$ [cm/1.73 m$^2$] | gender | $E_{ff}$(APD) | $E_{ff}$(DPD) | improv. [%] |
|---|---|---|---|---|
| 23076 | F | 1.654 | 1.714 | 3.647 |
| 24111 | F | 1.733 | 1.793 | 3.461 |
| 25146 | F | 1.811 | 1.869 | 3.239 |
| 26181 | F | 1.886 | 1.944 | 3.056 |
| 27216 | F | 1.960 | 2.016 | 2.856 |
| 28251 | F | 2.032 | 2.086 | 2.657 |
| 29286 | F | 2.102 | 2.154 | 2.489 |
| 30321 | F | 2.170 | 2.221 | 2.349 |
| 31355 | F | 2.237 | 2.286 | 2.205 |
| 32390 | F | 2.301 | 2.348 | 2.042 |
| 33425 | F | 2.365 | 2.408 | 1.832 |
| 34460 | F | 2.427 | 2.469 | 1.730 |
| 35495 | F | 2.486 | 2.526 | 1.595 |

Next table provides the numerical results related a group of 18 male patients.

| $A_0/\Delta x$ [cm/1.73 m$^2$] | gender | $E_{ff}$(APD) | $E_{ff}$(DPD) | improv. [%] |
|---|---|---|---|---|
| 17902 | M | 1.129 | 1.177 | 4.279 |
| 18937 | M | 1.214 | 1.262 | 3.980 |
| 19972 | M | 1.296 | 1.344 | 3.728 |
| 21007 | M | 1.376 | 1.423 | 3.414 |
| 22041 | M | 1.454 | 1.500 | 3.185 |
| 23076 | M | 1.529 | 1.575 | 2.963 |
| 24111 | M | 1.603 | 1.647 | 2.723 |
| 25146 | M | 1.674 | 1.716 | 2.508 |
| 26181 | M | 1.744 | 1.784 | 2.312 |
| 27216 | M | 1.811 | 1.849 | 2.097 |
| 28251 | M | 1.876 | 1.912 | 1.900 |
| 29286 | M | 1.940 | 1.974 | 1.752 |
| 30321 | M | 2.001 | 2.033 | 1.598 |
| 31355 | M | 2.061 | 2.090 | 1.423 |
| 32390 | M | 2.119 | 2.146 | 1.258 |
| 33425 | M | 2.175 | 2.200 | 1.133 |
| 34460 | M | 2.231 | 2.252 | 0.956 |
| 35495 | M | 2.284 | 2.303 | 0.831 |

The third column (improv.) shows that the optimized DPD therapy allows to obtain a better performance with respect to the APD. The improvement ranges approximately from 1 to 5 percent.

The improvement seems to depended linearly on the area parameter $A_0/\Delta x$ and independent of the gender. The decreasing trend of the improvement with respect to $A_0/\Delta x$ could be explained by the fact that patients characterized by high values $A_0/\Delta x$ dissipate the gradient of chemical concentration between the body (b) and the dialysate (d) rapidly. Moreover both for male and female the PD performance behaves linearly and reaches the highest values for HA patients. FIG. 15 shows a graphic comparison between APD and DPD.

Let us show the results of the optimization process in a more extended form in order to recognize the behavior of the PD system related to the component of index of performance (4). Next table provides the uncombined results for KT/V$_{urea}$, Cl$_{creat}$, and ultrafiltration (UP). The table below provides the numerical results related to a group of female patients.

| $A_0/\Delta x$ | gender | APD KT/V$_{urea}$ | DPD KT/V$_{urea}$ | % improv. | APD Cl$_{creat.}$ | DPD Cl$_{creat.}$ | % improv. | APD UF | DPD UF | % improv. |
|---|---|---|---|---|---|---|---|---|---|---|
| 17902 | F | 1.144 | 1.187 | 3.758 | 2.138 | 2.265 | 5.940 | 0.392 | 0.400 | 2.040 |
| 18937 | F | 1.212 | 1.254 | 3.465 | 2.279 | 2.409 | 5.704 | 0.454 | 0.463 | 1.982 |
| 19972 | F | 1.278 | 1.319 | 3.208 | 2.417 | 2.549 | 5.461 | 0.514 | 0.524 | 1.945 |
| 21007 | F | 1.341 | 1.380 | 2.908 | 2.553 | 2.687 | 5.248 | 0.572 | 0.582 | 1.748 |
| 22041 | F | 1.402 | 1.439 | 2.639 | 2.687 | 2.822 | 5.024 | 0.628 | 0.638 | 1.592 |
| 23076 | F | 1.460 | 1.496 | 2.465 | 2.818 | 2.954 | 4.826 | 0.684 | 0.693 | 1.315 |
| 24111 | F | 1.516 | 1.550 | 2.242 | 2.947 | 3.084 | 4.648 | 0.737 | 0.746 | 1.221 |
| 25146 | F | 1.570 | 1.602 | 2.038 | 3.074 | 3.210 | 4.424 | 0.789 | 0.797 | 1.013 |
| 26181 | F | 1.622 | 1.652 | 1.849 | 3.198 | 3.334 | 4.452 | 0.840 | 0.847 | 0.833 |
| 27216 | F | 1.672 | 1.699 | 1.614 | 3.320 | 3.455 | 4.066 | 0.889 | 0.895 | 0.674 |
| 28251 | F | 1.720 | 1.745 | 1.453 | 3.440 | 3.573 | 3.866 | 0.937 | 0.941 | 0.426 |
| 29286 | F | 1.766 | 1.789 | 1.302 | 3.557 | 3.689 | 3.711 | 0.984 | 0.986 | 0.203 |
| 30321 | F | 1.811 | 1.831 | 1.104 | 3.672 | 3.803 | 3.567 | 1.029 | 1.031 | 0.194 |
| 31355 | F | 1.854 | 1.872 | 0.970 | 3.785 | 3.914 | 3.408 | 1.072 | 1.073 | 0.093 |
| 32390 | F | 1.894 | 1.911 | 0.897 | 3.896 | 4.022 | 3.234 | 1.115 | 1.113 | -0.179 |
| 33425 | F | 1.934 | 1.947 | 0.672 | 4.005 | 4.126 | 3.021 | 1.156 | 1.152 | -0.346 |
| 34460 | F | 1.972 | 1.984 | 0.608 | 4.112 | 4.232 | 2.918 | 1.197 | 1.191 | -0.501 |
| 35495 | F | 2.008 | 2.018 | 0.498 | 4.216 | 4.334 | 2.798 | 1.236 | 1.227 | -0.728 |

Next table provides the numerical results related to a group of male patients.

| $A_0/\Delta x$ | gender | APD KT/V$_{urea}$ | DPD KT/V$_{urea}$ | % improv. | APD Cl$_{creat.}$ | DPD Cl$_{creat.}$ | % improv. | APD UF | DPD UF | % improv. |
|---|---|---|---|---|---|---|---|---|---|---|
| 17902 | M | 0.898 | 0.926 | 3.118 | 2.036 | 2.148 | 5.501 | 0.454 | 0.459 | 1.101 |
| 18937 | M | 0.950 | 0.977 | 2.842 | 2.168 | 2.281 | 5.212 | 0.525 | 0.530 | 0.952 |
| 19972 | M | 0.999 | 1.025 | 2.602 | 2.297 | 2.411 | 4.963 | 0.593 | 0.598 | 0.843 |
| 21007 | M | 1.047 | 1.070 | 2.196 | 2.424 | 2.538 | 4.703 | 0.659 | 0.663 | 0.607 |
| 22041 | M | 1.092 | 1.114 | 2.014 | 2.548 | 2.662 | 4.474 | 0.723 | 0.726 | 0.414 |
| 23076 | M | 1.135 | 1.155 | 1.762 | 2.669 | 2.783 | 4.271 | 0.785 | 0.787 | 0.254 |
| 24111 | M | 1.177 | 1.195 | 1.529 | 2.788 | 2.901 | 4.053 | 0.845 | 0.845 | 0.000 |
| 25146 | M | 1.216 | 1.233 | 1.398 | 2.905 | 3.016 | 3.821 | 0.903 | 0.901 | -0.221 |
| 26181 | M | 1.254 | 1.269 | 1.196 | 3.019 | 3.129 | 3.643 | 0.959 | 0.955 | -0.417 |

-continued

| $A_0/\Delta x$ | gender | APD $KT/V_{urea}$ | DPD $KT/V_{urea}$ | % improv. | APD $Cl_{creat.}$ | DPD $Cl_{creat.}$ | % improv. | APD UF | DPD UF | % improv. |
|---|---|---|---|---|---|---|---|---|---|---|
| 27216 | M | 1.290 | 1.303 | 1.007 | 3.131 | 3.238 | 3.417 | 1.013 | 1.007 | −0.592 |
| 28251 | M | 1.325 | 1.335 | 0.754 | 3.240 | 3.345 | 3.240 | 1.065 | 1.057 | −0.751 |
| 29286 | M | 1.358 | 1.367 | 0.662 | 3.347 | 3.449 | 3.047 | 1.115 | 1.106 | −0.807 |
| 30321 | M | 1.389 | 1.397 | 0.576 | 3.451 | 3.551 | 2.897 | 1.164 | 1.152 | −1.030 |
| 31355 | M | 1.420 | 1.425 | 0.352 | 3.553 | 3.650 | 2.730 | 1.211 | 1.197 | −1.156 |
| 32390 | M | 1.449 | 1.452 | 0.207 | 3.653 | 3.747 | 2.573 | 1.257 | 1.240 | −1.352 |
| 33425 | M | 1.476 | 1.478 | 0.135 | 3.751 | 3.841 | 2.399 | 1.300 | 1.282 | −1.384 |
| 34460 | M | 1.503 | 1.504 | 0.065 | 3.847 | 3.932 | 2.209 | 1.343 | 1.321 | −1.638 |
| 35495 | M | 1.528 | 1.527 | −0.065 | 3.940 | 4.022 | 2.081 | 1.384 | 1.360 | −1.734 |

Note that because of the multiobjective approach expressed by (4) it is possible that the improvement would be obtained without an increase of all the components. The trends for the objectives for both female and male patients are showed in FIG. 16.

FIG. 16 shows also that the creatinine clearance is more sensible to the DPD profile with respect to $KT/V_{urea}$ and UF. In order to put into evidence the characteristics of DPD profile and to compare them with a standard APD profile let us summarize the optimal values provided by the optimization algorithm for both female and male groups.

| $A_0/\Delta x$ | gender | APD | | | | | DPD | | | | |
|---|---|---|---|---|---|---|---|---|---|---|---|
| | | α | β | γ | δ | N | α | β | γ | δ | N |
| 17902 | F | 1 | 1 | 0 | 0 | 6 | 0.957 | 0.969 | 2.9e−4 | −3.1e−4 | 7 |
| 18937 | F | " | " | " | " | " | 0.956 | 0.969 | 1.6e−4 | −2.2e−4 | 7 |
| 19972 | F | " | " | " | " | " | 0.957 | 0.968 | 2.0e−4 | 2.0e−6 | 7 |
| 21007 | F | " | " | " | " | " | 0.957 | 0.968 | 1.73−4 | −2.6e−4 | 7 |
| 22041 | F | " | " | " | " | " | 0.955 | 0.969 | 1.8e−4 | −1.6e−4 | 7 |
| 23076 | F | " | " | " | " | " | 0.956 | 0.969 | 1.8e−4 | −3.0e−4 | 7 |
| 24111 | F | " | " | " | " | " | 0.955 | 0.969 | 1.1e−4 | −3.8e−4 | 7 |
| 25146 | F | " | " | " | " | " | 0.954 | 0.970 | 1.9e−4 | −5.2e−4 | 7 |
| 26181 | F | " | " | " | " | " | 0.956 | 0.969 | −3.0e−4 | −2.0e−4 | 7 |
| 27216 | F | " | " | " | " | " | 0.956 | 0.968 | −5.0e−5 | 3.8e−5 | 7 |
| 28251 | F | " | " | " | " | " | 0.956 | 0.968 | −1.0e−4 | 7.8e−5 | 7 |
| 29286 | F | " | " | " | " | " | 0.957 | 0.969 | −3.7e−4 | −2.5e−4 | 7 |
| 30321 | F | " | " | " | " | " | 0.957 | 0.968 | −3.e−4 | 1.6e−4 | 7 |
| 31355 | F | " | " | " | " | " | 0.956 | 0.969 | −3.4e−4 | −2.6e−4 | 7 |
| 32390 | F | " | " | " | " | " | 0.957 | 0.968 | −2.9e−4 | 2.5e−4 | 7 |
| 33425 | F | " | " | " | " | " | 1.017 | 1.032 | −1.6e−4 | −1.6e−4 | 7 |
| 34460 | F | " | " | " | " | " | 0.957 | 0.968 | −2.9e−4 | 2.9e−4 | 7 |
| 35495 | F | " | " | " | " | " | 0.956 | 0.969 | −2.7e−4 | −2.3e−4 | 7 |

| $A_0/\Delta x$ | gender | APD | | | | | DPD | | | | |
|---|---|---|---|---|---|---|---|---|---|---|---|
| | | α | β | γ | δ | N | α | β | γ | δ | N |
| 17902 | M | 1 | 1 | 0 | 0 | 6 | 0.958 | 0.969 | 1.5e−4 | −1.7e−4 | 7 |
| 18937 | M | " | " | " | " | " | 0.957 | 0.969 | 4.6e−4 | −1.6e−4 | 7 |
| 19972 | M | " | " | " | " | " | 0.957 | 0.969 | 4.1e−4 | −1.1e−4 | 7 |
| 21007 | M | " | " | " | " | " | 0.958 | 0.969 | −3.4e−5 | −3.5e−4 | 7 |
| 22041 | M | " | " | " | " | " | 0.959 | 0.968 | 2.6e−5 | −8.1e−6 | 7 |
| 23076 | M | " | " | " | " | " | 0.964 | 0.969 | −4.2e−4 | −1.4e−4 | 7 |
| 24111 | M | " | " | " | " | " | 0.959 | 0.968 | −2.6e−4 | 9.8e−5 | 7 |
| 25146 | M | " | " | " | " | " | 0.960 | 0.969 | −3.0e−4 | −2.6e−4 | 7 |
| 26181 | M | " | " | " | " | " | 0.960 | 0.968 | −2.8e−4 | 2.4e−4 | 7 |
| 27216 | M | " | " | " | " | " | 0.960 | 0.968 | −2.8e−4 | 2.2e−4 | 7 |
| 28251 | M | " | " | " | " | " | 0.966 | 0.968 | −2.7e−4 | 1.6e−4 | 7 |
| 29286 | M | " | " | " | " | " | 0.964 | 0.968 | −2.8e−4 | 2.0e−4 | 7 |
| 30321 | M | " | " | " | " | " | 0.961 | 0.969 | −5.0e−4 | −1.8e−4 | 7 |
| 31355 | M | " | " | " | " | " | 0.961 | 0.968 | −2.2e−4 | 2.9e−4 | 7 |
| 32390 | M | " | " | " | " | " | 0.961 | 0.968 | −2.0e−4 | 3.0e−4 | 7 |
| 33425 | M | " | " | " | " | " | 0.961 | 0.968 | −5.1e−4 | 1.3e−5 | 7 |
| 34460 | M | " | " | " | " | " | 1.021 | 1.030 | −8.9e−4 | 4.6e−4 | 7 |
| 35495 | M | " | " | " | " | " | 1.020 | 1.034 | −2.1e−4 | −7.0e−4 | 7 |

These results show that the optimized DPD includes one more cycle with respect to the APD. The values of α and β are approximately less than 1. Thus the improved PD treatment foresees in average a series of cycles with decreasing dwell time $\Delta T_i$, i=1, ..., N together a decreasing volume exchanged $\Delta V_i$, i=1, ..., N−1. The parameters γ and δ seem to play a minor role in the optimization process. In order to put into evidence the differences between the APD and DPD patterns let us show in FIGS. 17*a*-17*b*, the two PD patterns related to the patient with $A_0/\Delta x$ equal to 27216.

This previous analysis has been further developed by drawing the charts of the optimal dialysis therapy within a given range of the plan defined by the axes $V_{tot}$ and $T_{tot}$. At each point defined by the couple $[V_{tot}, T_{tot}]$ we report the [%] increase of $KT/V_{urea}$ relative to DPD with respect to the one of APD. The result is reported below for a specific patient (of type H) in FIG. 18.

This figure puts into evidence that, in the case of optimization of $KT/V_{urea}$, DPD is effective for a large dialysate volume and a small therapy time. On the other hand, in the typical region of peritoneal dialysis (total volume=10=12 liters and total time=400=500 min) the classical automated peritoneal dialysis seems to be the more convenient choice. However, we point out that, in the latter region, the efficiency of the therapy (quantified by $KT/V_{urea}$ and ultrafiltration) is remarkably higher than in the DPD one as showed in FIG. 19.

Similar results are obtained if the optimization target is the ultrafiltration. The increase in ultrafiltration provided by the optimal therapy with respect to a standard APD is reported in FIG. 20.

Nevertheless, we again observe that ultrafiltration is higher in the APD optimality region than in the tidal one.

Finally, we observe that in the tidal optimality region the optimal therapies are of variable type. For example, in the point characterized by $T_{tot}$=300 minutes and $V_{tot}$=14 liters, the optimal values of α, β feature sensible differences from the standard value, equal to 1. Precisely we obtain α=0.88, β=0.95, N=8 that give a profile similar to the DPD profile reported in FIG. 17. The interpretation of the previous phenomena will be made clear by analyzing the effect of the exchange pattern shape and the effect of the realistic pump model separately.

An embodiment of the foregoing is a method for prescribing a dialysis treatment comprising the following steps:
 collecting patient specific data,
 determining at least one target,
 defining a series of values of the type [V;t] which allow to achieve said target wherein V represents the volume of dialysate used and t the duration of treatment, based on said patient specific data,
 displaying said series of values on a map.

In an embodiment of the present invention, the dialysis is a peritoneal dialysis.

In another embodiment, the target is taken from the followings: Ultra-filtration, sodium removal or glucose absorption.

The target is a clearance of a solute taken from the followings: creatinine, urea or microglobuline.

In an embodiment, the series of values is displayed in the form of a continuous curve in an orthogonal bi-dimensional graph.

In a preferred embodiment, the method according to the invention includes the displaying of several series of a values on a map, each series corresponding to a specific target value and defining an isoline on said graph.

In another embodiment, the patient specific data are obtained by a test, such as PET, PDC miniPET or other dialysis tests able to calculate the patient peritoneal membrane characteristics.

In another embodiment, additional information related to at least another patient specific parameter are provided on the map, for instance in the background.

In a preferred embodiment, the other parameter is taken from the followings: sodium removal, glucose absorption, ultra-filtration, protein intake, microglobuline clearance, effect on diet and kidney function.

In an embodiment of the foregoing, the peritoneal dialysis prescription system according to the invention comprises the following elements:
 first processing means for entering patient specific data,
 second processing means for selecting a target,
 third processing means for defining a series of values of the type [V;t] which allow to achieve said target wherein V represents the volume of dialysate used and t the duration of treatment,
 display means adapted for displaying said series of values on a map.

In another embodiment, the display means are adapted to represent said series of values in the form of a continuous curve in an orthogonal bi-dimensional graph.

In a preferred embodiment, the display means are adapted to represent several series of values on a map, each series corresponding to a specific target and defining an isoline on said graph.

In another embodiment, the target is taken from the followings: Ultra-filtration, sodium removal or glucose absorption.

In another embodiment, the target is a clearance of a solute taken from the followings: creatinine, urea or microglobuline.

In another embodiment, the patient specific data are obtained by a test, such as PET, PDC miniPET or other dialysis tests able to calculate the patient membrane characteristics.

In another embodiment, the additional information related to at least another patient specific parameter are provided on the map, for instance in the background.

In a preferred embodiment, the other parameter is taken from the followings: sodium removal, glucose absorption, ultra-filtration, protein intake, microglobuline clearance, effect on diet and kidney function.

In another embodiment, the peritoneal dialysis prescription system according to the invention furthermore comprises display means for displaying the treatment parameters and the expected results for any of said series of values.

In another embodiment, the peritoneal dialysis prescription system according to the invention furthermore comprises automatic parameter recording means which are adapted to automatically record the selected treatment parameters.

Effect of the Realistic Drain Profile

The realistic drain profile penalizes the APD therapies especially when large volumes are injected in short times. Indeed, in this case, the low drain rates at low filling volumes induce a sensible time loss. For this reason, when the realistic pump model is considered, therapies (with an exchange rate of 70-80% of the maximal filling volume at each cycle) are 10% more effective than classical APDs for $V_{tot}$>12 liters and $T_{tot}$>7 hours. This point has been showed in FIG. 18. On the opposite, if the ideal pump model is considered, the classical 100% exchange APD results to be the optimal therapy for most combinations of $V_{tot}$ and $T_{tot}$.

The DPD optimality region is sensibly restricted with respect to the real pump model, as reported in FIG. 22 for the α, β, γ, δ pattern. Moreover, the gain produced by the DPD profile is reduced with respect to the case of realistic drain profile (compare FIGS. 18 and 22). The same patient has been used in order to produce the results summarized below. This region is characterized by extremely large volumes (>14 liters) and short therapy durations ($T_{tot}$<300 minutes=5 hours). In this case, the effectiveness of DPD (or the loss of performance od APD) can be explained by the influence of the direct dependence of the peritoneal transport properties (governed by $A0/\Delta x$) with respect to the peritoneal filling ratio ($V_d(t)/V_{max}$). When large volumes have to be exchanged in short times, most of the therapy consists in exchanging volume. In this situation, the peritoneum is not filled and, according to the aforementioned model, the exchange of chemicals urea, glucose etc. . . . ) is not optimal. Consequently, increasing the number of cycles (eventually in a variable way) results in an increase of performance.

This situation does not change substantially with different glucose concentration into the dialysate.

The latter plots have been obtained with the lowest concentration (1:36%). However similar results are reported in FIG. 23 for the highest one (3.86%).

Effect of Variation of Pattern Shape from Standard APD

These tests are designed to put into evidence the effect on the therapy performance ($KT/V_{urea}$ or ultrafiltration) of the cycle frequency (governed by the parameter $\alpha$) and of the ratio of volume exchanged (governed by the parameter $\beta$). In particular, we describe two tests. In the first test we consider a pattern consisting in three cycles, where 6 liters of dialysate are exchanged in a total time of 500 minutes. The only parameter that changes is $\alpha$, this means that we are analyzing several ways for partitioning the total therapy time in three parts. This test puts into evidence that the maximal performance is obtained when the dwell times are slightly decreasing, that means $\alpha$<1. FIG. 24 summarizes the results.

In the second test we consider a pattern consisting in four cycles, where 7.4 liters of dialysate are exchanged in a total time of 500 minutes using 6 cycles. We analyze the effect of the distribution of the total volume among the cycles. The variation of the parameter $\beta$ defines the repartition of the total volume among each cycle. We observe that, again, the strategy of equal repartition seems to be suboptimal. FIG. 25 summarizes the results.

Overall these two tests show that for a given PD therapy a different set up of dwell time and volume with respect standard therapies could provide a better performance. The numerical investigations introduced and discussed in the previous sections suggest the following considerations:
1. the rate of gain of optimization is high in regions that are not customarily used,
2. better efficiency is achieved for these combinations of volumes ($V_{tot}$) and durations ($T_{tot}$) that are most commonly adopted in nowadays clinics,
3. the above conclusions are target indifferent,
4. the Dynamic Peritoneal Dialysis (DPD) is effective when:
    most of the time of the therapy must be spent in exchanging the dialysate to/from the peritoneal cavity,
    the pump injection and drain rate is slow or penalized.

Optimal Control by the Switched System Method

This section deals with the numerical tests related to the PD optimization method for switched system. In this case, the methods takes into account all the degrees of freedom (dof) of the system which are 2(N−1) we have a way to verify the parametrization of the control function with $a=[\alpha, \beta, \gamma, \delta]$. All the simulations are performed using the kinetic model of Pyle-Popovich including the kinetic of urea and glucose through the two compartments (b) and (a). Let us consider a PD therapy as follows:

$$T_{tot}=420[\min],$$

$$V_{tot}=4[l],$$

$$V_{max}=2.001[l],$$

$$V_{min}=1[ml],$$

$$N=3,$$

$$\alpha=1.4,$$

$$\beta=1,$$

$$\gamma=0$$

$$\delta=0 \quad (5)$$

The PD profile corresponding to previous data is showed in FIG. 26. The patient characteristics are taken from the paper of Vonesh [E. F. Vonesh, M. J. Lysaght, J. Moran, and P. Farrell, *Kinetic modeling as a prescription aid in peritoneal dialysis*, Blood Purif. 9 (1991), 246-270]. This is an applied example but the same procedure can be used to check the optimality of different PD profile. We recall that the procedure is based on a gradient algorithm and is able to provide detailed information related to all the switching instants of the PD profile. Thus we can assure that a local approximation of the optimal switching sequence is found trying to satisfy the classical first order conditions. Things would be different in the case where it is possible to assure the convexity of the index of performance ($E_{ff}$) with respect to the control (t). In fact, in this case we can be sure that the algorithm approximates the global maximizer. Unfortunately this is not our case.

All the information produced during the process is collected in the next table for each iteration.

Let us introduce the following notation to explain and interpret the results:

$\nabla_t(E_{ff})$ is the gradient of ($E_{ff}$) with respect to the dof. Precisely, we approximate the optimal switching instant sequence with respect to the urea extraction represented by the index $KT/V_{urea}$, $$\frac{\partial E_{ff}}{\partial t_i}(\|)$$

is the componentwise projection of ($\nabla_t E_{ff}$) along the parallel direction to the inequality constraints. This information is helpful to put into evidence the trend of the optimization with respect to the dwell time sequence.

$$\frac{\partial E_{ff}}{\partial t_i}(\perp)$$

is the componentwise projection of ($\nabla_t E_{ff}$) along the perpendicular direction to the inequality constraints. This information is helpful to put into evidence the trend of the optimization with respect to the sequence of volume exchanged in each cycle.

$$\frac{\partial E_{\!f\!f_A}}{\partial t_i} \quad 5$$

is the gradient of $E_{\!f\!f_A}$ which represents the augmented Lagrangian function obtained by adding the equality constraint related to $V_{tot}$, $$\frac{\partial E_{\!f\!f_A}}{\partial t_i}(\perp) \quad 10$$

is the componentwise projection $\nabla_t(E_{\!f\!f_A})$ along the direction perpendicular to the inequality constraints.

$$\frac{\partial E_{\!f\!f_A}}{\partial t_i}(\|)$$

is the componentwise projection $\nabla_t(E_{\!f\!f_A})$ along the inequality constraints when they become active.

| col. iter. | 1<br>$\nabla_t(E_{\!f\!f})$ | 2<br>$t_2$ | 3<br>$t_3$ | 4<br>$t_4$ | 5<br>$V_1$ | 6<br>$t_5$ | 7<br>$t_6$ | 8<br>$t_7$ | 9<br>$V_2$ |
|---|---|---|---|---|---|---|---|---|---|
| 1 | $\frac{\partial E_{\!f\!f}}{\partial t_i}$ | −1.0402e−2 | −3.4669e−3 | 3.4682e−3 | 1.00 | −1.2696e−2 | −4.2320e−3 | 4.2318e−3 | 1.00 |
|  | $\frac{\partial E_{\!f\!f}}{\partial t_i}(\perp)$ | −1.0403e−2 | −3.4676e−3 | 3.4676e−3 | 1.00 | −1.2696e−2 | −4.2319e−3 | 4.2319e−3 | 1.00 |
|  | $\frac{\partial E_{\!f\!f}}{\partial t_i}(\|)$ | 6.5079e−7 | 6.5079e−7 | 6.5079e−7 | 1.00 | −8.5888e−8 | −8.5888e−8 | −8.5888e−8 | 1.00 |
|  | $\frac{\partial E_{\!f\!f_A}}{\partial t_i}$ | 1.2039e−3 | 4.0174e−4 | −4.0044e−4 | 1.00 | −1.0898e−3 | −3.6333e−4 | 3.6316e−4 | 1.00 |
|  | $\frac{\partial E_{\!f\!f_A}}{\partial t_i}(\perp)$ | 1.2033e−3 | 4.0109e−4 | −4.0109e−4 | 1.00 | −1.0897e−3 | −3.6324e−4 | 3.6324e−4 | 1.00 |
|  | $\frac{\partial E_{\!f\!f_A}}{\partial t_i}(\|)$ | — | — | — | — | — | — | — | — |
| 2 | $\frac{\partial E_{\!f\!f}}{\partial t_i}$ | −1.0495e−2 | −3.4981e−3 | 3.4989e−3 | 0.79 | −1.2794e−2 | −4.2646e−3 | 4.2644e−3 | 1.19 |
|  | $\frac{\partial E_{\!f\!f}}{\partial t_i}(\perp)$ | −1.0496e−2 | −3.4985e−3 | 3.4985e−3 | 0.79 | −1.2794e−2 | −4.2645e−3 | 4.2645e−3 | 1.19 |
|  | $\frac{\partial E_{\!f\!f}}{\partial t_i}(\|)$ | 4.1595e−7 | 4.1595e−7 | 4.1595e−7 | 0.79 | −1.3863e−7 | −1.3863e−7 | −1.3863e−7 | 1.19 |
|  | $\frac{\partial E_{\!f\!f_A}}{\partial t_i}$ | 1.0813e−3 | 3.6070e−4 | −3.5987e−4 | 0.79 | −1.2173e−3 | −4.0585e−4 | 4.0557e−4 | 1.19 |
|  | $\frac{\partial E_{\!f\!f_A}}{\partial t_i}(\perp)$ | 1.0809e−3 | 3.6028e−4 | −3.6028e−4 | 0.79 | −1.2171e−3 | −4.0571e−4 | 4.0571e−4 | 1.19 |
|  | $\frac{\partial E_{\!f\!f_A}}{\partial t_i}(\|)$ | — | — | — | — | — | — | — | — |
| 3 | $\frac{\partial E_{\!f\!f}}{\partial t_i}$ | −1.0563e−2 | −3.5207e−3 | 3.5212e−3 | 0.60 | −1.2797e−2 | −4.2658e−3 | 4.2654e−3 | 1.40 |
|  | $\frac{\partial E_{\!f\!f}}{\partial t_i}(\perp)$ | −1.0563e−2 | −3.5209e−3 | 3.5209e−3 | 0.60 | −1.2797e−2 | −4.2656e−3 | 4.2656e−3 | 1.40 |
|  | $\frac{\partial E_{\!f\!f}}{\partial t_i}(\|)$ | 2.4029e−7 | 2.4029e−7 | 2.4029e−7 | 0.60 | −1.9545e−7 | −1.9545e−7 | −1.9545e−7 | 1.40 |
|  | $\frac{\partial E_{\!f\!f_A}}{\partial t_i}$ | 1.0203e−3 | 3.4025e−4 | −3.3977e−4 | 0.60 | −1.2142e−3 | −4.0487e−4 | 4.0448e−4 | 1.40 |
|  | $\frac{\partial E_{\!f\!f_A}}{\partial t_i}(\perp)$ | 1.0200e−3 | 3.4001e−4 | −3.4001e−4 | 0.60 | −1.2140e−3 | −4.0467e−4 | 4.0467e−4 | 1.40 |
|  | $\frac{\partial E_{\!f\!f_A}}{\partial t_i}(\|)$ | — | — | — | — | — | — | — | — |
| 4 | $\frac{\partial E_{\!f\!f}}{\partial t_i}$ | −1.0618e−2 | −3.5393e−3 | 3.5395e−3 | 0.42 | −1.2691e−2 | −4.2306e−3 | 4.2301e−3 | 1.62 |
|  | $\frac{\partial E_{\!f\!f}}{\partial t_i}(\perp)$ | −1.0618e−2 | −3.5394e−3 | 3.5394e−3 | 0.42 | −1.2691e−2 | −4.2304e−3 | 4.2304e−3 | 1.62 |
|  | $\frac{\partial E_{\!f\!f}}{\partial t_i}(\|)$ | 1.0512e−7 | 1.0512e−7 | 1.0512e−7 | 0.42 | −2.5582e−7 | −2.5582e−7 | −2.5582e−7 | 1.62 |
|  | $\frac{\partial E_{\!f\!f_A}}{\partial t_i}$ | 1.0219e−3 | 3.4071e−4 | −3.4050e−4 | 0.42 | −1.0515e−3 | −3.5067e−4 | 3.5016e−4 | 1.62 |

-continued

| col. iter. | 1 $V_i(E_{ff})$ | 2 $t_2$ | 3 $t_3$ | 4 $t_4$ | 5 $V_1$ | 6 $t_5$ | 7 $t_6$ | 8 $t_7$ | 9 $V_2$ |
|---|---|---|---|---|---|---|---|---|---|
| | $\frac{\partial E_{ff_A}}{\partial t_i}(\perp)$ | 1.0218e−3 | 3.4061e−4 | −3.4061e−4 | 0.42 | −1.0512e−3 | −3.5041e−4 | 3.5041e−4 | 1.62 |
| | $\frac{\partial E_{ff_A}}{\partial t_i}(\parallel)$ | — | — | — | — | — | — | — | — |
| 5 | $\frac{\partial E_{ff}}{\partial t_i}$ | −1.0671e−2 | −3.5569e−3 | 3.5569e−3 | 0.22 | −1.2430e−2 | −4.1435e−3 | 4.1429e−3 | 1.82 |
| | $\frac{\partial E_{ff}}{\partial t_i}(\perp)$ | −1.0671e−2 | −3.5569e−3 | 3.5569e−3 | 0.22 | −1.2430e−2 | −4.1432e−3 | 4.1432e−3 | 1.82 |
| | $\frac{\partial E_{ff}}{\partial t_i}(\parallel)$ | 1.0302e−8 | 1.0302e−8 | 1.0302e−8 | 0.22 | −3.2239e−7 | −3.2239e−7 | −3.2239e−7 | 1.82 |
| | $\frac{\partial E_{ff_A}}{\partial t_i}$ | 1.0494e−3 | 3.4980e−4 | −3.4978e−4 | 0.22 | −7.0984e−4 | −2.3683e−4 | 2.3618e−4 | 1.82 |
| | $\frac{\partial E_{ff_A}}{\partial t_i}(\perp)$ | 1.0494e−3 | 3.4979e−4 | −3.4979e−4 | 0.22 | −7.0952e−4 | −2.3651e−4 | 2.3651e−4 | 1.82 |
| | $\frac{\partial E_{ff_A}}{\partial t_i}(\parallel)$ | — | — | — | — | — | — | — | — |
| 6 | $\frac{\partial E_{ff}}{\partial t_i}$ | −1.0716e−2 | −3.5720e−3 | 3.5720e−3 | 0.02 | −1.1914e−2 | −3.9717e−3 | 3.9709e−3 | 1.98 |
| | $\frac{\partial E_{ff}}{\partial t_i}(\perp)$ | −1.0716e−2 | −3.5720e−3 | 3.5720e−3 | 0.02 | −1.1914e−2 | −3.9713e−3 | 3.9713e−3 | 1.98 |
| | $\frac{\partial E_{ff}}{\partial t_i}(\parallel)$ | −1.7372e−8 | −1.7372e−8 | −1.7372e−8 | 0.02 | −3.8904e−7 | −3.8904e−7 | −3.8904e−7 | 1.98 |
| | $\frac{\partial E_{ff_A}}{\partial t_i}$ | 9.2240e−4 | 3.0746e−4 | −3.0749e−4 | 0.02 | −2.7589e−4 | −9.2224e−5 | 9.1445e−5 | 1.98 |
| | $\frac{\partial E_{ff_A}}{\partial t_i}(\perp)$ | 9.2242e−4 | 3.0747e−4 | −3.0747e−4 | 0.02 | −2.7550e−4 | −9.1834e−5 | 9.1834e−5 | 1.98 |
| | $\frac{\partial E_{ff_A}}{\partial t_i}(\parallel)$ | −1.7372e−8 | −1.7372e−8 | −1.7372e−8 | 0.02 | — | — | — | — |
| 7 | $\frac{\partial E_{ff}}{\partial t_i}$ | −1.0716e−2 | −3.5720e−3 | 3.5719e−3 | 0.02 | −1.1768e−2 | −3.9229e−3 | 3.9221e−3 | 2.00 |
| | $\frac{\partial E_{ff}}{\partial t_i}(\perp)$ | −1.0716e−2 | −3.5720e−3 | 3.5720e−3 | 0.02 | −1.1768e−2 | −3.9225e−3 | 3.9225e−3 | 2.00 |
| | $\frac{\partial E_{ff}}{\partial t_i}(\parallel)$ | −1.8867e−8 | −1.8867e−8 | −1.8867e−8 | 0.02 | −3.7509e−7 | −3.7509e−7 | −3.7509e−7 | 2.00 |
| | $\frac{\partial E_{ff_A}}{\partial t_i}$ | 9.6238e−4 | 3.2078e−4 | −3.2082e−4 | 0.02 | −8.9599e−5 | −3.0116e−5 | 2.9366e−5 | 2.00 |
| | $\frac{\partial E_{ff_A}}{\partial t_i}(\perp)$ | 9.6240e−4 | 3.2080e−4 | −3.2080e−4 | 0.02 | −8.9224e−5 | −2.9741e−5 | 2.9741e−5 | 2.00 |
| | $\frac{\partial E_{ff_A}}{\partial t_i}(\parallel)$ | −1.8867e−8 | −1.8867e−8 | −1.8867e−8 | 0.02 | −7.0711e−1 | −7.0711e−1 | −7.0711e−1 | 2.00 |
| 8 | $\frac{\partial E_{ff}}{\partial t_i}$ | −1.0716e−2 | −3.5720e−3 | 3.5719e−3 | 0.02 | −1.1768e−2 | −3.9229e−3 | 3.9221e−3 | 2.00 |
| | $\frac{\partial E_{ff}}{\partial t_i}(\perp)$ | −1.0716e−2 | −3.5720e−3 | 3.5720e−3 | 0.02 | −1.1768e−2 | −3.9225e−3 | 3.9225e−3 | 2.00 |
| | $\frac{\partial E_{ff}}{\partial t_i}(\parallel)$ | −1.8867e−8 | −1.8867e−8 | −1.8867e−8 | 0.02 | −3.7507e−7 | −3.7507e−7 | −3.7507e−7 | 2.00 |
| | $\frac{\partial E_{ff_A}}{\partial t_i}$ | 9.6238e−4 | 3.2078e−4 | −3.2082e−4 | 0.02 | −8.9588e−5 | −3.0113e−5 | 2.9363e−5 | 2.00 |
| | $\frac{\partial E_{ff_A}}{\partial t_i}(\perp)$ | 9.6240e−4 | 3.2080e−4 | −3.2080e−4 | 0.02 | −8.9213e−5 | −2.9738e−5 | 2.9738e−5 | 2.00 |
| | $\frac{\partial E_{ff_A}}{\partial t_i}(\parallel)$ | −1.8867e−8 | −1.8867e−8 | −1.8867e−8 | 0.02 | −7.0711e−1 | −7.0711e−1 | −7.0711e−1 | 2.00 |
| 9 | $\frac{\partial E_{ff}}{\partial t_i}$ | −1.0716e−2 | −3.5720e−3 | 3.5719e−3 | 0.02 | −1.1768e−2 | −3.9229e−3 | 3.9221e−3 | 2.00 |

-continued

| col. iter. | 1 $\nabla_t(E_{ff})$ | 2 $t_2$ | 3 $t_3$ | 4 $t_4$ | 5 $V_1$ | 6 $t_5$ | 7 $t_6$ | 8 $t_7$ | 9 $V_2$ |
|---|---|---|---|---|---|---|---|---|---|
| | $\frac{\partial E_{ff}}{\partial t_i}(\perp)$ | −1.0716e−2 | −3.5720e−3 | 3.5720e−3 | 0.02 | −1.1767e−2 | −3.9225e−3 | 3.9225e−3 | 2.00 |
| | $\frac{\partial E_{ff}}{\partial t_i}(\parallel)$ | −1.8868e−8 | −1.8868e−8 | −1.8868e−8 | 0.02 | −3.7505e−7 | −3.7505e−7 | −3.7505e−7 | 2.00 |
| | $\frac{\partial E_{ff_A}}{\partial t_i}$ | 1.0063e−3 | 3.3542e−4 | −3.3546e−4 | 0.02 | −4.5654e−5 | −1.5468e−5 | 1.4718e−5 | 2.00 |
| | $\frac{\partial E_{ff_A}}{\partial t_i}(\perp)$ | 1.0063e−3 | 3.3544e−4 | −3.3544e−4 | 0.02 | −4.5279e−5 | −1.5093e−5 | 1.5093e−5 | 2.00 |
| | $\frac{\partial E_{ff_A}}{\partial t_i}(\parallel)$ | −1.8868e−8 | −1.8868e−8 | −1.8868e−8 | 0.02 | −7.0711e−1 | −7.0711e−1 | −7.0711e−1 | 2.00 |
| 10 | $\frac{\partial E_{ff}}{\partial t_i}$ | −1.0716e−2 | −3.5720e−3 | 3.5719e−3 | 0.02 | −1.1768e−2 | −3.9229e−3 | 3.9221e−3 | 2.00 |
| | $\frac{\partial E_{ff}}{\partial t_i}(\perp)$ | −1.0716e−2 | −3.5720e−3 | 3.5720e−3 | 0.02 | −1.1767e−2 | −3.9225e−3 | 3.9225e−3 | 2.00 |
| | $\frac{\partial E_{ff}}{\partial t_i}(\parallel)$ | −1.8868e−8 | −1.8868e−8 | −1.8868e−8 | 0.02 | −3.7503e−7 | −3.7503e−7 | −3.7503e−7 | 2.00 |
| | $\frac{\partial E_{ff_A}}{\partial t_i}$ | 1.0063e−3 | 3.3542e−4 | −3.3546e−4 | 0.02 | −4.5644e−5 | −1.5465e−5 | 1.4715e−5 | 2.00 |
| | $\frac{\partial E_{ff_A}}{\partial t_i}(\perp)$ | 1.0063e−3 | 3.3544e−4 | −3.3544e−4 | 0.02 | −4.5269e−5 | −1.5090e−5 | 1.5090e−5 | 2.00 |
| | $\frac{\partial E_{ff_A}}{\partial t_i}(\parallel)$ | −1.8868e−8 | −1.8868e−8 | −1.8868e−8 | 0.02 | −7.0711e−1 | −7.0711e−1 | −7.0711e−1 | 2.00 |

To simplify the reading of the data let us consider FIGS. 27a-27b where the switching instants are denoted according to the notation used in the previous table. The arrows denote the gradient with respect to the switching instants and are related to the first iteration. The arrows (→) and (←) denote respectively a positive and a negative gradient component.

Let us make a comment on the results related to the first iteration and concerning the sensitivity of $E_{ff}$ without taking into account the equality constraint ($V_{tot}$ is fixed). FIG. 27a represents the results.

$$\frac{\partial E_{ff}}{\partial t_3} < 0 \text{ and } \frac{\partial E_{ff}}{\partial t_4} > 0$$

consequently the method suggests to increase the volume of dialysate exchanged in the first cycle. The same situation is recognized if we focus our attention on the second cycle. Of course this is not possible because we need to satisfy the constraint on the total dialysate ($V_{tot}$) used. This is right because these values do not take into account the equality constraint and means that the PD performance can be improved by using more dialysate. The sensitivity of $E_{ff}$ with respect to the switching sequence t has order $10^{-3}$.

The projection of $\nabla_t(E_{ff})$ in the direction perpendicular to the inequality constraint, supposed active is $$\frac{\partial E_{ff}}{\partial t_3}(\perp) < 0 \text{ and } \frac{\partial E_{ff}}{\partial t_4}(\perp) > 0.$$

The second cycle has the same behavior. This means that this projection suggests to increase the dialysate exchanged. The sensitivity in this direction has order $10^{-3}$. The order is the same of the previous one but we get a specific evaluation of its relevance with respect to the perpendicular direction which is related only to the dialysate exchanged in a cycle.

The projection of $\nabla_t(E_{ff})$ in the direction parallel to the inequality constraint (supposed active) is $$\frac{\partial E_{ff}}{\partial t_i}(\parallel) > 0, i = 2, \ldots, 4.$$

This means that the algorithm suggests to translate the switching sequence augmenting the dwell time of the first cycle. The sensitivity in this direction has order $10^{-7}$. Similar considerations can be proposed for the second cycle. Indeed there is a difference because in this case $$\frac{\partial E_{ff}}{\partial t_i}(\parallel) < 0, i = 5, \ldots, 7.$$

The sensitivity in this direction has order $10^{-8}$. This means that the algorithm suggests to enlarge the third dwell time in order to improve the performance. We point out that a final comment related to the dwell time tuning will be possible at the end of the process.

The sensitivity of $E_{ff}$ with respect to the volume exchanged has 4 orders of magnitude more than the sensitivity with respect to the tuning of the dwell time (determined by the parallel component of the gradient with respect to the constraint). Thus we can expect a variation on the volume exchange bigger than the variation on the dwell time after the first iteration. Indeed, this is true for each step of the gradient algorithm as showed by the data provided in the previous table for all the iterations.

Now let us make a comment on the results related to the sensitivity of $E_{ff_A}$ which is the augmented lagrangian function including the total dialysate constraint ($V_{tot}$). The comments are related to the first iteration.

$$\frac{\partial E_{ff_A}}{\partial t_3} > \text{ and } \frac{\partial E_{ff_A}}{\partial t_4} < 0$$

consequently the method suggests to reduce the volume of dialysate exchanged in the first cycle. The opposite situation is recognized for the second cycle for which we get $$\frac{\partial E_{ff_A}}{\partial t_7} < 0 \text{ and } \frac{\partial E_{ff_A}}{\partial t_8} > 0.$$

The effect of the equality constraint on $V_{tot}$ becomes evident. One hand the algorithm suggests to reduce the volume used in the first cycle and on the other hand to increase the dialysate exchanged in the second cycle to satisfy the constraint and improve the PD performance. The sensitivity of $E_{ff_A}$ with respect to the switching sequence t has order $10^{-4}$.

The projection of $\nabla_t(E_{ff_A})$ in the direction perpendicular to the inequality constraint is $$\frac{\partial E_{ff_A}}{\partial t_3}(\perp) > 0 \text{ and } \frac{\partial E_{ff_A}}{\partial t_4}(\perp) < 0.$$

The opposite situation is recognized for the second 102 cycle for which we get $$\frac{\partial E_{ff_A}}{\partial t_7}(\perp) < 0 \text{ and } \frac{\partial E_{ff_A}}{\partial t_8}(\perp) > 0.$$

The sensitivity of $E_{ff_A}(\perp)$ with respect to the switching sequence t has order $10^{-4}$. We can make the same comment reported in the previous point.

The projection of $\nabla_t(E_{ff_A})$ in the direction parallel to the inequality constraint is $$\frac{\partial E_{ff_A}}{\partial t}(\|)$$

is not showed because at the first iteration the inequality constraints are not active and thus the switching sequence is updated according to $$\frac{\partial E_{ff_A}}{\partial t}.$$

This is the situation for both the first and the second cycle.

The sensitivity of $E_{ff_A}$ has 1 order of magnitude less than $E_{ff}$. Moreover, if we compare $$\frac{\partial E_{ff_A}}{\partial t} \text{ with } \frac{\partial E_{ff_A}}{\partial t}(\perp)$$

we can see again that the component parallel to the inequality constraint must be many order smaller than the perpendicular direction just as in the case of $E_{ff}$.

Let us make a comment on the results related to the last iteration and concerning the sensitivity of $E_{ff}$. FIG. 28b represents the results.

We make a comment on the results related to the last iteration and concerning the sensitivity of $E_{ff}$. FIG. 28a represent the results.

$$\frac{\partial E_{ff}}{\partial t_3} < 0 \text{ and } \frac{\partial E_{ff}}{\partial t_4} > 0$$

consequently the method suggests to augment the volume of dialysate exchanged in the first cycle. The same situation is recognized if we focus our attention on the second cycle where $$\frac{\partial E_{ff}}{\partial t_7} < 0 \text{ and } \frac{\partial E_{ff}}{\partial t_8} > 0.$$

Thus without taking into account the equality constraints the comments proposed for the first iteration are still valid. The sensitivity has order $10^{-3}$.

The projection of $\nabla_t(E_{ff})$ in the direction perpendicular to the inequality constraint of the quantities computed suggests to increase the dialysate used in both the cycle like the first iteration.

The projection of $\nabla_t(E_{ff})$ in the direction parallel to the inequality constraint $$\frac{\partial E_{ff}}{\partial t_i}(\|), i = 2, \ldots, 7$$

is negative. This means that the algorithm suggests to translate the switching sequence decreasing the first dwell time and increasing the last one. The sensitivity in this direction has order $10^{-8}$ and $10^{-7}$ respectively for the first and second cycle. Thus the tuning of the third dwell is more relevant than the first one.

Now we make a comment on the results related to the sensitivity of $E_{ff_A}$. The comments are related to the last iteration.

$$\frac{\partial E_{ff_A}}{\partial t_3} > \text{ and } \frac{\partial E_{ff_A}}{\partial t_4} < 0$$

consequently the method suggests to reduce the volume of dialysate exchanged in the first cycle. The opposite situation is recognized for the second cycle for which we get $$\frac{\partial E_{ff_A}}{\partial t_7} < 0 \text{ and } \frac{\partial E_{ff_A}}{\partial t_8} > 0.$$

The sensitivity of $E_{ff_A}$ with respect to the switching sequence t has order $10^{-4}$.

The projection of $\nabla_t(E_{ff_A})$ in the direction perpendicular to the inequality constraint is $$\frac{\partial E_{ff_A}}{\partial t_3}(\perp) > 0 \text{ and } \frac{\partial E_{ff_A}}{\partial t_4}(\perp) < 0.$$

To sum up we can make the same comment reported in the previous point.

The projection of $\nabla_t(E_{ff_A})$ in the direction parallel to the inequality constraint is negative, $$\frac{\partial E_{ff_A}}{\partial t}(\|) < 0.$$

The computed data related to the second cycle have order $10^{-1}$ which is 7 times higher that the first cycle.

The sensitivity of $E_{ff_A}$ has 1 order less than $E_{ff}$. Moreover, if we compare $$\frac{\partial E_{ff_A}}{\partial t} \text{ with } \frac{\partial E_{ff_A}}{\partial t}(\perp)$$

we can see that the component parallel to the inequality constraint must be many order smaller than the perpendicular direction just as in the case of $E_{ff}$.

According to the previous results, the optimal PD profile corresponds to the one which uses the minimum of cycles in order to exploit all the available dialysate. In fact the V1 is driven approximately to zero and V2 to 2 liters. Moreover, the numerical results show that the magnitude of $E_{ff}$ projected along the direction parallel to the inequality constraint is small, approximately $10^{-8}$.

In this procedure we neglect the real drain profile and consequently the optimal solution corresponds to a full (100%) exchange in each cycle. This circumstance can be detected from the fact that at each iteration and in all the cycles needed to use the diyalisate we have $$\frac{\partial E_{ff}}{\partial t_i} < 0 \text{ and } \frac{\partial E_{ff}}{\partial t_{i+1}} > 0.$$

This means that the algorithm suggests us to exchange the highest volume possible. Thus when possible the best PD performance is reached exchanging the maximum amount of dialysate possible in each cycle. In order to summarize the results FIG. 29 show the PD profile corresponding to the switching sequence t obtained at the last iteration. We observe that the dwell sequence is changed. Precisely the last dwell time is reduced with respect to the starting PD profile ($\alpha=1.4>1$). Similar results can be obtained applying the method to a different PD profile. On one side these results confirm the good quality of the parametrization used. In fact, even if here we use a larger representation including all the dof of the problem the results confirm the answer obtained by the parametrization. On the other side the algorithm state clearly that the PD improvement can be obtained by a tuning of dwell time adapted to the patient and avoiding the penalization of the real drain profile. The pump device is able to produce injection-dwell-extraction sequences according to the results obtained by the model becoming a tool to treat at the best the patients submitted to PD.

Glucose Management

We propose here a procedure to exploit the capabilities of the pump to deal with several bags of dialysate of different glucose concentrations. In particular, we present a strategy to determine the choice of the bags of dialysate in order to fulfill a suitable target on ultrafiltration and minimize the patient's exposure to glucose. Indeed, clinicians face the very difficult question of determining the suitable balance between providing an adequate ultrafiltration and limiting the blood glycaemia that on the short term perturbs the patient's metabolism and on the long term can induce unfavorable changes on the peritoneal transport characteristics. The aim of the optimization procedure proposed here is to provide a computational tool to better handle this matter. The complete protocol that manages the glucose charge is split in two parts:

the minimization of glucose exposure,
the optimization by variable glucose concentration.

Minimization of Glucose Exposure

Our aim is to determine the minimum level of glucose of the fresh dialysate to fulfill some given targets, as for instance a specified $KT/V_{urea}$ or ultrafiltration. In this case, we consider the duration of the therapy and the total volume of dialysate as a priori given quantities. Indeed, these parameters are strongly connected with the economical cost and to the discomfort of the therapy, thus they are not only determined by medical considerations but also by financial constraints, e.g. the level of refund provided by medical insurances.

To fulfill the task of minimization of glucose exposure we propose the following sequence of steps:

1. determination of a range of admissible glucose levels,
2. determination of the optimum glucose level,
3. identification of the set of bags that best approximates the optimum.

Determination of a Range of Admissible Glucose Levels

Let $g_{min}$ and $g_{max}$ be the minimal and maximal glucose concentrations of the dialysate on the market. Typically $g_{min}=1.36\%$ and $g_{max}=3.86\%$. Often, the intermediate value $g_2=2.27\%$ is used too. Furthermore, let us denote with $V_{tot}$ (the total volume of dialysate), $T_{tot}$ (the duration of the therapy) and $V_{max}$ (the maximal volume to be filled in the patient) the characteristic parameters defining the therapy prescribed to a patient.

Then, we introduce a range of admissible glucose concentrations, denoted with g, such that $g_{min} \leq g \leq g_{max}$. Secondly, we compute the minimal number of cycles necessary to exploit all the available dialysate. Precisely, we define $N_{min}$=ceil $(V_{tot}/V_{max}$ (where ceil(x) denotes the integer approximating x from the top). By this way, we associate to each admissible glucose concentration a standard therapy defined by $N_{min}$ uniform cycles where a uniform glucose concentration g is injected in the patient.

By means of numerical simulations we aim to find out which of these therapies satisfies suitable targets and minimizes the glucose exposure of the patient.

Determination of the Optimal Glucose Level

First of all, let us define admissible targets to be achieved by tuning the glucose concentration. Possible candidates are KT/V, ultrafiltration and creatinine clearance. The trend of those targets with respect to glucose is very similar as showed before. However, clinicians seem to be more used to consider the relationship between ultrafiltration and glucose concentration. For this reason, in this preliminary study, we neglect the impact of KT/V urea and creatinine clearance. We observe finally that the chosen target must be reachable at least with the maximal glucose concentration available, namely $g_{max}=3.86\%$.

Let us denote the chosen target with $\overline{UF}$, furthermore $UF(g)$ the value of ultrafiltration obtained with the therapy characterized by the glucose concentration g. Finally, let us denote with $g_b$ the glycaemia at the end of the therapy. We observe that $g_b$ quantifies the glucose exposure. These quantities are all provided by the numerical simulation software.

Then, we observe that the efficiency of the therapy identified by g is inversely proportional to the following factors:
- distance of $UF(g)$ to $\overline{UF}$.
- glucose exposure $g_b$.

Consequently, we define the following efficiency function, $$E_{ff}(g) = (UF(g) - \overline{UF})^2 + g_b^2.$$

Our aim is to find the optimal glucose concentration g* that minimizes $E_{ff}(g)$. More precisely, the glucose concentration g* defined such that, $$E_{ff}(g^*) = \min_{g_{min} \leq g \leq g_{max}} \left[ (UF(g) - \overline{UF})^2 + g_b^2 \right].$$

This is a minimization problem with respect to one degree of freedom, namely g. It can be thus solved by applying the minimization algorithm already tested for the optimization of the DPD profile. We finally observe that, in the algorithm presented above, the target $\overline{UF}$ refers to the ultrafiltration of the treatment during the night. This is the most straightforward approach, however the strategy can also be adapted in order to manage a target on the total ultrafiltration of the daily and nightly treatment.

Identification of the Set of Bags that Best Approximates the Optimum

We observe that in the practice of peritoneal dialysis only a few concentrations of glucose are available for the bags of fresh dialysate. We address here the problem of identifying the optimal combination of bags that ensures a glucose content equivalent to the desired one, defined by g*.

To start with, we introduce the following assumptions and definitions:
- only two sets of bags with different glucose concentration can be simultaneously connected to the cycler.
- each bag of dialysate can be filled with different glucose concentrations, denoted with $g_1 < g_2 < \ldots < g_M$. Typically, in peritoneal dialysis M=3 and $g_1$=1.36%, $g_2$=2.27% and $g_3$=3.86%.
- we introduce g' and g", with g'<g", which represent the glucose concentrations associated to the two sets of bags connected to the cycler. Given the optimal glucose concentration g*, these values are chosen among $g_1, g_2, \ldots g_M$ such that, $$g' = \max_{i=1,\ldots,M} [g_i \text{ with } g_i < g^*],$$

if $g^* = g_1$, then $g' = g_1$, $g'' = g_2$, $$g'' = \min_{i=1,\ldots,M} [g_i \text{ with } g_i \geq g^*].$$

This procedure ensures that it will be always possible to obtain a mixture of dialysate at concentrations g' and g" that provides the optimal glucose level g.

let V' and V" be the volumes of dialysate associated to each set of bags. These are the unknowns that we would like to determine at this step.

The volumes V' and V" are directly determined by the constraints arising from the mass conservation principle applied to the dialysate volume and to the mass of glucose. Indeed, let $G_{tot} = V_{tot} \cdot g^*$ be the amount of glucose casted in the dialysate at the optimal glucose level g*. Then, by virtue of the mass conservation principle we require, $$\begin{cases} V' + V'' = V_{tot}, \\ g'V' + g''V'' = G_{tot}, \end{cases}$$

that uniquely determines V' and V" such that, $$\begin{cases} V' = \dfrac{g'' - g^*}{g'' - g'} V_{tot}, \\ V'' = \dfrac{g^* - g'}{g'' - g'} V_{tot}, \end{cases}$$

that is always acceptable since $g' \leq g^* \leq g''$ by definition.

We have now determined that the optimal glucose concentration, identified by the uniform concentration g*, is provided by setting V' liters of fresh dialysate at the concentration g' and V" liters at the concentration g", where both g' and g" correspond to concentration values available on the market.

The limit of this procedure consists in the fact that the volumes V' and V" do not necessarily correspond to the ones that can be obtained by sets of bags on the market. As a consequence of this, the application of the optimal result to clinical cases requires the approximation of the optimal solution with the one that is achievable by the sets of bags in use in his clinical center. At a more evolved development stage, the database of the available volumes of the dialysate bags can be introduced into the optimization strategy.

The key point is then to exploit the capabilities of the Renal Express cycler in order to further improve the efficiency of the therapy. This will be done by suitably mixing at each cycle the dialysate from the sets of bags at different glucose concentration, aiming to obtain a variable glucose level in the peritoneal cavity from cycle to cycle. This topic is addressed in the next section.

Numerical Results Related to Glucose Management

We apply the strategy introduced in the previous sections to determine g*, V', V" on a specific patient undergoing a therapy characterized by the following global parameters: $V_{tot}$=15 liters, $T_{tot}$=9 hours, $V_{max}$=2 liters. The available glucose concentrations are $g_1$=1.36%≡75.6 mmol/l, $g_2$=2.27%≡126.1 mmol/l and $g_3$=3.86%≡214.4 mmol/l. Under these constraints, the admissible ranges for ultrafiltration and glycaemia are the following:
- maximal ultrafiltration: 2.688984 liters,
- maximal glycaemia: 8.927878 [mmol/l],
- minimal ultrafiltration: 0.309521 liters.
- minimal glycaemia: 6.862207 [mmol/l].

We now apply the optimization strategy for several choices of the targets on glycaemia and ultrafiltration.

The results are summarized by the following four examples.

Example 1

Admissible Targets on Glycaemia and Ultrafiltration

| target | | |
|---|---|---|
| ultrafiltration | 1.5 | [l] |
| glycaemia | 7.895 | [mmol/l] |
| results | | |
| optimal glucose concentration | 145.521 | [mmol/l] |
| ultrafiltration | 1.498 | [l] |
| glycaemia | 7.896 | [mmol/l] |
| g' | 126.1 | [mmol/l] |
| g" | 214.4 | [mmol/l] |
| V' | 11.7 | [l] |
| V" | 3.299 | [l] |

Example 2

Admissible Targets on Glycaemia and Ultrafiltration

| target | | |
|---|---|---|
| ultrafiltration | 1 | [l] |
| glycaemia | 7 | [mmol/l] |
| results | | |
| optimal glucose concentration | 102.814 | [mmol/l] |
| ultrafiltration | 0.769 | [l] |
| glycaemia | 7.264 | [mmol/l] |
| g' | 75.6 | [mmol/l] |
| g" | 126.1 | [mmol/l] |
| V' | 6.916 | [l] |
| V" | 8.083 | [l] |

Example 3

Unreachable Target on Ultrafiltration

| target | | |
|---|---|---|
| ultrafiltration | 3 | [l] |
| glycaemia | 7 | [mmol/l] |
| results | | |
| optimal glucose concentration | 169.650 | [mmol/l] |
| ultrafiltration | 1.913 | [l] |
| glycaemia | 8.255 | [mmol/l] |
| g' | 126.1 | [mmol/l] |
| g" | 214.4 | [mmol/l] |
| V' | 7.601 | [l] |
| V" | 7.398 | [l] |

Example 4

Unreachable Target on Glycaemia

| target | | |
|---|---|---|
| ultrafiltration | 1 | [l] |
| glycaemia | 6 | [mmol/l] |
| results | | |
| optimal glucose concentration | 73.372 | [mmol/l] |
| ultrafiltration | 0.271 | [l] |
| glycaemia | 6.829 | [mmol/l] |
| g' | 75.6 | [mmol/l] |
| g" | 126.1 | [mmol/l] |
| V' | 15 | [l] |
| V" | 0 | [l] |

Optimization by Variable Glucose Concentration

In the previous section we discussed how to determine the optimal glucose exposure and how to obtain it by mixing fresh dialysate from several bags of different concentration of glucose. In this section we discuss how to further improve the efficiency of the overnight therapy by suitably partitioning the available charge of glucose on the cycles of a variable tidal peritoneal dialysis.

Again, we split this task in several steps.
1. definition of a variable tidal injection-extraction pattern by means of the $\alpha$, $\beta$, $\gamma$, $\delta$ parametrization.
2. definition of a variable glucose injection pattern by means of the new parameters $\epsilon$, $\eta$.
3. Definition of the fraction of each bag to be injected at each cycle to obtain the desired glucose concentration.

At this point, the already existing optimization algorithm will be able to compute a set of control parameters N, $\alpha$, $\beta$, $\gamma$, $\delta$, $\epsilon$, $\eta$ that satisfy a suitable optimality condition defined by the user, as for example the maximization of the KT/V urea, the KT/V creatinine and the ultrafiltration.

Definition of a Variable Glucose Injection Pattern by Means of the New Parameters $\epsilon$, $\eta$ At the injection phase of each cycle we associate a glucose concentration $g_i$, $i=1, \ldots, N$. The concentration $g_i$ may change from cycle to cycle within the range g' and g" representing the glucose concentrations of the two sets of bags. In order to define the concentrations $g_i$ we apply the following methodology for the injected volumes $\Delta V_i$ and for the dwell times $\Delta T_i$. Precisely, we set $$g_i = (\epsilon + \eta i) g_{i-1}, i=2, \ldots, N, \quad (6)$$

where $\epsilon$, $\eta$ are two new control parameters to be managed by the optimization algorithm. Furthermore, the sequence $g_i$ must satisfy the following constraints, $$\sum_{i=1}^{N} g_i \Delta V_i = g' V' + g'' V'' = G_{tot}. \quad (7)$$

arising from the mass conservation principle. This equation ensures that the sum of the glucose quantity injected at each cycle equals the total available quantity. Finally, we require that $$g' \le g_i \le g'', i=1, \ldots, N, \quad (8)$$

as already mentioned before. We observe that the sequence of glucose concentrations $g_i$, completely determined by means of equations (6), (7) does not necessarily satisfy the constraint (8). For this reason, the original sequence $g_i$ is modified by redistributing the exceeding glucose $g_i-g'$ (in the cases $g_i-g'$) or the missing glucose $g'-g_i$ (in the cases $g_i<g'$) on the remaining admissible cycles.

Definition of the Fraction of Each Bag to be Injected at Each Cycle to Obtain the Desired Glucose Concentration After having defined the variable glucose concentrations $g_i$ i=1, . . . , N, we introduce the volumes $\Delta V'_i$ and $\Delta V''_i$ that represent the fractions of $\Delta V_i$ that have to be poured from the sets of bags at concentrations g' and g" respectively, in order to obtain a mixture of volume $\Delta V_i$ and concentration $g_i$. According to the mass conservation principle, the volumes $\Delta V'_i$ and $\Delta V''_i$ satisfy the following equations, $$\begin{cases} g'\Delta V'_i + g''\Delta V''_i = g_i \Delta V_i, \\ \Delta V'_i + \Delta V''_i = \Delta V_i. \end{cases}$$

Provided that $g' \leq g_i \leq g''$, this system of equations always admits an acceptable solution that is, $$\begin{cases} \Delta V'_i = \frac{g'' - g_i}{g'' - g'} \Delta V_i, \\ \Delta V''_i = \frac{g_i - g'}{g'' - g'} \Delta V_i. \end{cases}$$

The volumes $\Delta V'_i$ and $\Delta V''_i$ are positive and satisfy, $$\sum_{i=1}^{N} \Delta V'_i = V', \quad \sum_{i=1}^{N} \Delta V''_i = V'',$$

ensuring that each set of bags will be completely exploited.

CONCLUSIONS

Starting from very basic input parameters like $V_{tot}$; $T_{tot}$ and $V_{max}$, the procedures and the mathematical algorithms proposed in the previous sections help the clinicians to manage all the aspects of the definition of the overnight peritoneal dialysis for a specific patient. Indeed, both the definition of what sets of dialysate bags should be prescribed and the optimal repartition of the available resources over several cycles managed by an advanced automatic device are considered. This is a very general strategy of view on the optimization of dynamic peritoneal dialysis, which makes clinicians able to perform this kind of therapy at its maximal efficiency for each specific patient.

The invention claimed is:

1. A method for prescribing a dialysis treatment comprising the following steps:
    collecting patient specific data,
    determining at least one target,
    defining a series of values of the type [V;t] which allow to achieve said target wherein V represents the volume of dialysate used and t the duration of treatment, based on said patient specific data,
    displaying said series of values on a map.

2. The method according to claim 1, whereby the dialysis is a peritoneal dialysis.

3. The method according to claim 2, wherein said target is taken from the followings: Ultra-filtration, sodium removal or glucose absorption.

4. The method according to claim 2, wherein said target is a clearance of a solute taken from creatinine, urea, or microglobuline.

5. The method according to claim 1, wherein said series of values is displayed in the form of a continuous curve in an orthogonal bi-dimensional graph.

6. The method according to claim 5, which includes the displaying of several series of a values on a map, each series corresponding to a specific target value and defining an isoline on said graph.

7. The method according to claim 1, wherein the patient specific data are obtained by a test, such as PET, PDC miniPET or other dialysis tests able to calculate the patient peritoneal membrane characteristics.

8. The method according to claim 1, wherein additional information related to at least another patient specific parameter are provided on the map.

9. The method according to claim 8, wherein said other parameter is taken from the followings: sodium removal, glucose absorption, ultra-filtration, protein intake, microglobuline clearance, effect on diet and kidney function.

10. A peritoneal dialysis prescription system comprising:
    a first processor for entering patient specific data,
    a second processor for selecting a target,
    a third processor for defining a series of values of the type [V;t] which allow to achieve said target wherein V represents the volume of dialysate used and t the duration of treatment,
    a display adapted for displaying said series of values on a map.

11. The peritoneal dialysis prescription system according to claim 10, wherein said display is adapted to represent said series of values in the form of a continuous curve in an orthogonal bi-dimensional graph.

12. The peritoneal dialysis prescription system according to claim 11, wherein said display is adapted to represent several series of values on a map, each series corresponding to a specific target and defining an isoline on said graph.

13. The peritoneal dialysis prescription system according to claim 11, wherein said target is taken from the followings: Ultra-filtration, sodium removal or glucose absorption.

14. The peritoneal dialysis prescription system according to claim 11, wherein said target is a clearance of a solute taken from the followings: creatinine, urea or microglobuline.

15. The peritoneal dialysis prescription system according to claim 11, wherein the patient specific data are obtained by a test, such as PET, PDC miniPET or other dialysis tests able to calculate the patient membrane characteristics.

16. The peritoneal dialysis prescription system according to claim 11, wherein additional information related to at least another patient specific parameter are provided on the map.

17. The peritoneal dialysis prescription system according to claim 16, wherein said other parameter is taken from the followings: sodium removal, glucose absorption, ultra-filtration, protein intake, microglobuline clearance, effect on diet and kidney function.

18. The peritoneal dialysis prescription system according to claim 11, comprising a second display for displaying the treatment parameters and the expected results for any of said series of values.

19. The peritoneal dialysis prescription system according to claim 11, furthermore comprising automatic parameter recording means which are adapted to automatically record the selected treatment parameters.

20. The method according to claim 8, wherein the additional information related to at least another patient specific parameter is provided in a background of the map.

21. The peritoneal dialysis prescription system according to claim 16, wherein the additional information related to at least another patient specific parameter is provided in a background of the map.

* * * * *